United States Patent
Caumont-Bertrand et al.

(10) Patent No.: US 7,547,729 B2
(45) Date of Patent: Jun. 16, 2009

(54) 1,3-DIPHENYLPROP-2-EN-1-ONE DERIVATIVE COMPOUNDS, PREPARATION METHOD THEREOF AND USES OF SAME

(75) Inventors: Karine Caumont-Bertrand, Frelinghien (FR); Jean-François Delhomel, Acq (FR)

(73) Assignee: Genfit, Loos (FR)

( * ) Notice: Subject to any disclaimer, the term of this patent is extended or adjusted under 35 U.S.C. 154(b) by 279 days.

(21) Appl. No.: 10/585,329

(22) PCT Filed: Jan. 7, 2005

(86) PCT No.: PCT/FR2005/000040

§ 371 (c)(1),
(2), (4) Date: Jul. 6, 2006

(87) PCT Pub. No.: WO2005/073184

PCT Pub. Date: Aug. 11, 2005

(65) Prior Publication Data

US 2008/0058412 A1    Mar. 6, 2008

(30) Foreign Application Priority Data

Jan. 8, 2004  (FR) .................................. 04 00123
Sep. 1, 2004  (FR) .................................. 04 09257

(51) Int. Cl.
*A61K 31/19* (2006.01)
*C07C 65/03* (2006.01)

(52) U.S. Cl. ....................... 514/557; 562/471; 562/472

(58) Field of Classification Search ................. 562/471, 562/472; 514/557
See application file for complete search history.

(56) References Cited

U.S. PATENT DOCUMENTS 5,523,302 A    6/1996    Cain et al.

FOREIGN PATENT DOCUMENTS

| DE | 43 27 365 | 2/1995 |
|---|---|---|
| EP | 0 659 743 | 6/1995 |
| EP | 1 440 688 A1 | 7/2004 |

OTHER PUBLICATIONS

Wang et al. CAS:148:379286.*
Najib et al., 2004, CAS:2004-180204.*
International Search Report for PCT/FR2005/000040 dated May 31, 2005.
Spiegelman, "Perfectives in Diabetes—PPAR-γ: Adipogenic Regulator and Thiazolidinedione Receptor", Diabetes, vol. 47, Apr. 1998, pp. 507-514.

* cited by examiner

*Primary Examiner*—Rei-tsang Shiao
(74) *Attorney, Agent, or Firm*—Nixon & Vanderhye P.C.

(57) ABSTRACT

The invention relates to substituted 1,3-diphenylprop-2-en-1-one derivative compounds, pharmaceutical and/or cosmetic compositions containing same, and the applications thereof in therapeutics and cosmetics. The invention also relates to a method for preparing said derivatives.

6 Claims, 24 Drawing Sheets

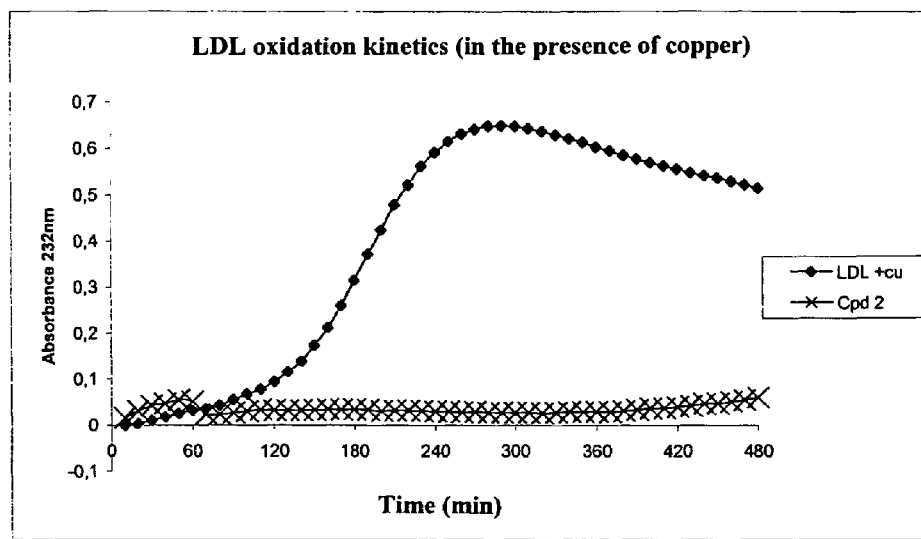
Figure 1a
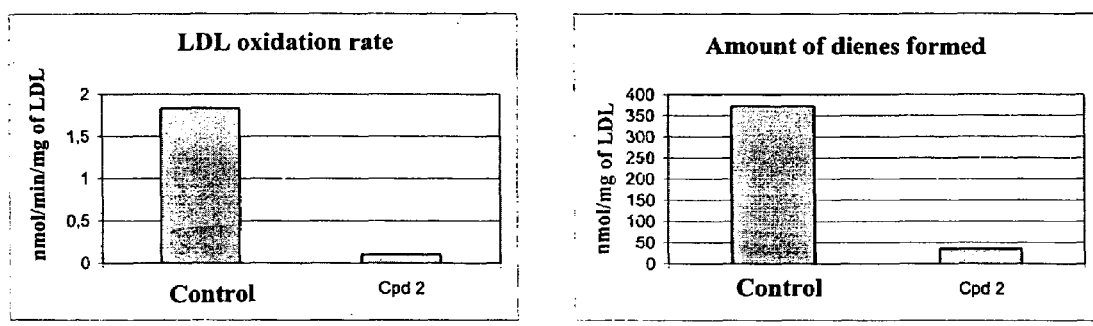
Figure 1b
Figure 1c

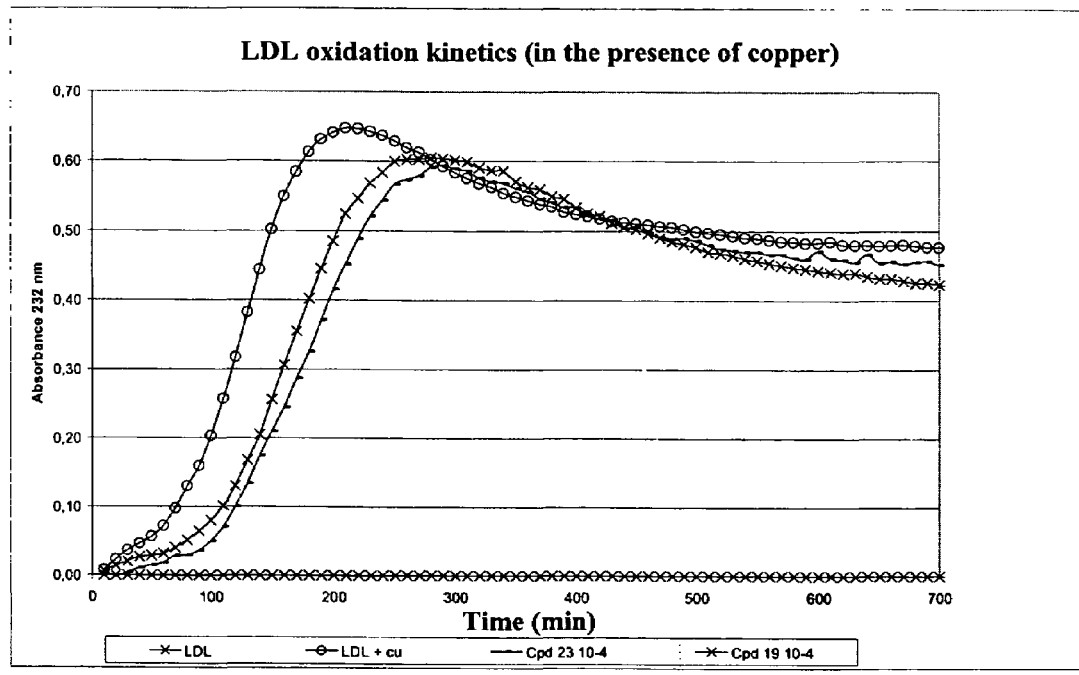
Figure 4a
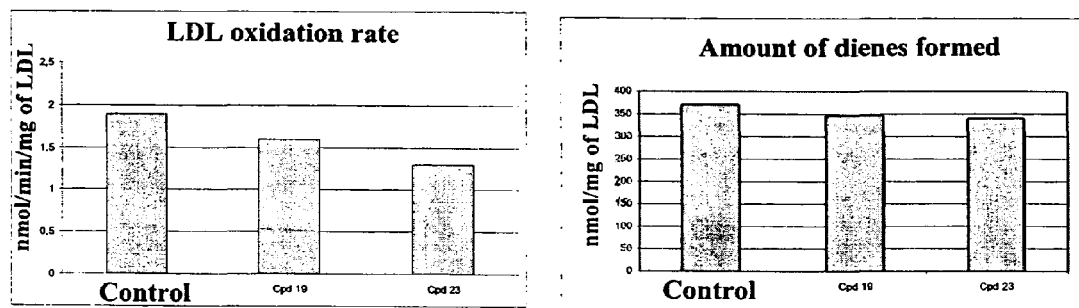
Figure 4b
Figure 4c

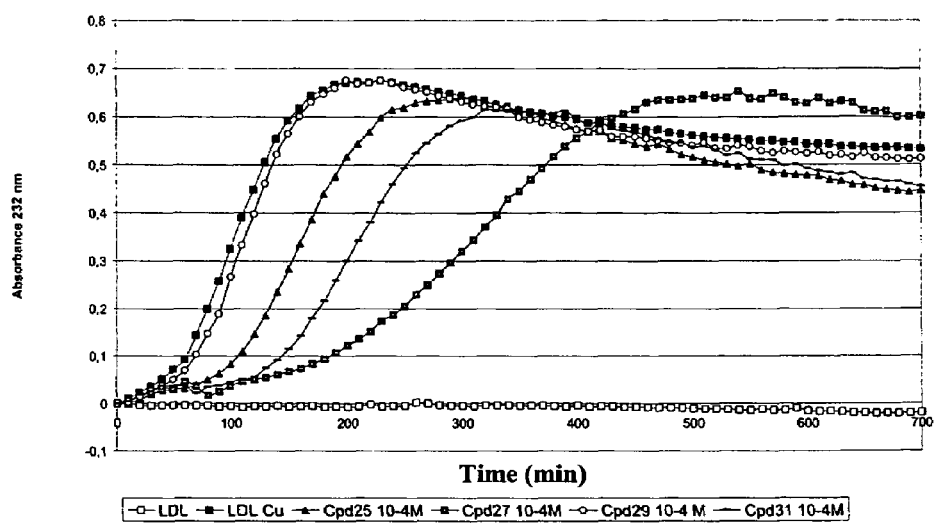
Figure 5a
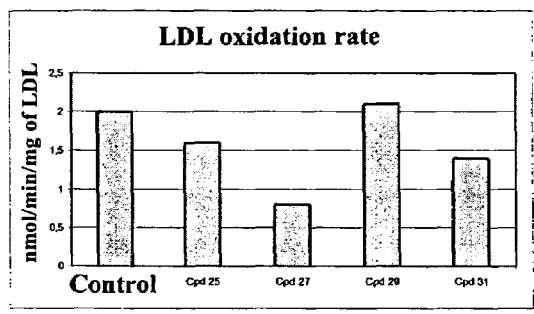 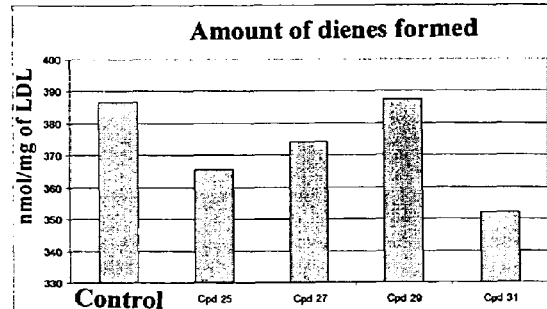
Figure 5b
Figure 5c

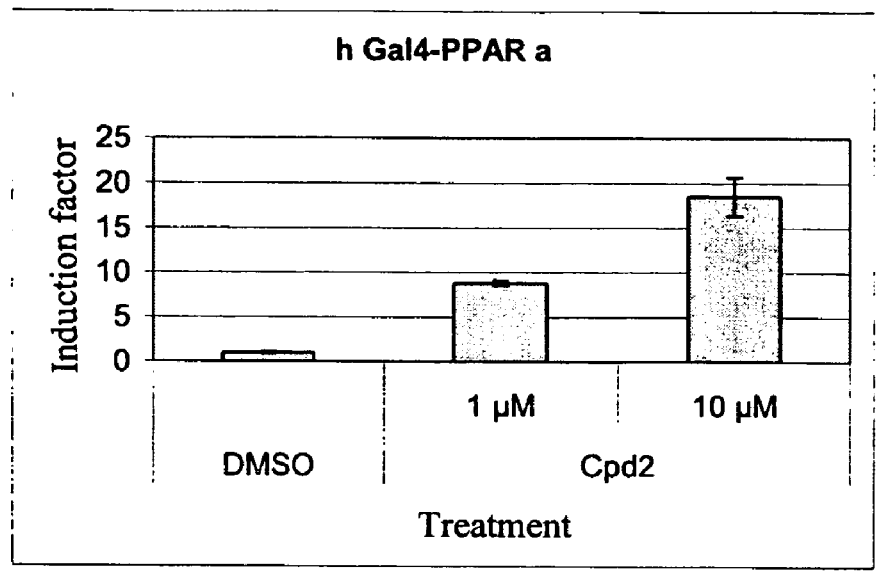
Figure 9a - PPAR α
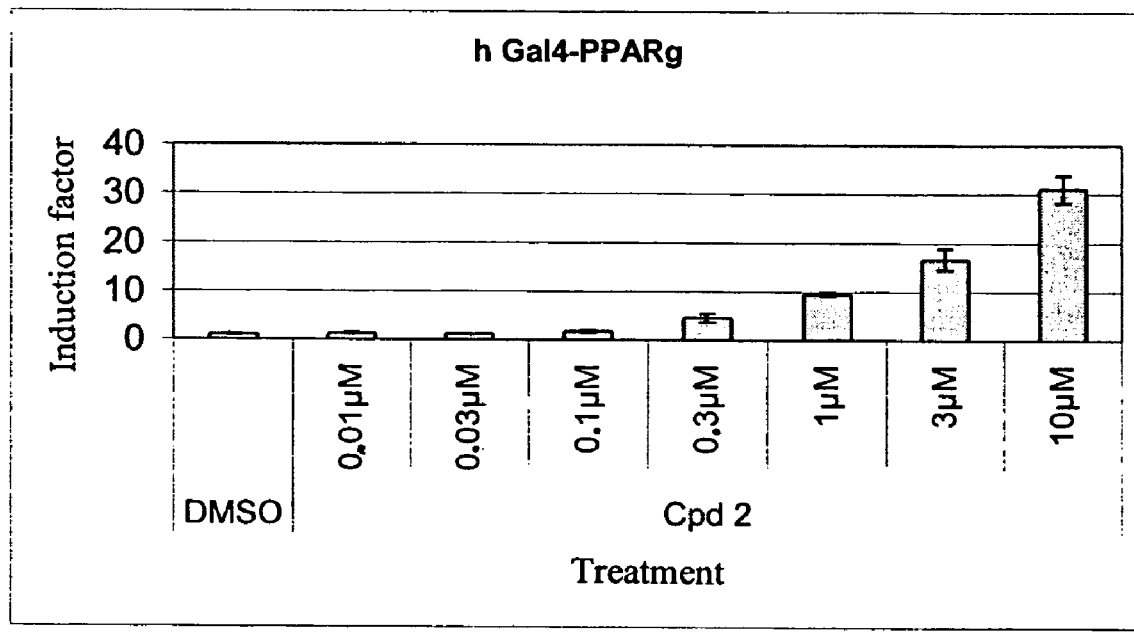
Figure 9b - PPAR γ

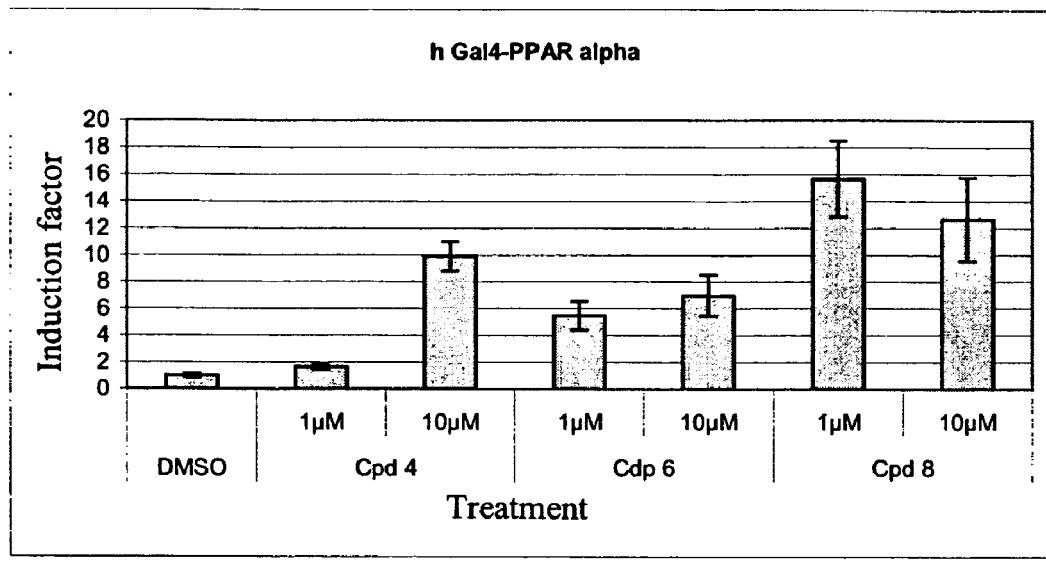
Figure 10a - PPAR $_\alpha$
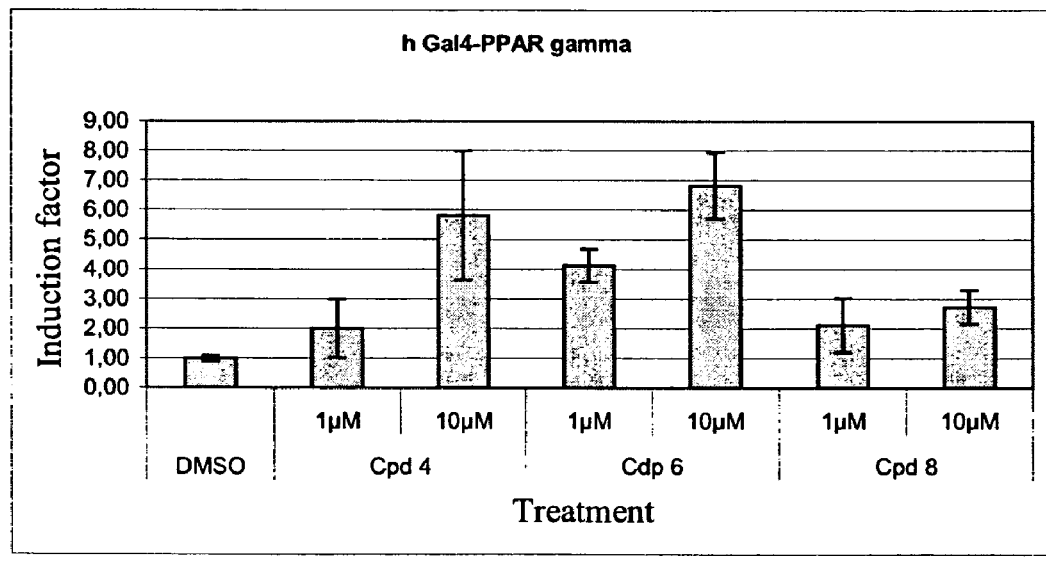
Figure 10b - PPAR $_\gamma$

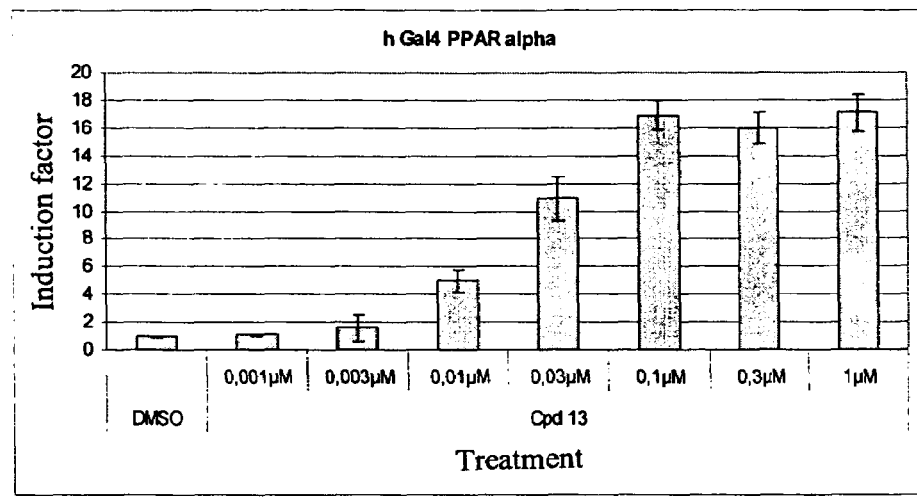
Figure 11a - PPAR α
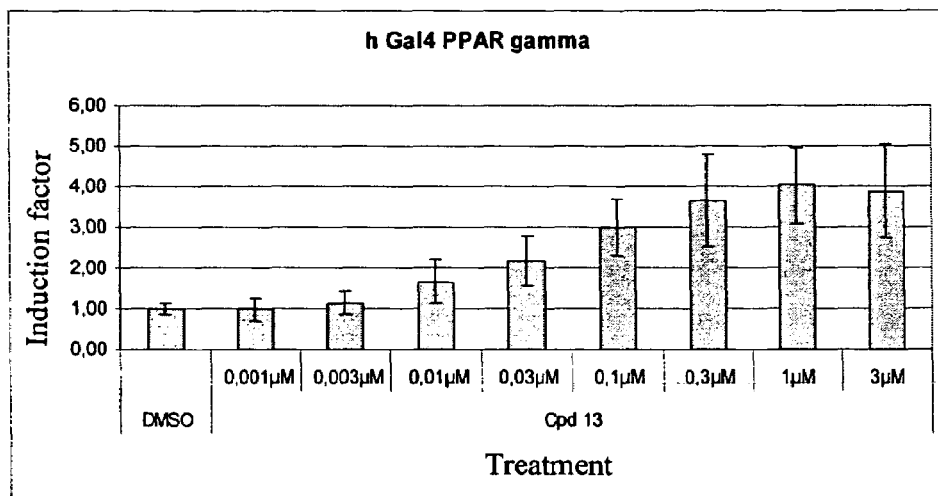
Figure 11b - PPAR γ
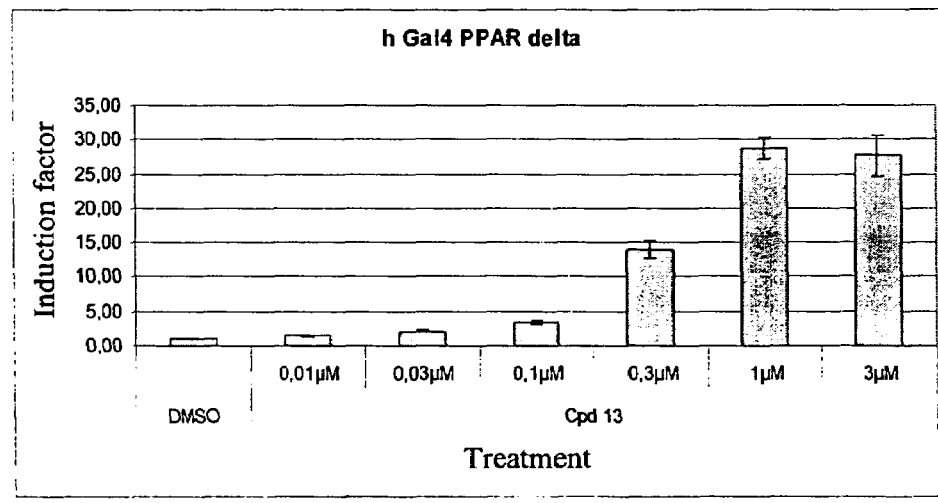
Figure 11c - PPAR δ

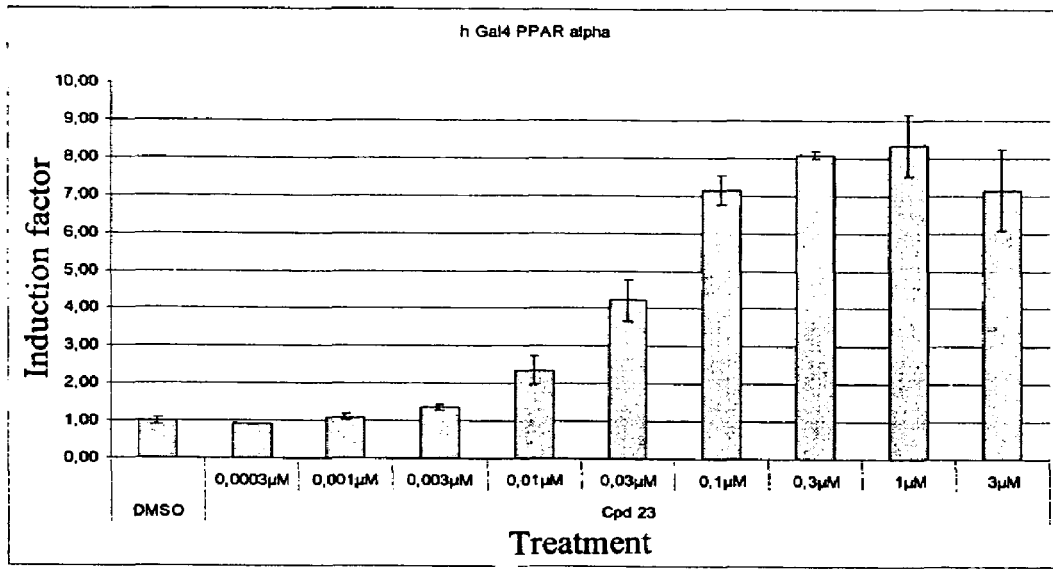
Figure 12a - PPAR α
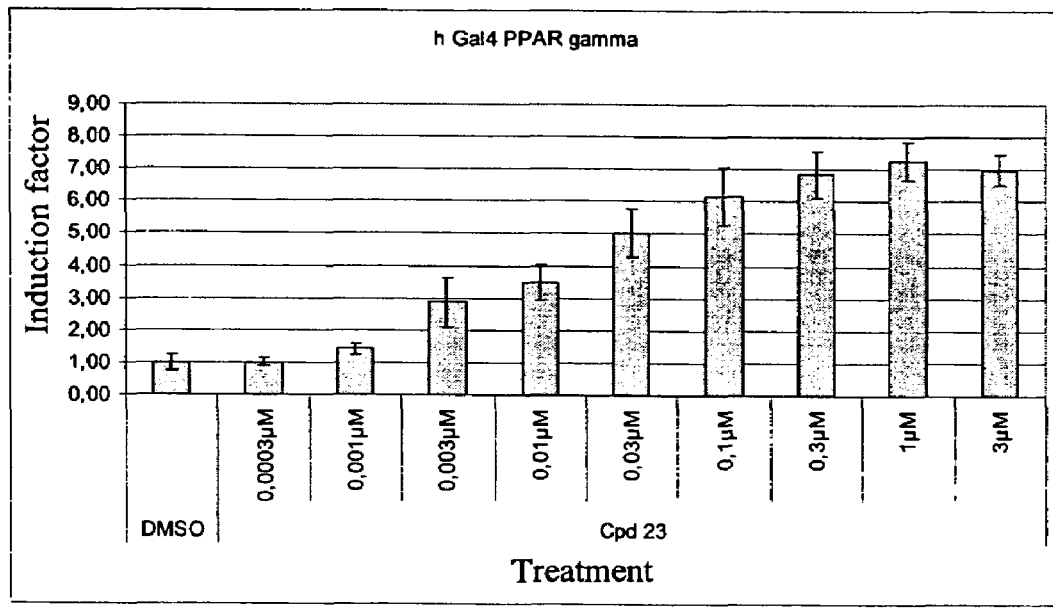
Figure 12b - PPAR γ

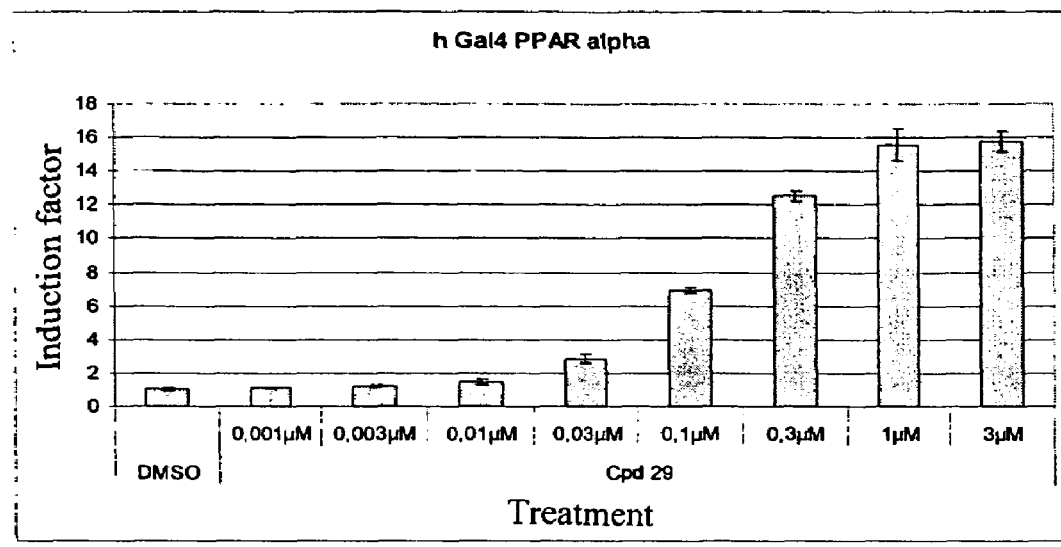
Figure 13a - PPAR α
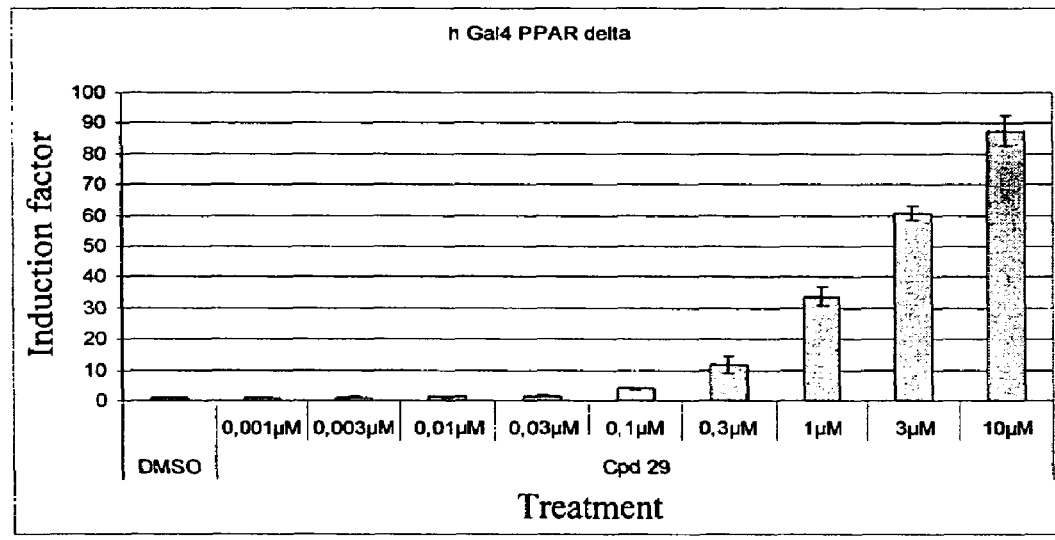
Figure 13b - PPAR δ

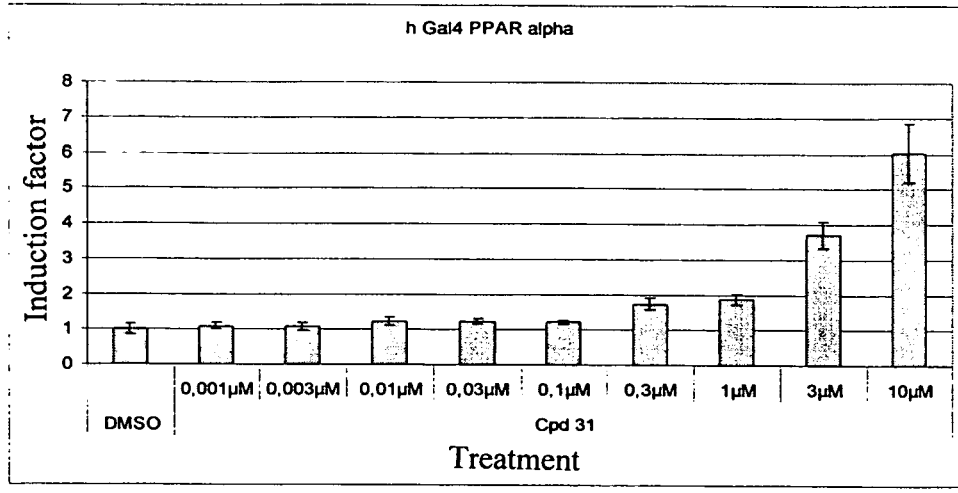
Figure 14a - PPAR $\alpha$
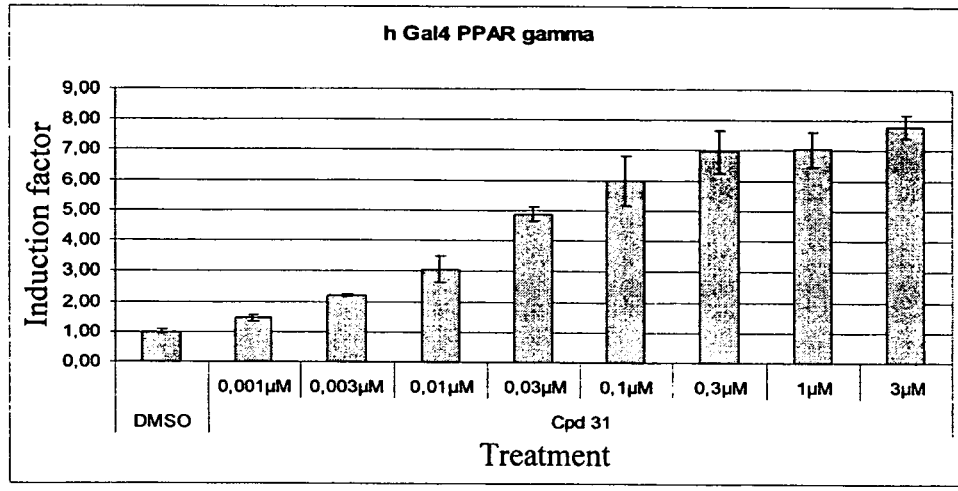
Figure 14b - PPAR $\gamma$
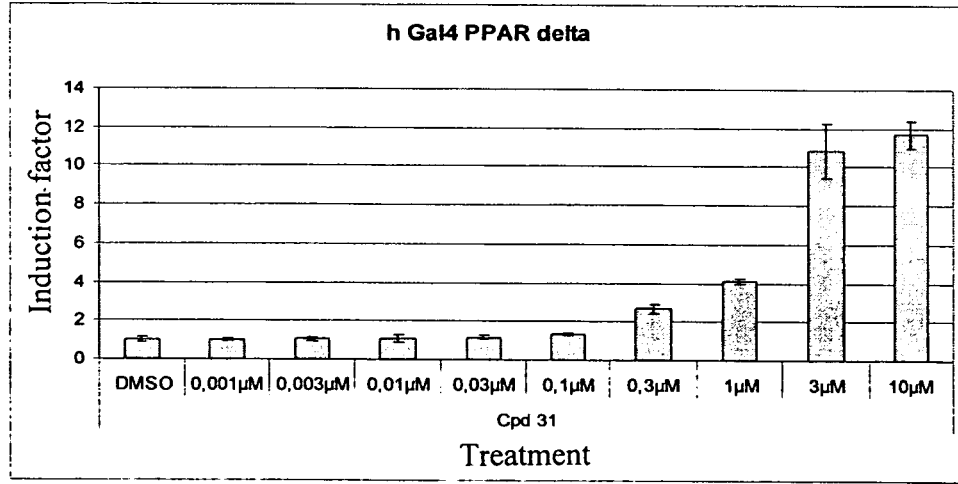
Figure 14c - PPAR $\delta$

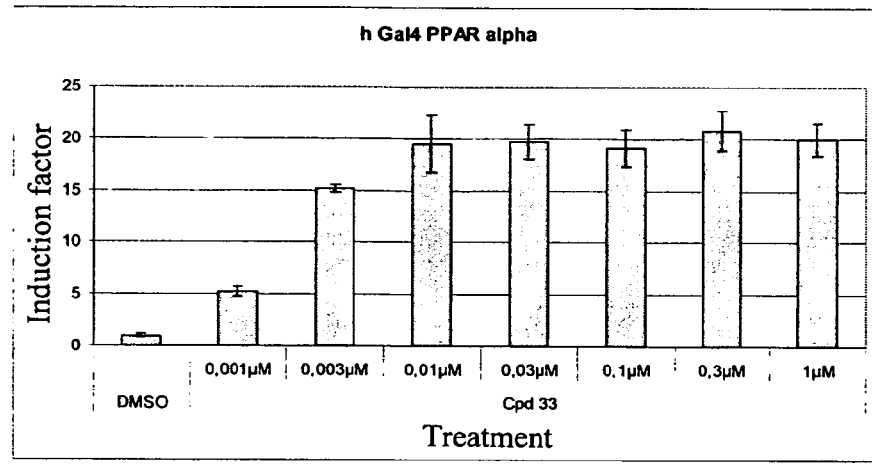
Figure 15a - PPAR α
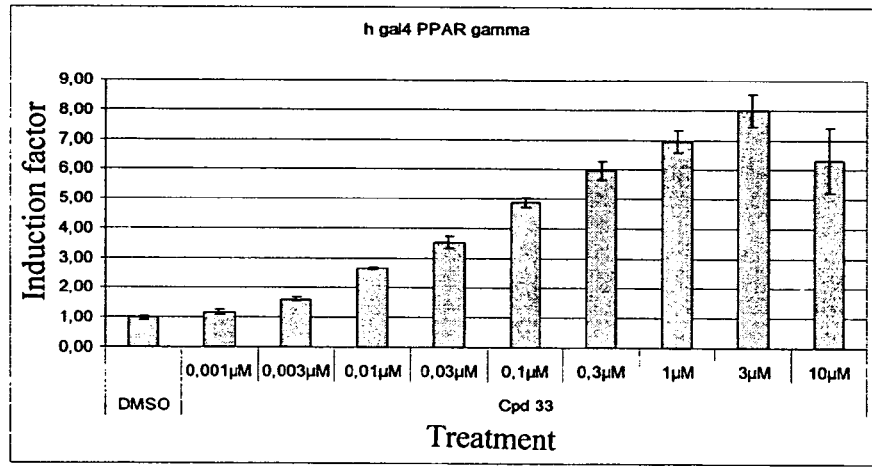
Figure 15b - PPAR γ
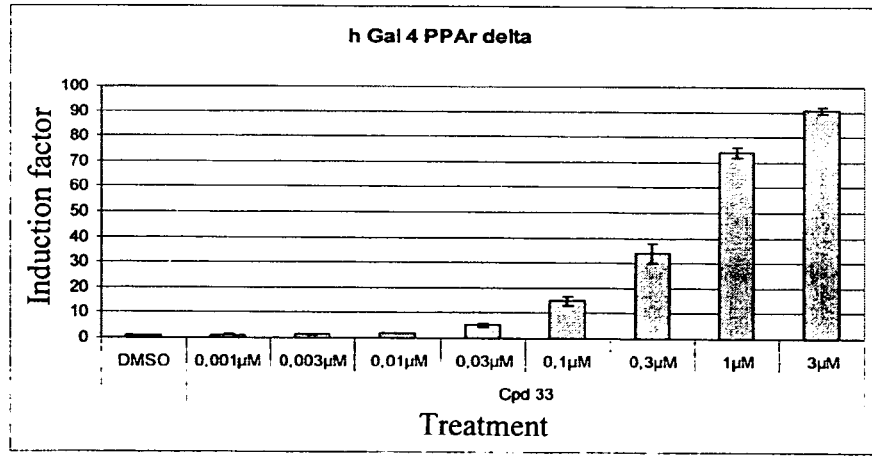
Figure 15c - PPAR δ

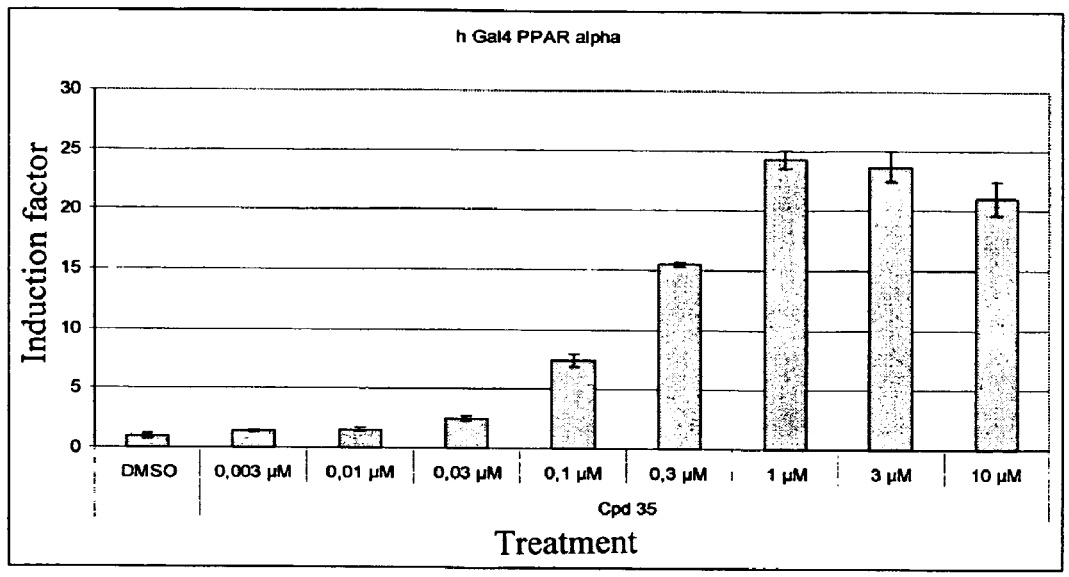
Figure 16a - PPAR α
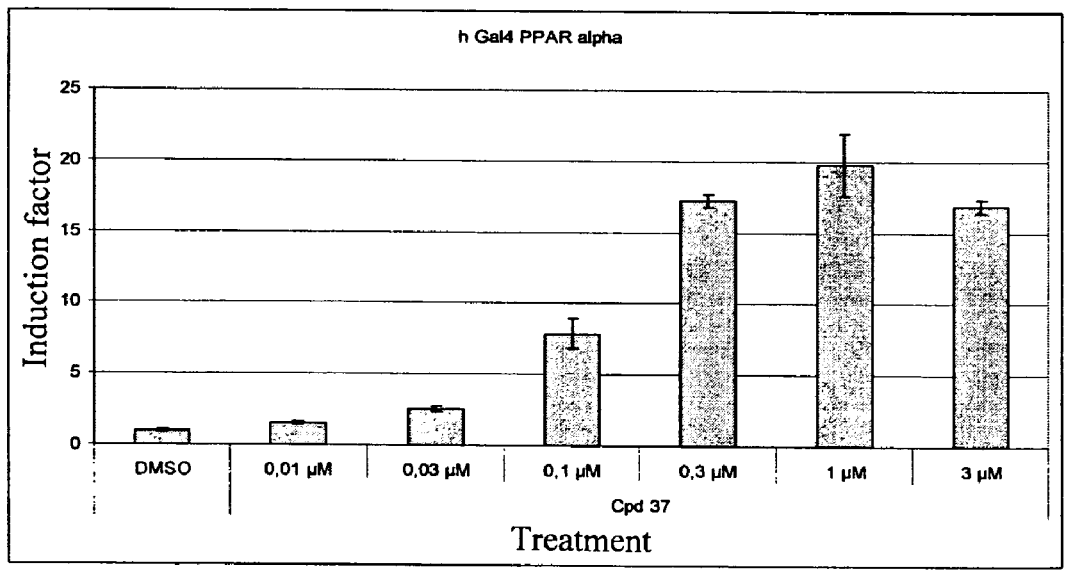
Figure 17a - PPAR a

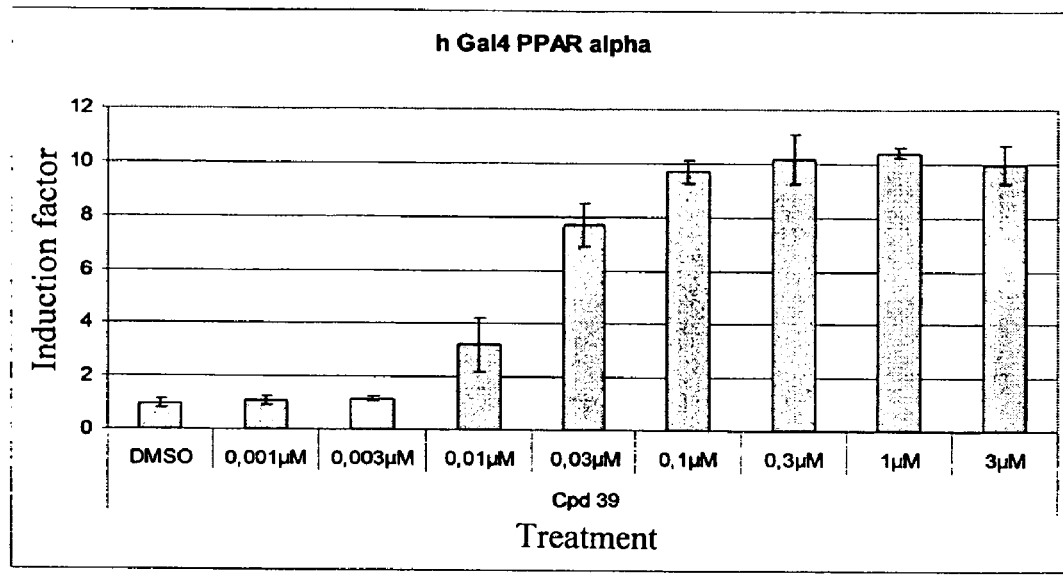
Figure 18a - PPAR α
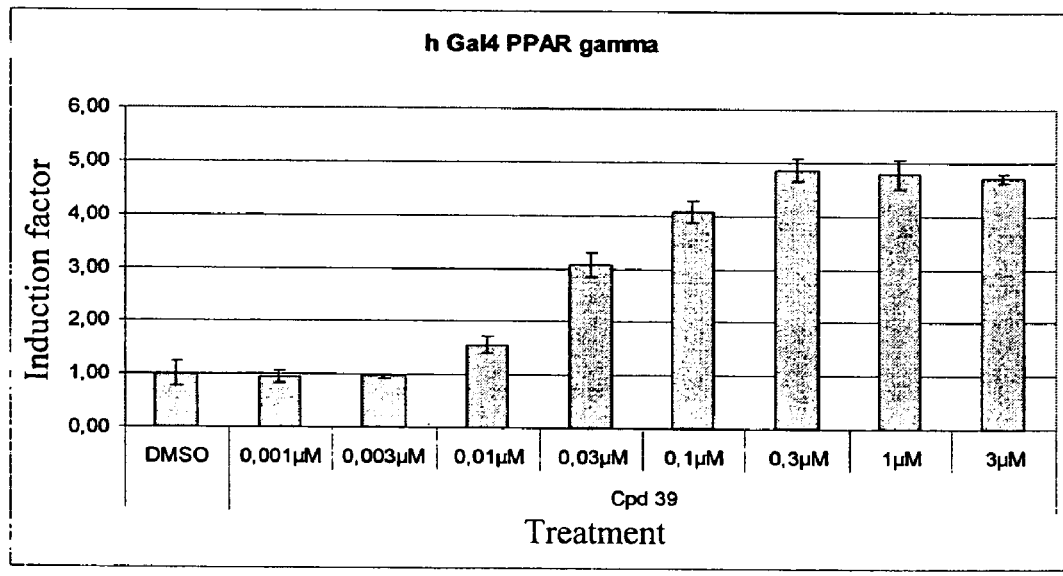
Figure 18b - PPAR γ

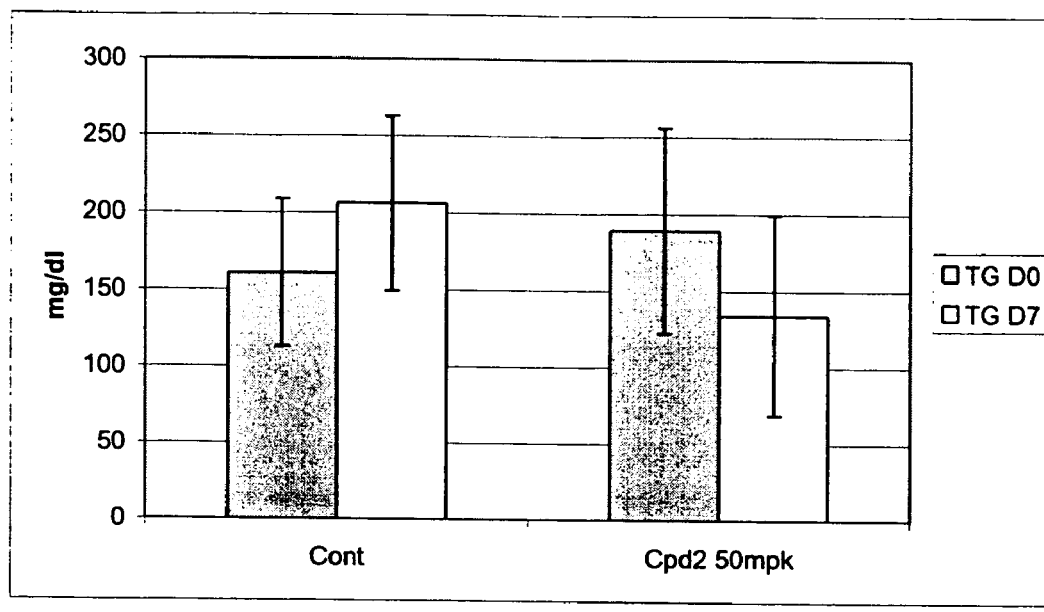
Figure 19a - Total triglycerides
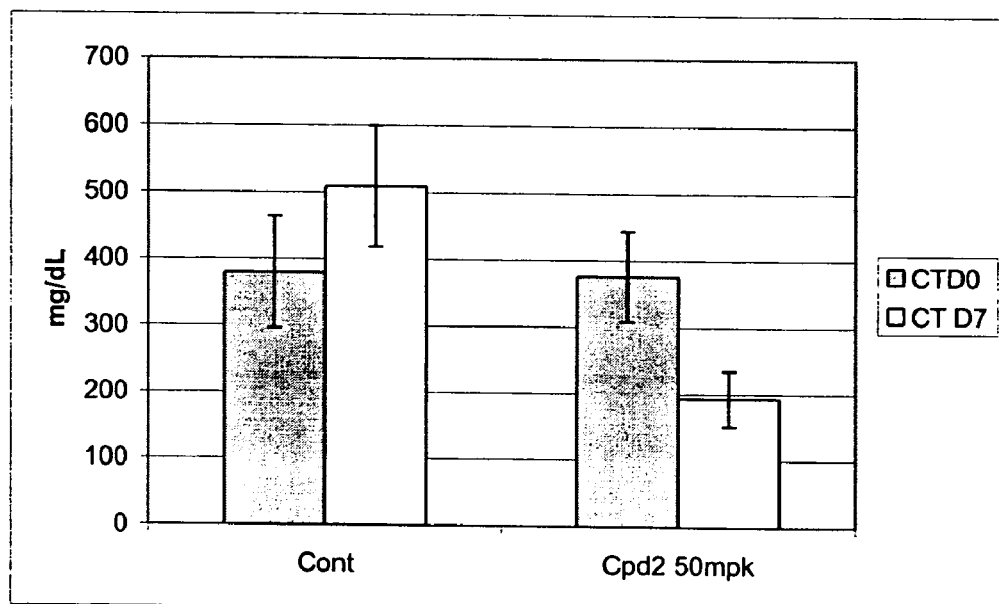
Figure 19b - Total cholesterol

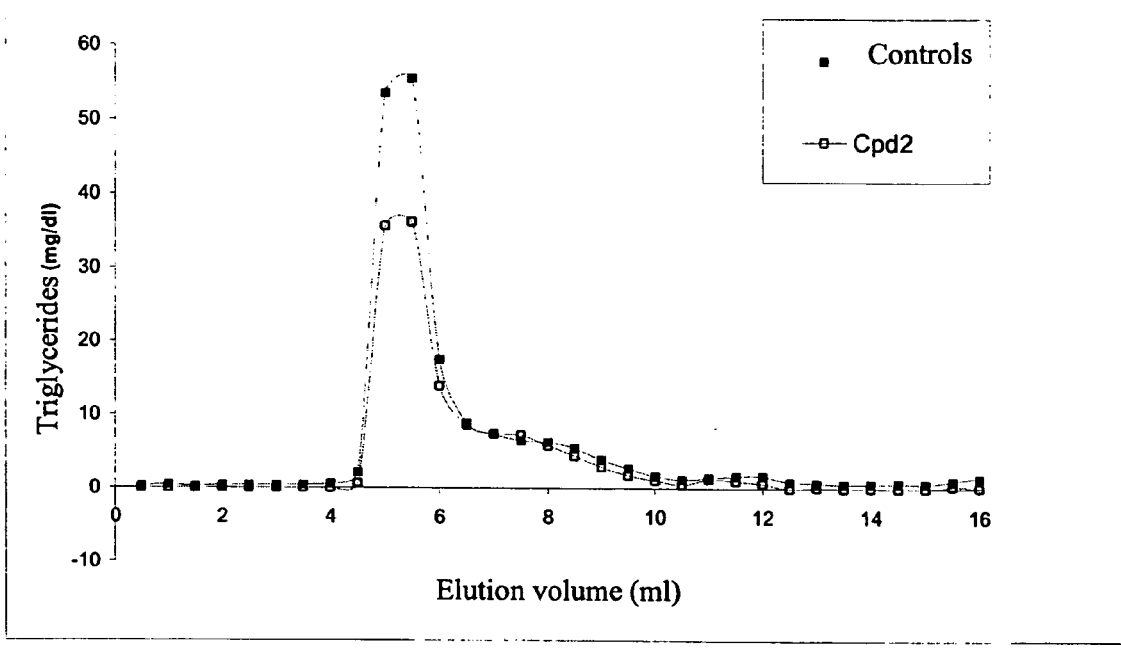
Figure 19c - Triglyceride distribution
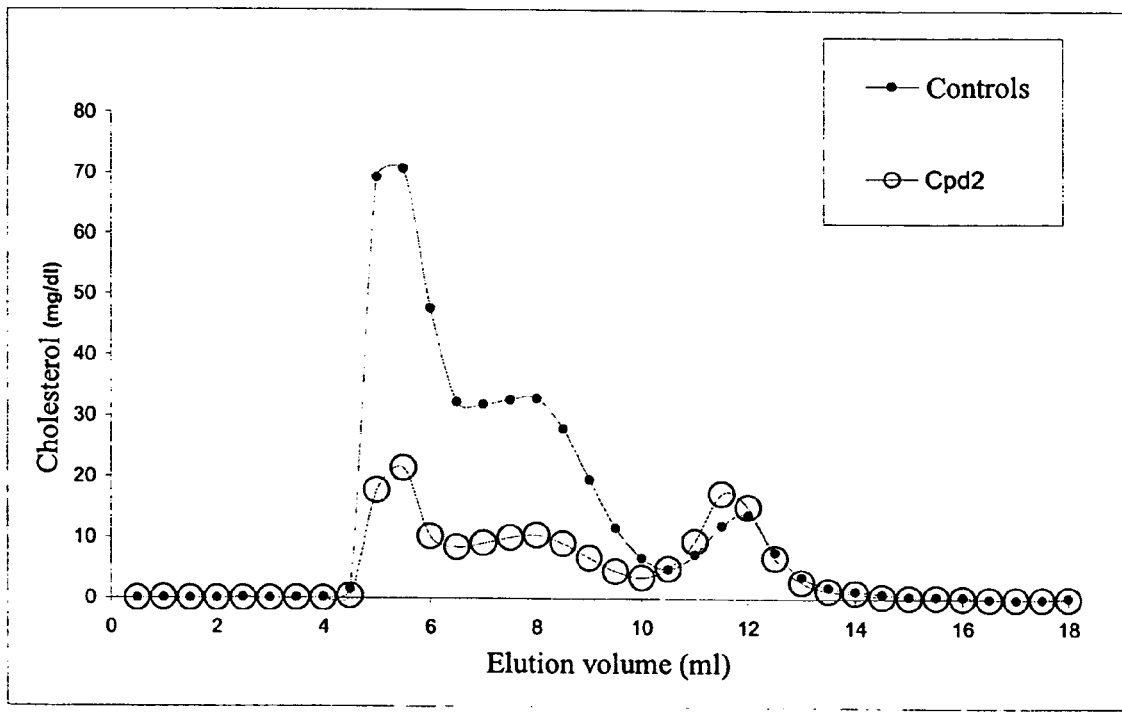
Figure 19d - Cholesterol distribution

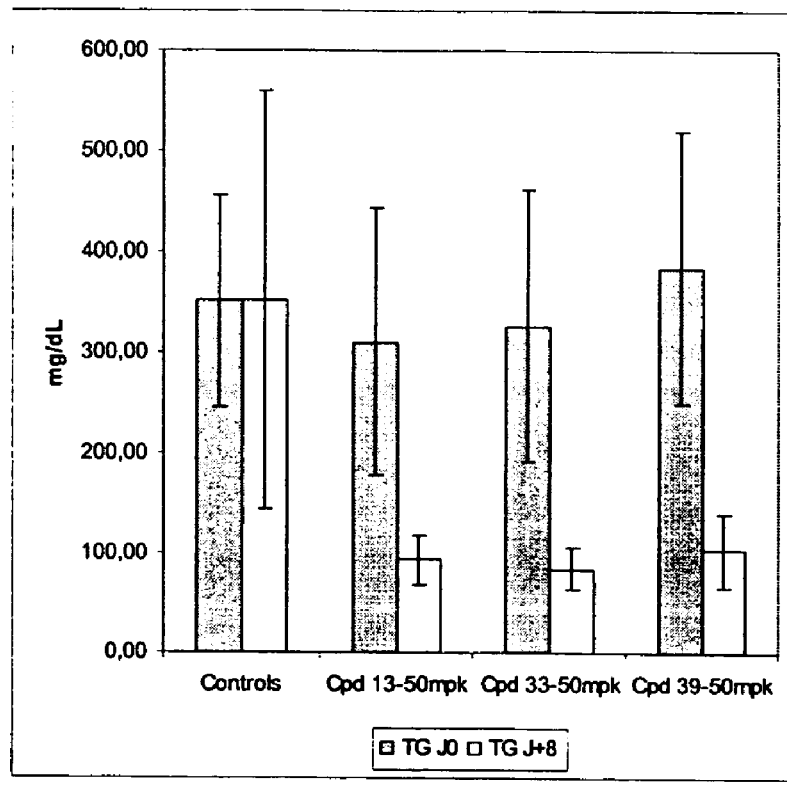
Figure 20a - Total triglycerides
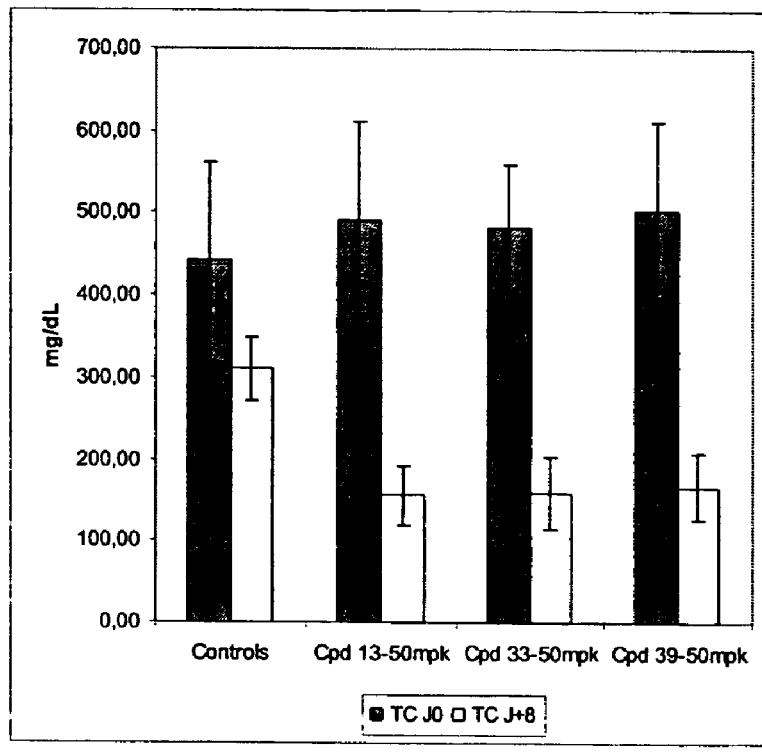
Figure 20b - Total cholesterol

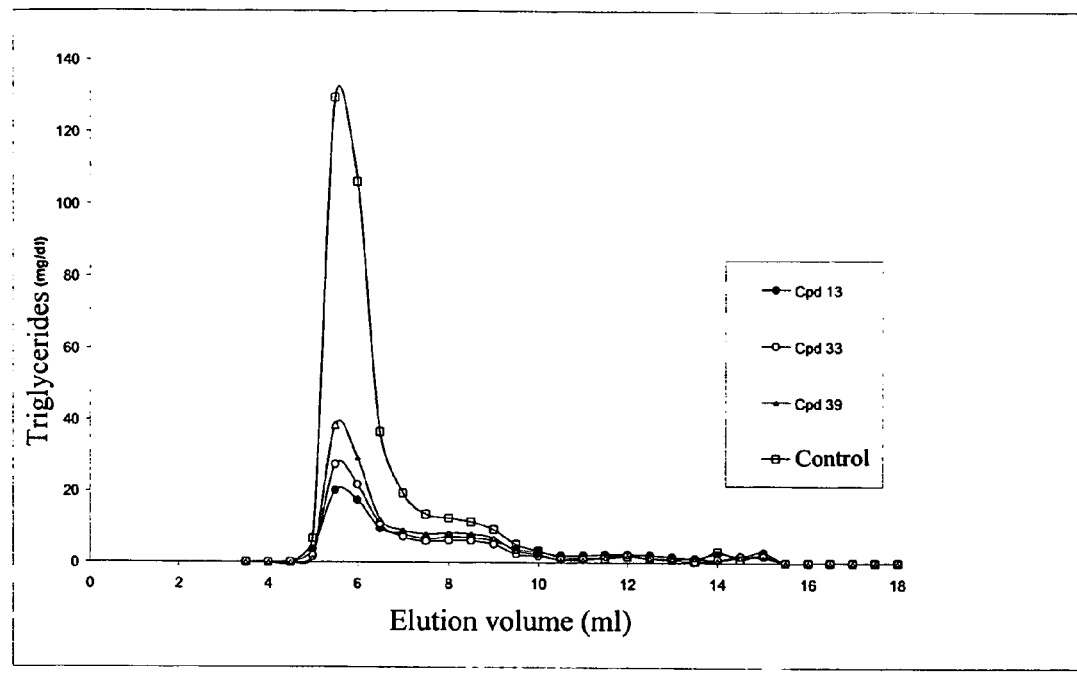
Figure 20c - Triglyceride distribution
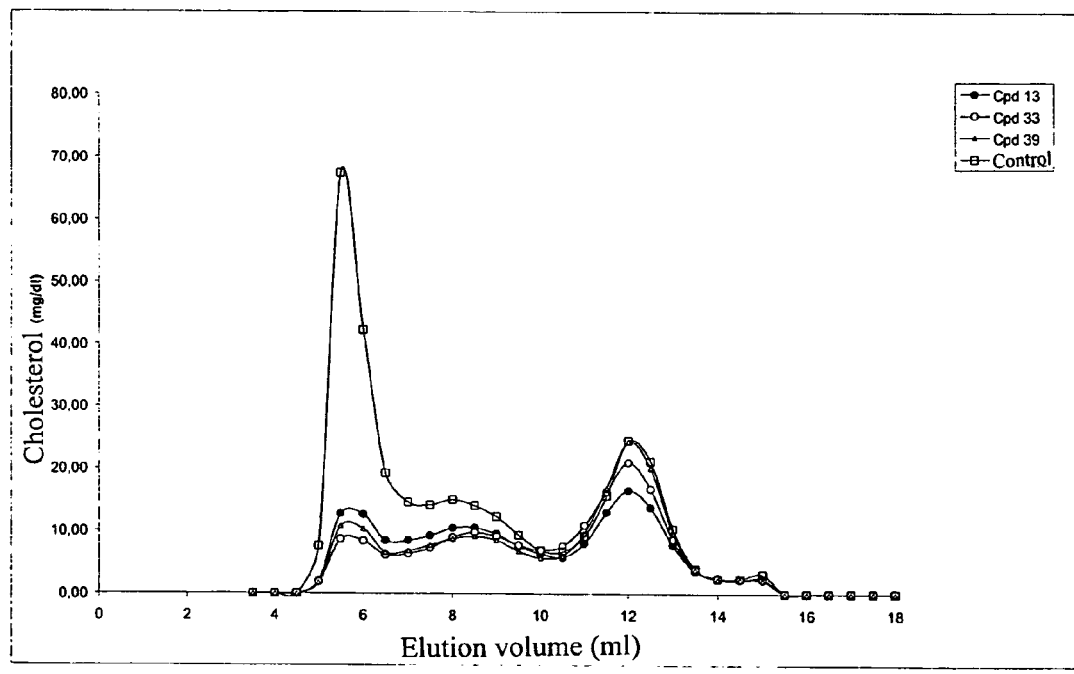
Figure 20d - Cholesterol distribution

1,3-DIPHENYLPROP-2-EN-1-ONE DERIVATIVE COMPOUNDS, PREPARATION METHOD THEREOF AND USES OF SAME

This application is the US national phase of international application PCT/FR2005/000040 filed 7 Jan. 2005, which designated the U.S. and claims priority to FR 0400123 filed 8 Jan. 2004, and FR 0409257 filed 1 Sep. 2004, the entire content of each of which is hereby incorporated by reference.

The invention relates to substituted 1,3-diphenylprop-2-en-1-one derivatives, pharmaceutical and/or cosmetic compositions comprising same, and the applications thereof in therapeutics and/or cosmetics, particularly in the fields of human and animal health. The invention also relates to a method of preparing said derivatives.

The compounds according to the invention represent an advantageous therapeutic tool for improving pathologies related to disregulations of lipid and/or glucose metabolism (hyperlipidemia, diabetes, obesity, etc.) and can be used in particular for the prevention or treatment of cardiovascular diseases (particularly coronary heart disease, cerebral ischemia and peripheral arterial diseases), dyslipidemias, pathologies associated with syndrome X, diabetes, obesity, hypertension, inflammatory diseases, dermatologicalal diseases (psoriasis, atopic dermatitis, acne, etc.), asthma, disorders linked to oxidative stress, the effects of ageing in general, for example skin ageing, particularly in the cosmetic field (appearance of wrinkles, etc.). The compounds according to the invention are capable of exerting a prophylactic activity in terms of neuroprotection, and also of providing active neuroprotection in the acute phase of cerebral ischemic events, which are one of the major complications of cardiovascular disease.

By acting simultaneously on several cardiovascular risk factors, the inventive compounds enable a reduction in overall cardiovascular risk.

Coronary heart disease, cerebral ischemia and peripheral arterial diseases are the most common cardiovascular diseases, according to the International Atherosclerosis Society (*Harmonized Clinical Guidelines on Prevention of Atherosclerotic Vascular Disease*, 2003).

Cardiovascular diseases are currently one of the leading causes of death in adults in the majority of industrialized countries and in some developing countries. Among the cardiovascular diseases, cerebrovascular disease is the third leading cause of mortality and the leading cause of disability in adults. The need for effective strategies for the prevention and/or treatment of these diseases has become a worldwide urgency.

Dyslipidemias (hypercholesterolemia, hypertriglyceridemia), diabetes and hypertension are some of the clearly established cardiovascular risk factors (IAS, 2003). It also appears that insufficient protection of lipoproteins against oxidation is an identified risk factor.

Epidemiological studies have revealed a synergistic effect between these different factors. The simultaneous presence of several factors leads to a dramatic increase in cardiovascular risk. It is therefore appropriate to speak in terms of global risk for cardiovascular diseases.

Thus there is a real need for products that can act simultaneously on these different risk factors and thereby reduce the risk of cardiovascular disease but also treat each deregulation and its consequences in an independent manner (dyslipidemias, diabetes, hypertension, cerebral ischemia, pathologies associated with syndrome X, obesity, etc.).

The inventors have shown in a surprising manner that the compounds according to the invention are PPAR (Peroxisome Proliferator-Activated Receptor) activators and that they therefore represent an advantageous therapeutic tool.

Indeed, it is well known that the PPARs are associated with lipid and glucose metabolism. PPAR activators, such as fibrates for example, regulate serum cholesterol and triglyceride concentrations via activation of PPARα (Hourton, Delerive et al. 2001). Fibrate therapy leads to an increase in fatty acid oxidation in liver. These compounds also reduce the level of synthesis and expression of triglycerides (Staels and Auwerx 1998). PPARα activators can also correct hyperglycemia and insulin levels. Fibrates also decrease adipose tissue mass through a mechanism which is independent of food intake and leptin gene expression (Guerre-Millo, Gervois et al. 2000).

The therapeutic interest of PPARγ agonists has been widely studied in type 2 diabetes (Spiegelman 1998). It has been shown that PPARγ agonists restore insulin sensitivity in target tissues and lower plasma glucose, lipids and insulin levels in both animal models and human type 2 diabetes (Ram 2003).

PPAR activation by ligands also plays a role in regulating the expression of genes participating in processes like inflammation, angiogenesis, cell proliferation and differentiation, apoptosis and the activities of iNOS, MMPase and TIMPs. Activation of PPARα in keratinocytes leads to an arrest of their proliferation and promotes the expression of genes involved in cell differentiation (Komuves, Hanley et al. 2000).

It has also been shown that PPAR activation interferes with the differentiation, maturation, migration and immunogenecity of dendritic cells, which are the most potent antigen-presenting cells (Gosset et al. 2001; Nencioni et al. 2002; Angeli et al. 2003).

The PPARs have anti-inflammatory properties because they show negative interference in transcription mechanisms involving other transcription factors such as NF-kB or transcription activators (STAT) and AP-1 (Desvergne and Wahli 1999). Said anti-inflammatory and antiproliferative properties make the PPARs interesting therapeutic targets for the treatment of diseases such as vascular occlusive disease (atherosclerosis, etc.), cerebral ischemia, hypertension, diseases related to neovascularization (diabetic retinopathies, etc.), inflammatory diseases (Bowen's disease, psoriasis, etc.), asthma and neoplastic diseases (cardcinogenesis, etc.).

In addition, the compounds according to the invention have the advantage of being antioxidants.

In fact, free radicals play a role in a wide range of pathologies including cardiovascular disease (atherosclerosis, etc.), cerebral ischemia, genetic and metabolic disorders (diabetes, etc.) but also in infectious and degenerative diseases (Alzheimer's, Parkinson's, prion diseases, etc.), ophthalmic disorders, ageing, allergies, cancer initiation and promotion (Mates, Perez-Gomez et al. 1999).

Reactive oxygen species (ROS) are produced during normal cell functioning. ROS comprise the hydroxyl radical (OH), superoxide anion ($O_2^-$), hydrogen peroxide ($H_2O_2$) and nitric oxide (NO). Said species are very labile and, due to their high chemical reactivity, constitute a danger to the biological functions of cells by inducing lipid peroxidation, oxidation of certain enzymes and very extensive oxidation of proteins leading to degradation thereof.

ROS are processed via an antioxidant system that comprises an enzymatic component (superoxide dismutase, catalase and gluthatione peroxidase) and a non-enzymatic component, mainly carotenoids, vitamin C and vitamin E (Gilgun-Sherki, Melamed et al. 2001).

Furthermore, many in vitro and in vivo studies have described the potential participation of oxidized LDL (Low Density Lipoproteins) in atherosclerosis. Atherosclerotic plaque which develops slowly has a cholesterol-rich core surrounded by a fibrous cap. Plaque rupture is increasingly thought to result from chronic inflammatory alterations in the region of the fibrous cap. Inflammatory mediators like cytokines affect several biological processes within the fibrous cap, lowering the resistance thereof to rupture.

The inflammatory cytokines in atheromatous plaque, including interleukin 1, tumor necrosis factor (TNF-α and the surface homolog of TNFα named CD-40 ligand), lead to the production by macrophages and smooth muscle cells of enzymes that can weaken the extracellular matrix. Rupture of the fibrous cap can result from occlusive thrombi.

The inventive compounds are also advantageous therapeutic tools for the treatment and/or prevention of cerebral ischemia by virtue of their pharmacological and in particular their anti-inflammatory properties.

The initial event in cerebral ischemia takes place in the first few hours and consists in a massive release of glutamate which leads to neuron depolarization and cellular oedema. Calcium influx into the cell induces mitochondrial damage leading to the release of free radicals and the induction of enzymes that promote degradation of neuronal membranes. Calcium influx and free radical production in turn activate certain transcription factors, such as NF-κB. Said activation induces inflammatory processes such as induction of endothelial adhesion proteins, polynuclear neutrophil infiltration of the ischemic focus, microglial activation, induction of enzymes like nitric oxide (NO) synthase type II or cyclooxygenase type II. These inflammatory processes lead to release of NO or prostanoids which are toxic to the cell. Together, these processes result in a phenomenon of apoptosis inducing irreversible lesions (Dimagl, Iadecola et al. 1999).

The concept of prophylactic neuroprotection is based on experimental data in animal models demonstrating ischemic tolerance. Different mechanisms of cerebral ischemic tolerance have been identified: cytokines, inflammatory pathways, free radicals, NO, ATP-dependent potassium channels, adenosine. The inventive compounds thus have the advantage of playing a neuroprotective role.

Finally, the compounds according to the invention are of particular interest in the treatment of inflammatory disorders, in particular in the treatment of asthma. In fact, the prevalence of allergic disorders, particularly asthma, has risen steadily in industrialized countries and represents a major public health concern. Regardless of the causal mechanism, the common feature of allergic disorders is an inflammatory reaction initiated by antigen-presenting dendritic cells. The inventors have shown that the inventive compounds interfere with the differentiation and maturation of said dendritic cells and inhibit the migration thereof to secondary lymphoid organs. Also, it has been shown that the inventive compounds are weaker inducers of the proliferation of naive CD4+ T cells.

The compounds according to the invention therefore interfere with the initiation of the immune response and thus represent an advantageous therapeutic tool for the treatment of asthma.

The invention relates to novel substituted 1,3-diphenyl-prop-2-en-1-one derivatives, pharmaceutical and/or cosmetic compositions comprising same, the therapeutic and/or cosmetic uses thereof, particularly in the fields of human and animal health. The invention also relates to a method of preparation of said derivatives.

The inventors have shown, in a surprising manner, that the compounds according to the invention exhibit PPAR agonist activity and antioxidant properties. The inventive compounds can therefore interfere with at least two signal transduction pathways that are activated in particular during inflammation: cytokine production and free radical production. By acting synergistically, the inventive compounds represent an advantageous therapeutic and/or cosmetic means for the treatment of cardiovascular diseases, pathologies associated with syndrome X, dyslipidemias, diabetes, obesity, hypertension, inflammatory diseases, dermatological diseases (psoriasis, atopic dermatitis, acne, etc.), asthma, disorders linked to oxidative stress, ageing in general, for example skin ageing, particularly in the cosmetic field (appearance of wrinkles, etc.).

Moreover, the compounds according to the invention are capable of exerting a prophylactic activity in terms of neuroprotection, and also of providing an active neuroprotection in the acute phase of cerebral ischemia.

Lastly, the compounds according to the invention represent an advantageous therapeutic tool for the prevention and/or treatment of several cardiovascular risk factors related to deregulations of lipid and/or glucose metabolism (hyperlipidemia, diabetes, obesity, etc.). They enable a reduction in the global risk.

The present invention is therefore directed at providing novel substituted 1,3-diphenylprop-2-en-1-one derivatives having an improved formula and a satisfactory therapeutic efficacy.

These and other objectives are attained by the invention which in particular has as object substituted 1,3-diphenyl-prop-2-en-1-one derivatives represented by general formula (I) below:

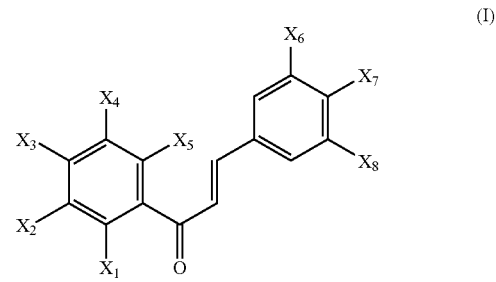

in which:

$X_7$ represents a group corresponding to the following formula: $G_7$-$R_7$ in which $G_7$ is an oxygen or sulfur atom and $R_7$ is an alkyl chain such as defined hereinbelow, substituted by a substituent from group 1 or a substituent from group 2, optionally $R_7$ can also be substituted by an aryl group, the substituents from group 1 are selected in the group consisting of carboxy groups having the formula: —COOR$_a$, carbamoyl groups having the formula: —CONR$_b$R$_c$ or the tetrazolyl group, the substituents from group 2 are selected in the group consisting of sulfonic acid (—SO$_3$H) and sulfonamide groups having the formula: —SO$_2$NR$_b$R$_c$, with R$_a$, R$_b$ and R$_c$, which are the same or different, representing a hydrogen atom or an alkyl group substituted or not, the $X_i$ groups with i=1, 2, 3, 4 or 5, which are the same or different, represent a halogen atom or a thionitroso group or respectively correspond to the formula $(G_i\text{-}R_i)_n\text{-}G'_i\text{-}R'_i$ in which:

n can have the values 0 or 1, $G_i$ and $G'_i$, which are the same or different, represent a single bond, an oxygen atom or a sulfur atom, $R_i$ and $R'_i$, which are the same or different, represent an alkyl, alkenyl, aryl group or a heterocycle, $R'_i$ can also represent a hydrogen atom, the $X_i$ groups with i=6 or i=8, which are the same or different, represent a halogen atom or correspond to the formula $G'_i$-$R'_i$, $G'_i$ and $R'_i$ being such as defined hereinabove, $X_6$ and $X_8$ not simultaneously representing a hydrogen atom, Xi with i=1, 2, 3, 4, 5, 6 or 8 cannot represent a heterocycle directly bound to the aromatic ring of the 1,3-diphenyl prop-2-en-1-one, with the exception of compounds represented by formula (I) in which simultaneously:

one of the groups $X_1$, $X_2$, $X_3$, $X_4$ or $X_5$ is a hydroxyl group, $G_7$ is an oxygen atom, and one of the groups $X_6$ or $X_8$ is a hydrogen atom or a halogen or a hydroxyl or an alkyloxy group, with the exception of compounds represented by formula (I) in which simultaneously:

the $X_1$, $X_2$ and $X_4$ groups simultaneously represent a hydrogen atom, the $X_6$ and $X_8$ groups represent $G'_i R'_i$, the $X_5$ group represents a thionitroso group or a $G'_i R'_i$ group, the $X_3$ group represents a halogen or a $G'_i R'_i$ group, in which $G'_i$ represents an oxygen atom, a sulfur atom or a single bond and $R'_i$ represents a saturated, linear, branched or cyclic alkyl group, halogenated or not, or a hydrogen atom.

According to a particular embodiment, the compounds represented by formula (I) are such as defined hereinabove and exclude compounds represented by formula (I) in which simultaneously:

the $X_1$, $X_2$ and $X_4$ groups simultaneously represent a hydrogen atom, and one of the groups $X_3$ or $X_5$ represents a hydrogen atom or a halogen or an alkyl group or an alkyloxy group or an alkylthio group or a hydroxyl group or a thiol group or a thionitroso group.

In a preferred manner, a particular object of the invention relates to compounds represented by general formula (Ia) which correspond to compounds having general formula (I) in which $X_1$ and $X_5$ are hydrogen atoms.

In a preferred manner, a particular object of the invention relates to compounds represented by general formula (Ib) which correspond to compounds having general formula (I) in which $X_2$ and $X_4$ are alkyl groups and more advantageously in which $X_1$ and $X_5$ are hydrogen atoms.

A particular object of the invention relates to compounds represented by general formula (Ic) which correspond to compounds having general formula (I) in which $X_1$, $X_3$ and $X_4$ are alkyl groups.

Another particular object of the invention relates to compounds represented by general formula (Id) which correspond to compounds having general formula (I) in which $X_1$, $X_2$, $X_4$ and $X_5$ are hydrogen atoms.

Another particular object of the invention relates to compounds represented by general formula (II) which correspond to compounds having general formula (I) in which $X_6$ and $X_8$ are alkyl groups.

Even more preferably, the compounds represented by general formula (II) are those in which $X_1$ and $X_5$ are hydrogen atoms and advantageously in which $X_2$ and $X_4$ are alkyl groups.

Another particular object of the invention relates to compounds represented by general formula (II) in which $X_1$, $X_3$, $X_4$, $X_6$ and $X_8$ are alkyl groups.

Another particular object of the invention relates to compounds represented by general formula (II) in which $X_6$ and $X_8$ are alkyl groups and $X_1$, $X_2$, $X_4$ and $X_5$ are hydrogen atoms.

According to a particular aspect of the invention, the compounds represented by formula (I) are such as defined hereinabove with $X_3$ which represents a halogen atom or a thionitroso group or corresponds to the formula $(G_i\text{-}R_i)_n\text{-}G'_i\text{-}R'_i$ such as defined earlier, in which $G'_i$ represents an oxygen atom or a sulfur atom.

The invention also includes the optical and geometric isomers, racemates, tautomers, salts, hydrates and mixtures of the inventive compounds.

The invention also encompasses the prodrugs of the inventive compounds which, after administration to a subject, are converted to inventive compounds and/or to metabolites of inventive compounds which display similar therapeutic activity to the inventive compounds.

In a preferred manner, at least one of the groups Gi or G'i represents a sulfur atom with i adopting one of the values 1, 2, 3, 4, 5, 6, 7 or 8.

In the scope of the invention, the derivatives according to the invention such as described hereinabove can adopt the cis or trans conformation.

According to the invention, the term "alkyl" designates a saturated hydrocarbon function, linear, branched or cyclic, halogenated or not, having more particularly from 1 to 24, preferably 1 to 10, carbon atoms such as methyl, ethyl, propyl, isopropyl, n-butyl, isobutyl, tert-butyl, pentyl, neopentyl, n-hexyl or cyclohexyl. Groups containing one or two carbon atoms or containing from two to seven carbon atoms are particularly preferred. Methyl and ethyl groups are quite particularly preferred.

According to the invention, the term "alkenyl" denotes an unsaturated hydrocarbon function, linear, branched or cyclic, halogenated or not, having more particularly from 1 to 24, preferably 1 to 10, carbon atoms.

According to the invention, the term "alkyl" denotes an aromatic hydrocarbon group, substituted or not, in particular substituted by at least one halogen atom, an alkyl, hydroxyl, thiol, alkyloxy, alkylthio, oxime or thionitroso group. Phenyl groups are quite particularly preferred.

According to the invention, the term "heterocycle" designates a cyclic group, saturated or unsaturated or aromatic comprising one or more heteroatoms, such as nitrogen, sulfur and oxygen. They can be substituted, advantageously by at least one alkyl group such as defined hereinabove. Heterocycles such as dithiolanes, pyridine, furan, thiophene or morpholine are particularly preferred. In the context of the invention, the heterocycles piperidine and piperazine are advantageously substituted by at least one alkyl group such as defined hereinabove.

The term thionitroso refers to a nitroso group bound to the aromatic ring through a sulfur atom.

The term alkyloxy designates an alkyl chain bound to the ring by an oxygen atom. The alkyl chain is defined earlier.

The term alkylthio refers to an alkyl chain bound to the aromatic ring by a sulfur atom (thioether bond). The alkyl chain is defined earlier.

The term halogen represents a chlorine, bromine, iodine or fluorine atom.

According to a particular embodiment of the invention, preferred compounds are indicated below with their corresponding formulas:

1-(4-((R,S)-5-[1,2]dithiolan-3-ylpentyloxy)-3,5-dimethylphenyl)-3-(4-carboxydimethylmethyloxy-3,5-dimethylphenyl)prop-2-en-1-one:

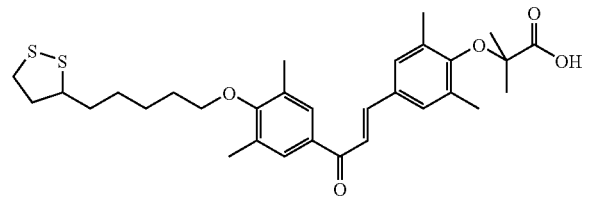

1-(4-Mercapto-3,5-dimethylphenyl)-3-(4-carboxydimethylmethyloxy-3,5-dimethylphenyl)prop-2-en-1-one:

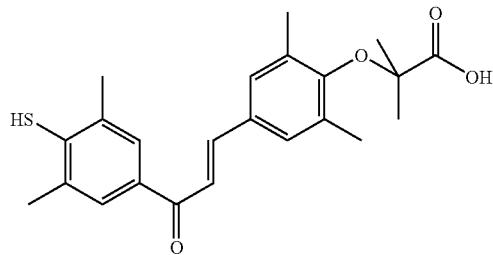

1-(4-Cyclohexylethylthio-3,5-dimethylphenyl)-3-(4-carboxydimethylmethyloxy-3,5-dimethylphenyl)prop-2-en-1-one:

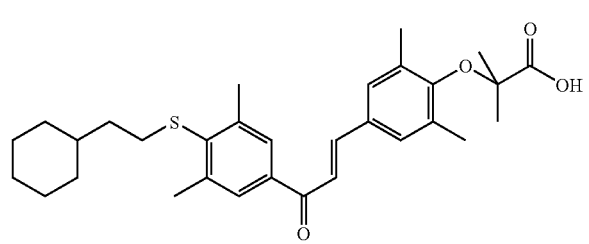

1-(2,5-Dihydroxy-3,4,6-trimethylphenyl)-3-(4-carboxydimethylmethyloxy-3,5-dimethylphenyl)prop-2-en-1-one:

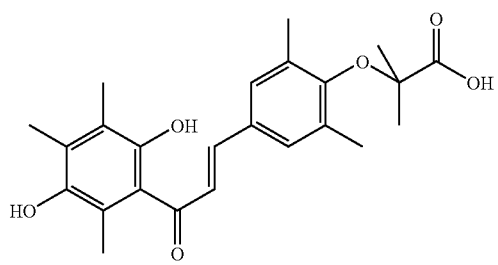

1-(2,5-Dimethoxy-3,4,6-trimethylphenyl)-3-(4-carboxydimethylmethoxy-3,5-dimethylphenyl)prop-2-en-1-one:

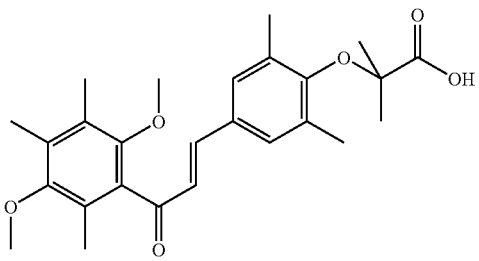

1-(2,5-Dihydroxyphenyl)-3-(4-carboxydimethylmethyloxy-3,5-dimethylphenyl)prop-2-en-1-one:

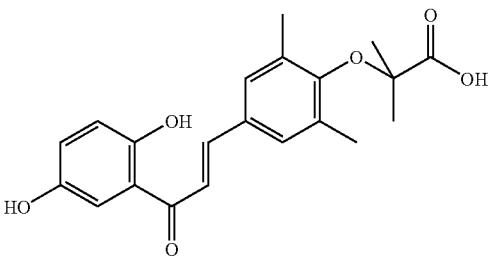

1-(2,5-Dimethoxyphenyl)-3-(4-carboxydimethylmethyloxy-3,5-dimethylphenyl)prop-2-en-1-one:

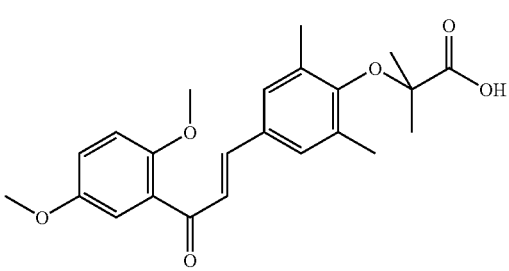

1-(4-Phenylethyloxyphenyl)-3-(4-carboxydimethylmethyloxy-3,5-dimethylphenyl)prop-2-en-1-one:

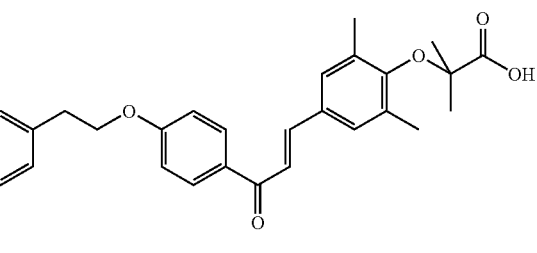

1-(4-(Morpholin-4-ylethyloxy)phenyl)-3-(4-carboxydimethylmethyloxy-3,5-dimethylphenyl)prop-2-en-1-one:

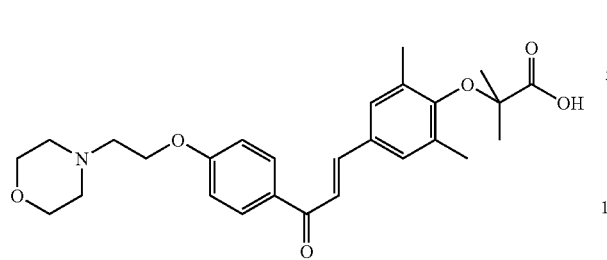

1-(4-(Pentylthioethyloxy)phenyl)-3-(4-tert-butyloxycarbonyldimethylmethyloxy-3,5-dimethylphenyl)prop-2-en-1-one:

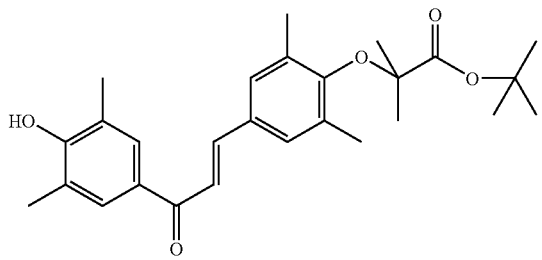

1-(4-Hydroxy-3,5-dimethylphenyl)-3-(4-carboxydimethylmethyloxy-3,5-dimethylphenyl)prop-2-ene-1-one:

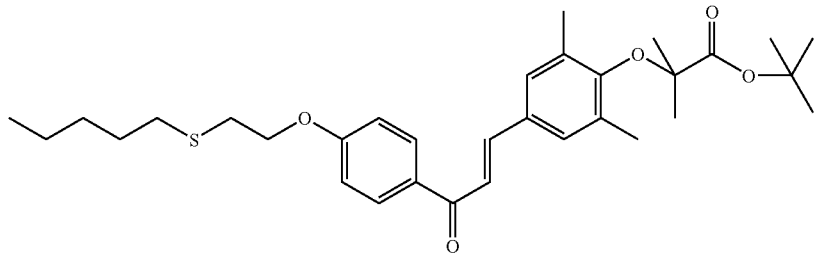

1-(4-(Pentylthioethyloxy)phenyl)-3-(4-carboxydimethylmethyloxy-3,5-dimethylphenyl)prop-2-en-1-one:

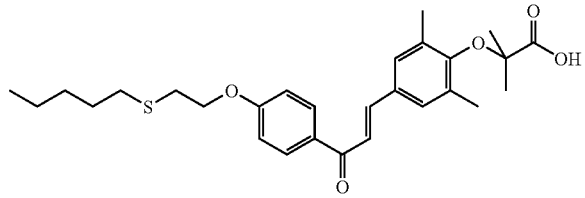

1-(4-Hydroxy-3,5-dimethylphenyl)-3-(4-tert-butyloxycarbonyldimethylmethyloxy-3,5-dimethylphenyl)prop-2-ene-1-one:

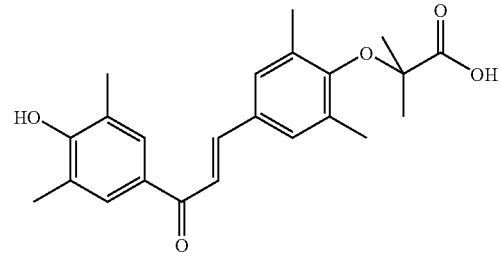

1-(4-((R,S)-5-[1,2]dithiolan-3-ylpentyloxy)phenyl)-3-(4-tert-butyloxycarbonyldimethylmethyloxy-3,5-dimethylphenyl)prop-2-en-1-one:

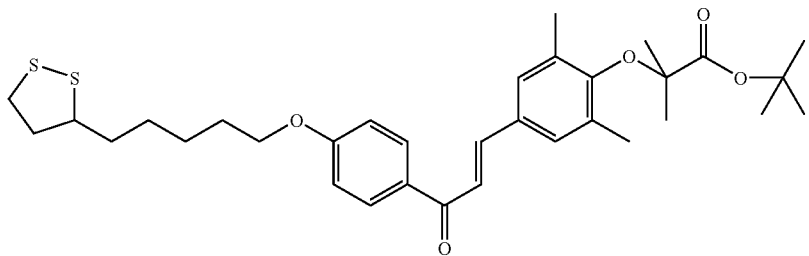

1-(4-((R,S)-5-[1,2]dithiolan-3-ylpentyloxy)phenyl)-3-(4-carboxydimethylmethyloxy-3,5-dimethylphenyl)prop-2-en-1-one:

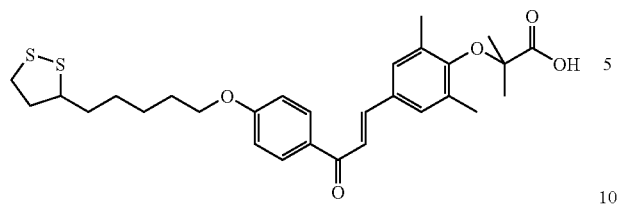

1-(4-Methylthiophenyl)-3-(4-tert-butyloxycarbonyldimethylmethyloxy-3,5-dibromophenyl)prop-2-ene-1-one:

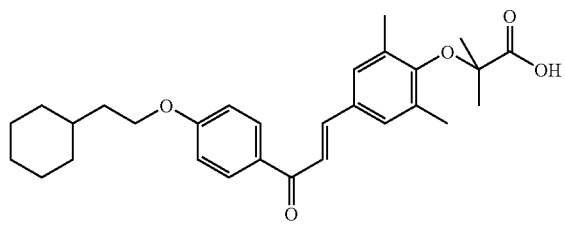

1-(4-Methylthio-3,5-dimethylphenyl)-3-(4-tert-butyloxycarbonyldimethylmethyloxy-3,5-dimethylphenyl)prop-2-en-1-one:

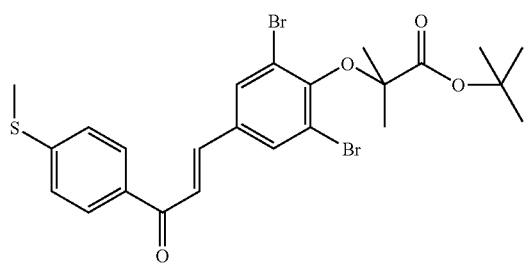

1-(4-Methylthiophenyl)-3-(4-carboxydimethylmethyloxy-3,5-dibromophenyl)prop-2-ene-1-one:

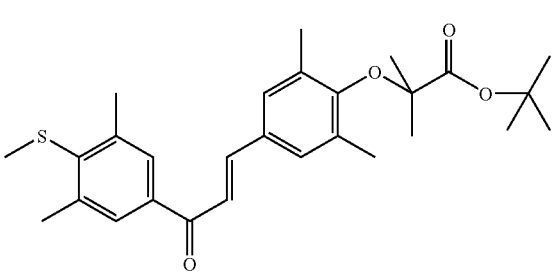

1-(4-Methylthio-3,5-dimethylphenyl)-3-(4-carboxydimethylmethyloxy-3,5-dimethylphenyl)prop-2-en-1-one:

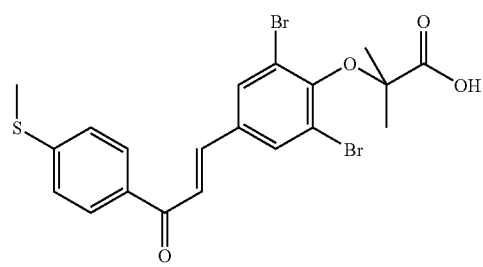

1-(4-Cyclohexylethyloxyphenyl)-3-(4-tert-butyloxycarbonyldimethylmethyloxy-3,5-dimethylphenyl)prop-2-en-1-one:

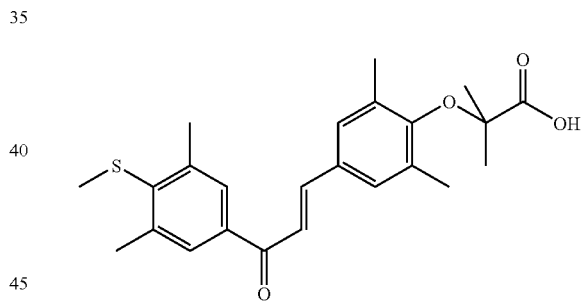

1-(4-Propyloxy-3,5-dimethylphenyl)-3-(4-tert-butyloxycarbonyldimethylmethyloxy-3,5-dimethylphenyl)prop-2-en-1-one:

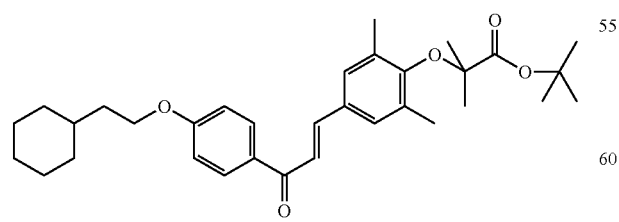

1-(4-Cyclohexylethyloxyphenyl)-3-(4-carboxydimethylmethyloxy-3,5-dimethylphenyl)prop-2-en-1-one:

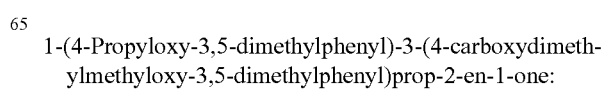

1-(4-Propyloxy-3,5-dimethylphenyl)-3-(4-carboxydimethylmethyloxy-3,5-dimethylphenyl)prop-2-en-1-one:

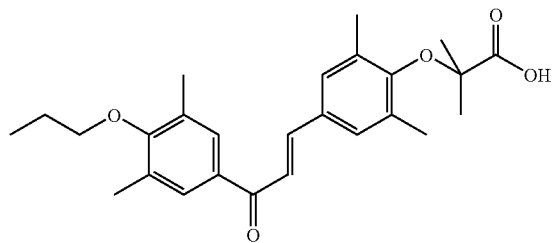

1-(4-Methoxy-3,5-dimethylphenyl)-3-(4-tert-butyloxycarbonyldimethylmethyloxy-3,5-dimethylphenyl)prop-2-en-1-one:

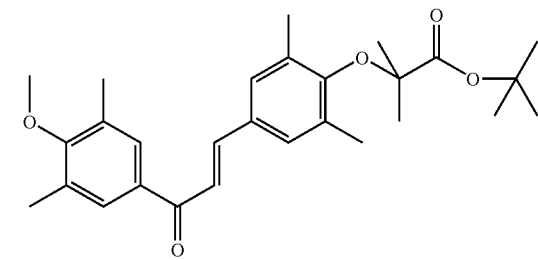

1-(4-Methoxy-3,5-dimethylphenyl)-3-(4-carboxydimethylmethyloxy-3,5-dimethylphenyl)prop-2-en-1-one:

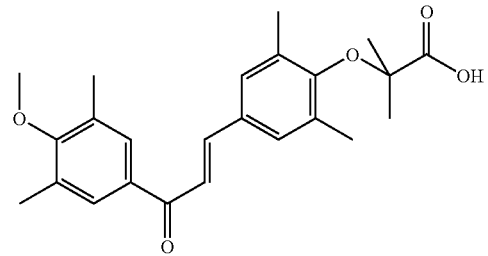

1-(4-Hexyloxy-3,5-dimethylphenyl)-3-(4-tert-butyloxycarbonyldimethylmethyloxy-3,5-dimethylphenyl)prop-2-en-1-one:

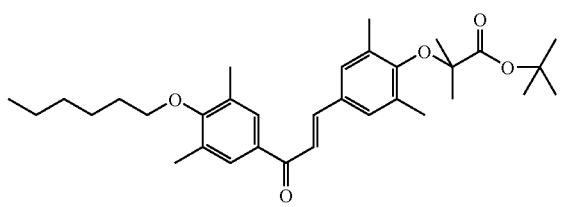

1-(4-Hexyloxy-3,5-dimethylphenyl)-3-(4-carboxydimethylmethyloxy-3,5-dimethylphenyl)prop-2-en-1-one:

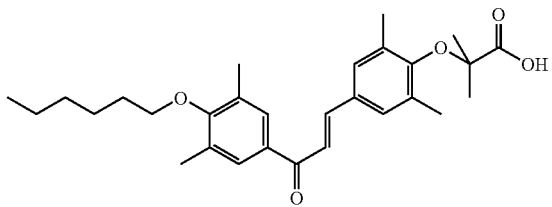

1-(4-Cyclohexylethyloxy-3,5-dimethylphenyl)-3-(4-tert-butyloxycarbonyldimethylmethyloxy-3,5-dimethylphenyl)prop-2-en-1-one:

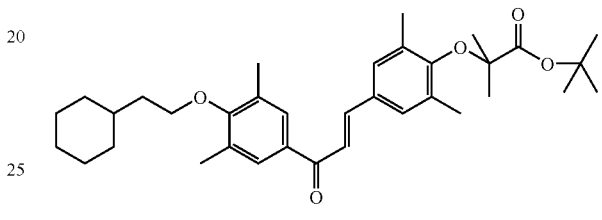

1-(4-Cyclohexylethyloxy-3,5-dimethylphenyl)-3-(4-carboxydimethylmethyloxy-3,5-dimethylphenyl)prop-2-en-1-one:

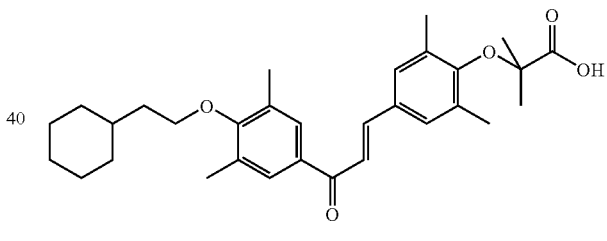

1-(4-Cyclohexylthioethyloxyphenyl)-3-(4-tert-butyloxycarbonyldimethylmethyloxy-3,5-dimethylphenyl)prop-2-en-1-one:

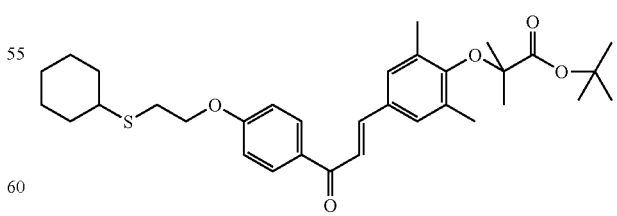

1-(4-Cyclohexylthioethyloxyphenyl)-3-(4-carboxydimethylmethyloxy-3,5-dimethylphenyl)prop-2-en-1-one:

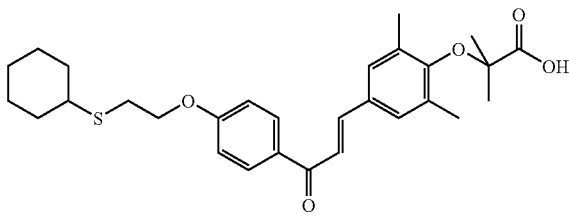

1-(2,4,5-Trimethylphenyl)-3-(4-tert-butyloxycarbonyldimethylmethyloxy-3,5-dimethylphenyl)prop-2-en-1-one:

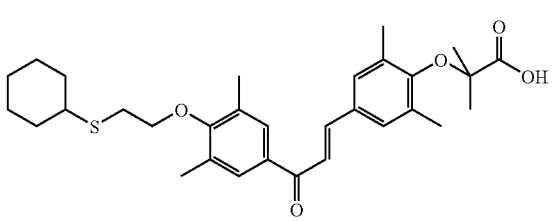

1-(4-Methylthiophenyl)-3-(4-tert-butyloxycarbonyldimethylmethyloxy-3-fluorophenyl)prop-2-en-1-one:

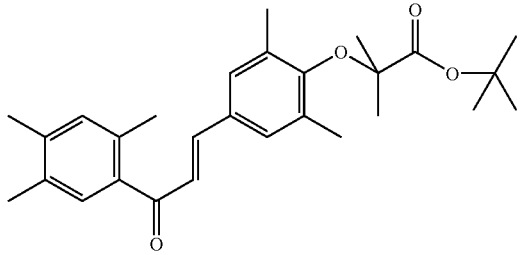

1-(2,4,5-Trimethylphenyl)-3-(4-carboxydimethylmethyloxy-3,5-dimethylphenyl)prop-2-en-1-one:

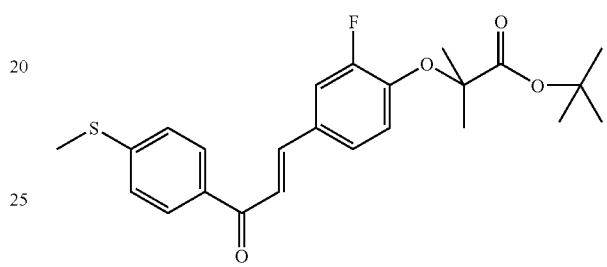

1-(4-Methylthiophenyl)-3-(4-carboxydimethylmethyloxy-3-fluorophenyl)prop-2-en-1-one:

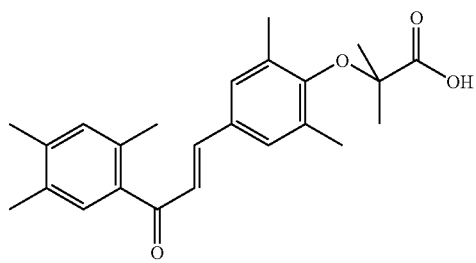

1-(4-Cyclohexylthioethyloxy-3,5-dimethylphenyl)-3-(4-tert-butyloxycarbonyldimethylmethyloxy-3,5-dimethylphenyl)prop-2-en-1-one:

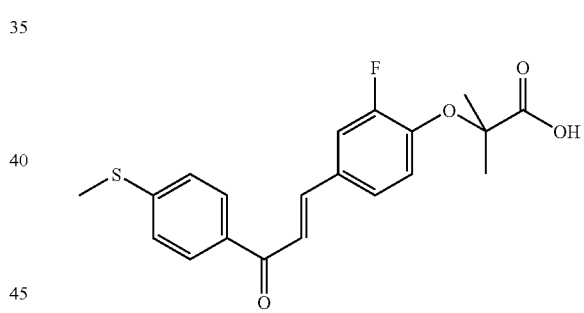

1-(2,3,4,5,6-Pentamethylphenyl)-3-(4-tert-butyloxycarbonyldimethylmethyloxy-3,5-dimethylphenyl)prop-2-en-1-one:

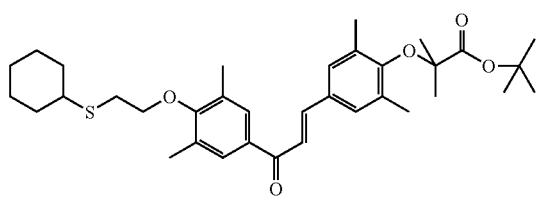

1-(4-Cyclohexylthioethyloxy-3,5-dimethylphenyl)-3-(4-carboxydimethylmethyloxy-3,5-dimethylphenyl)prop-2-en-1-one:

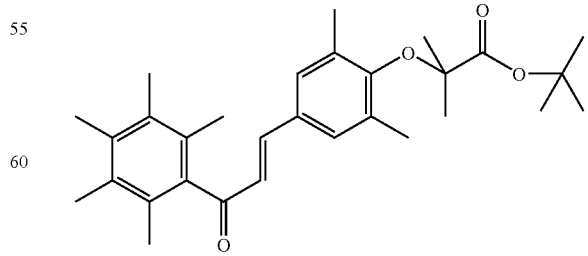

1-(2,3,4,5,6-Pentamethylphenyl)-3-(4-carboxydimethylmethyloxy-3,5-dimethylphenyl)prop-2-en-1-one:

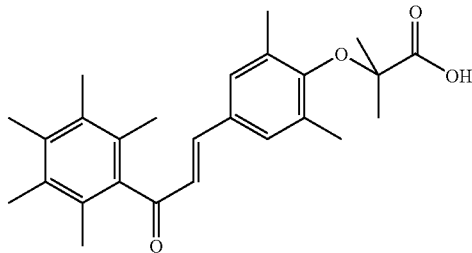

1-(4-Phenyloxyphenyl)-3-(4-tert-butyloxycarbonyldimethylmethyloxy-3,5-dimethylphenyl)prop-2-en-1-one:

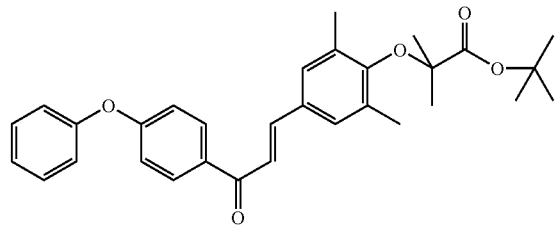

1-(4-Phenyloxyphenyl)-3-(4-carboxydimethylmethyloxy-3,5-dimethylphenyl)prop-2-en-1-one

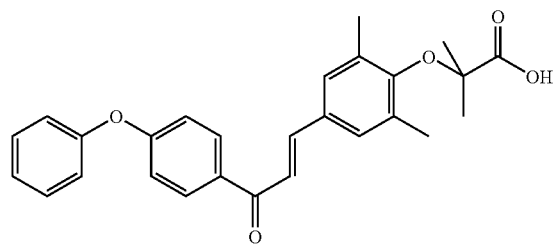

1-(4-Methoxy-3-fluorophenyl)-3-(4-tert-butyloxycarbonyldimethylmethyloxy-3,5-dimethylphenyl)prop-2-en-1-one:

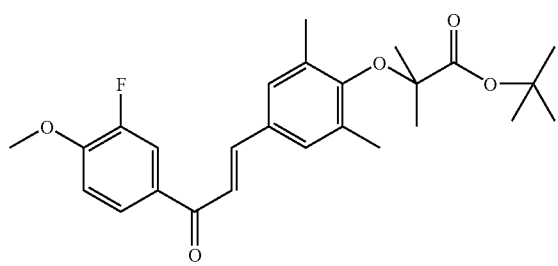

1-(4-Methoxy-3-fluorophenyl)-3-(4-carboxydimethylmethyloxy-3,5-dimethylphenyl)prop-2-en-1-one:

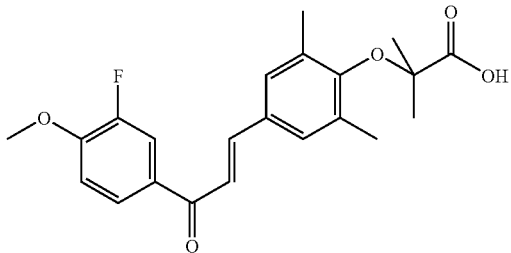

1-(4-Methoxy-3-methylphenyl)-3-(4-tert-butyloxycarbonyldimethylmethyloxy-3,5-dimethylphenyl)prop-2-en-1-one:

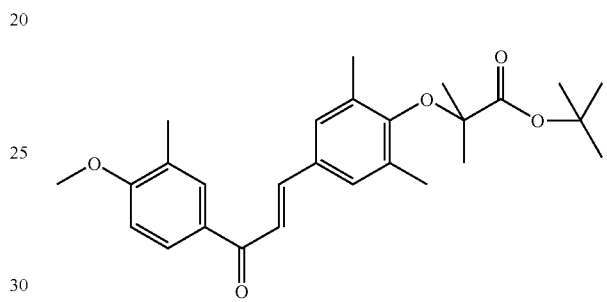

1-(4-Methoxy-3-methylphenyl)-3-(4-carboxydimethylmethyloxy-3,5-dimethylphenyl)prop-2-en-1-one:

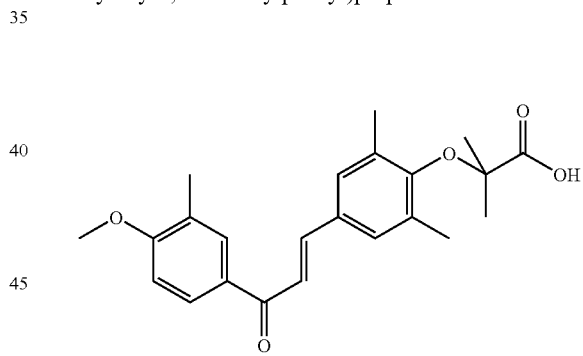

1-(4-Hexylthio-3,5-dimethylphenyl)-3-(4-tert-butyloxycarbonyldimethylmethyloxy-3,5-dimethylphenyl)prop-2-en-1-one:

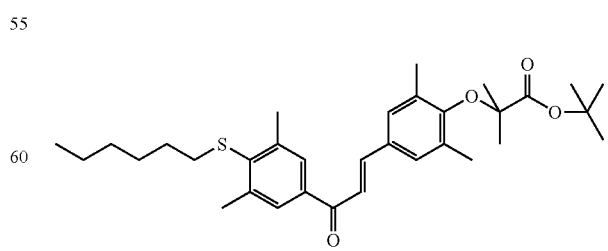

1-(4-Hexylthio-3,5-dimethylphenyl)-3-(4-carboxydimethylmethyloxy-3,5-dimethylphenyl)prop-2-en-1-one:

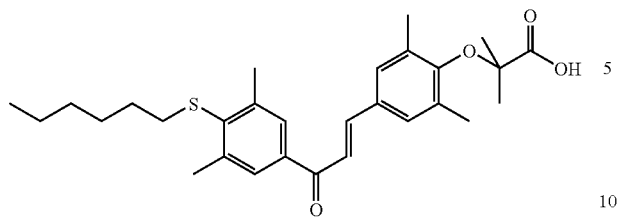

1-(2,5-Dimethoxyphenyl)-3-(4-tert-butyloxycarbonyldimethylmethyloxy-3,5-dimethylphenyl)prop-2-en-1-one:

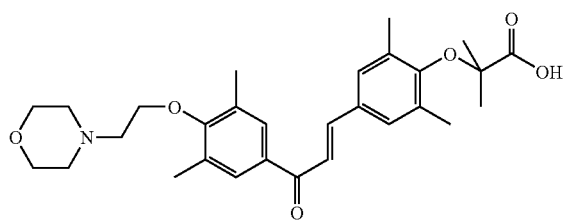

1-(4-Bromophenyl)-3-(4-tert-butyloxycarbonyldimethylmethyloxy-3,5-difluorophenyl)prop-2-en-1-one:

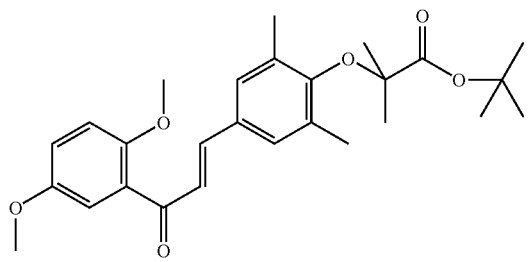

1-(2,5-Dimethoxyphenyl)-3-(4-carboxydimethylmethyloxy-3,5-dimethylphenyl)prop-2-en-1-one:

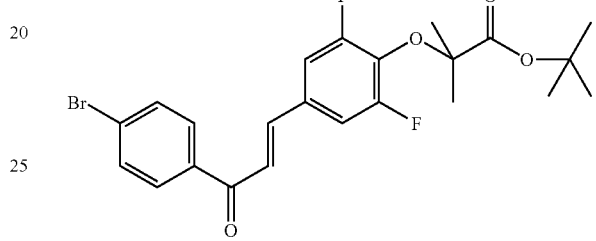

1-(4-Bromophenyl)-3-(4-carboxydimethylmethyloxy-3,5-difluorophenyl)prop-2-en-1-one:

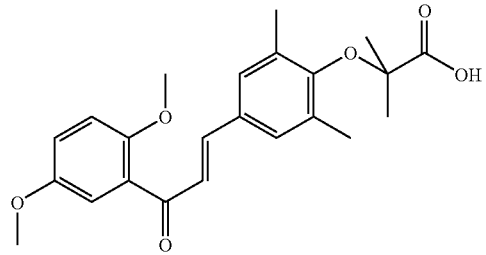

1-(3,5-Dimethyl-4-(morpholin-4-ylethyloxy)phenyl)-3-(4-ethyloxycarbonyldimethylmethyloxy-3,5-dimethylphenyl)prop-2-en-1-one hydrochloride:

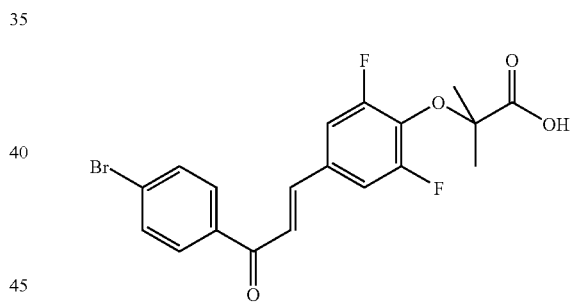

1-(4-Methoxy-3-trifluoromethylphenyl)-3-(4-tert-butyloxycarbonyldimethylmethyloxy-3,5-dimethylphenyl)prop-2-en-1-one:

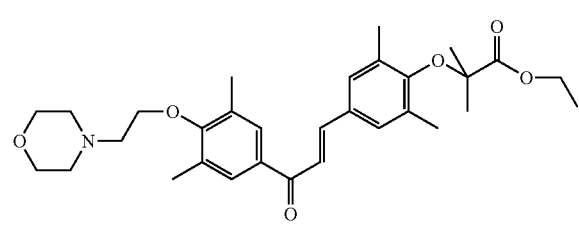

1-(3,5-Dimethyl-4-(morpholin-4-ylethyloxy)phenyl)-3-(4-carboxydimethylmethyloxy-3,5-dimethylphenyl)prop-2-en-1-one:

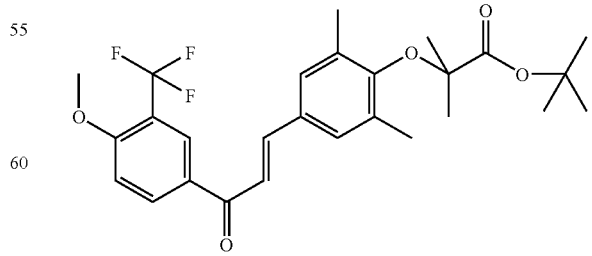

1-(4-Methoxy-3-trifluoromethylphenyl)-3-(4-carboxydimethylmethyloxy-3,5-dimethylphenyl)prop-2-en-1-one:

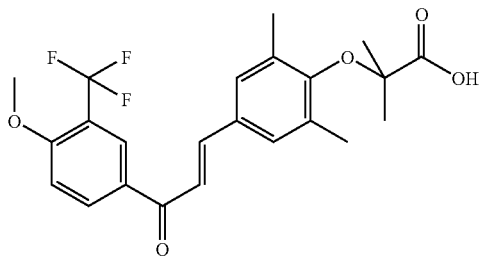

The invention also has as object a method for preparing compounds represented by formula (I).

Said method of preparation has many advantages. It is simple to carry out on an industrial scale and affords a high yield of compounds represented by formula (I).

The method according to the invention comprises contacting in basic medium or in acidic medium at least one compound represented by formula (A) with at least one compound represented by formula (B), formulas (A) and (B) being:

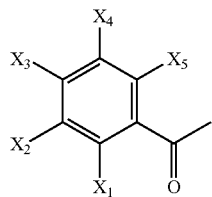

(A)

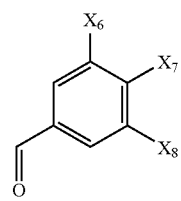

(B)

formulas in which $X_1$, $X_2$, $X_3$, $X_4$, $X_5$, $X_6$, $X_7$ et $X_8$ are such as defined hereinabove, $X_7$ can also represent a hydroxyl or thiol group. The conditions for carrying out said reaction in acidic or basic medium are within reach of those skilled in the art and wide variations are possible.

Said two compounds are advantageously contacted in stoichiometric proportions. Contact is preferably done at room temperature (between approximately 18° C. and 25° C.) and at atmospheric pressure.

In basic medium, the reaction is preferably carried out in the presence of a strong base, such as an alkaline metal hydroxide, like sodium hydroxide or an alkaline metal alcoholate like sodium ethylate.

In acidic medium, the reaction is preferably carried out in the presence of a strong acid, such as hydrochloric acid.

The reaction scheme can be depicted as follows:

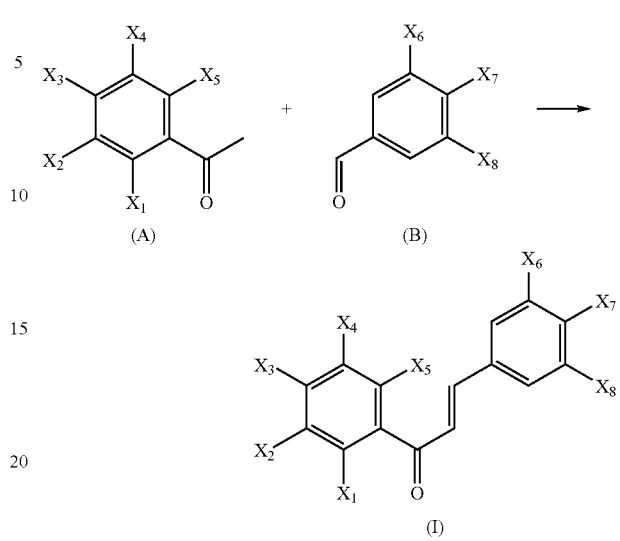

The synthesis in basic medium can be carried out in the following manner:

One molar equivalent of ketone (compound (A)) and one molar equivalent of aldehyde (compound (B)) are solubilized in a hydroalcoholic solution of 20 molar equivalents of sodium hydroxide. The mixture is stirred for approximately 18 hours at room temperature (between 18° C. and 25° C.). The medium is then acidified (in particular to a pH of approximately 2) in particular with hydrochloric acid.

The expected substituted 1,3-diphenylprop-2-en-1-one can be obtained by precipitation or solid/liquid extraction after evaporation of the reaction medium. It can then be purified by silica gel chromatography or by crystallization.

The synthesis in acidic medium can be carried out in the following manner:

One molar equivalent of ketone (compound (A)) and one molar equivalent of aldehyde (compound (B)) are solubilized in an ethanol solution saturated with gaseous hydrochloric acid. The mixture is stirred at room temperature for approximately 6 hours, the solvent is eliminated, in particular by vacuum evaporation. The substituted 1,3-diphenylprop-2-en-1-one is purified, in particular by chromatography on silica gel.

The method for preparing compounds represented by formula (I) allows the preparation of compounds referred to hereinbelow as intermediate compounds. The invention also has as object certain starting materials and intermediate compounds obtained as provided for in the invention.

Said intermediate compounds are more particularly selected in the group consisting of:
  1-(4-(Pentylthioethyloxy)phenyl)-3-(4-hydroxy-3,5-dimethylphenyl)prop-2-en-1-one;
  1-(4-((R,S)-5-[1,2]dithiolan-3-ylpentyloxy)phenyl)-3-(4-hydroxy-3,5-dimethylphenyl)prop-2-en-1-one;
  1-(4-Methylthiophenyl)-3-(4-hydroxy-3,5-dibromophenyl)prop-2-en-1-one;
  1-(4-(Cyclohexylethyloxy)phenyl)-3-(4-hydroxy-3,5-dimethylphenyl)prop-2-en-1-one;
  1-(4-Methylthio-3,5-dimethylphenyl)-3-(4-hydroxy-3,5-dimethylphenyl)prop-2-en-1-one;

1-(4-Methoxy-3,5-dimethylphenyl)-3-(4-hydroxy-3,5-dimethylphenyl)prop-2-en-1-one;

1-(4-(Cyclohexylethyloxy)-3,5-dimethylphenyl)-3-(4-hydroxy-3,5-dimethylphenyl)prop-2-en-1-one;

1-(4-(Cyclohexylthioethyloxy)phenyl)-3-(4-hydroxy-3,5-dimethylphenyl)prop-2-en-1-one;

1-(2,4,5-Trimethylphenyl)-3-(4-hydroxy-3,5-dimethylphenyl)prop-2-en-1-one;

1-(4-(Cyclohexylthioethyloxy)-3,5-dimethylphenyl)-3-(4-hydroxy-3,5-dimethylphenyl)prop-2-en-1-one;

1-(4-Methylthiophenyl)-3-(4-hydroxy-3-fluorophenyl)prop-2-en-1-one;

1-(2,3,4,5,6-Pentamethylphenyl)-3-(4-hydroxy-3,5-dimethylphenyl)prop-2-en-1-one;

1-(4-Phenoxyphenyl)-3-(4-hydroxy-3,5-dimethylphenyl)prop-2-en-1-one;

1-(4-Methoxy-3-fluorophenyl)-3-(4-hydroxy-3,5-dimethylphenyl)prop-2-en-1-one;

1-(4-Methoxy-3-methylphenyl)-3-(4-hydroxy-3,5-dimethylphenyl)prop-2-en-1-one;

1-(4-Hexylthio-3,5-dimethylphenyl)-3-(4-hydroxy-3,5-dimethylphenyl)prop-2-en-1-one;

1-(2,5-Dimethoxyphenyl)-3-(4-hydroxy-3,5-dimethylphenyl)prop-2-en-1-one;

1-(4-Bromophenyl)-3-(4-hydroxy-3,5-difluorophenyl)prop-2-en-1-one;

1-(4-Methoxy-3-trifluoromethylphenyl)-3-(4-hydroxy-3,5-dimethylphenyl)prop-2-en-1-one.

The invention also has as object compounds represented by general formula (I) such as described hereinabove, as medicaments.

Another object of the invention concerns a pharmaceutical and/or cosmetic composition comprising at least one compound represented by general formula (I) such as defined hereinabove, in a pharmaceutically acceptable support, possibly in combination with another therapeutic and/or cosmetic active agent.

In an advantageous manner it is a pharmaceutical and/or cosmetic composition for the treatment of cardiovascular diseases, dyslipidemias, pathologies associated with syndrome X, diabetes, obesity, hypertension, inflammatory diseases, dermatologicalal diseases (psoriasis, atopic dermatitis, acne, etc.), asthma, disorders linked to oxidative stress, ageing in general and for example skin ageing particularly in the cosmetic field (appearance of wrinkles, etc.).

Furthermore, the pharmaceutical and/or cosmetic compositions according to the invention can exert a prophylactic activity in terms of neuroprotection, and also provide an active neuroprotection in the acute phase of cerebral ischemia. Advantageously it is a pharmaceutical and/or cosmetic composition for the prevention and/or treatment of the appearance of several cardiovascular risk factors related to deregulations of lipid and/or glucose metabolism (hyperlipidemia, diabetes, obesity, etc.) by ensuring a reduction in the global risk.

The invention also relates to the use of at least one compound represented by formula (I) for preparing a pharmaceutical and/or cosmetic composition for practicing a method of treatment or prophylaxis of the human or animal body.

The invention also relates to a method for treating pathologies related to lipid and/or glucose metabolism comprising administering to a subject, particularly human, an effective dose of a compound or pharmaceutical composition such as defined hereinabove.

The pharmaceutical compositions according to the invention advantageously comprise one or more pharmaceutically acceptable excipients or vehicles. Examples include saline, physiological, isotonic, buffered solutions and the like, compatible with pharmaceutical use and known to those skilled in the art. The compositions can contain one or more agents or vehicles selected in the group consisting of dispersants, solubilizers, stabilizers, preservatives, and the like. Agents or vehicles that can be used in the formulations (liquid and/or injectable and/or solid) are in particular methylcellulose, hydroxymethylcellulose, carboxymethylcellulose, polysorbate 80, mannitol, gelatin, lactose, plant oils, acacia, and the like. The compositions can be formulated as suspensions for injection, gels, oils, tablets, suppositories, powders, capsules, soft capsules, and the like, possibly by means of pharmaceutical forms or devices ensuring prolonged and/or delayed release. For this type of formulation, an agent such as cellulose, carbonates or starches is advantageously used.

The compounds or compositions according to the invention can be administered in different ways and in different forms. For instance, they can be administered by the oral or systemic route, such as for example by the intravenous, intramuscular, subcutaneous, transdermal, intra-arterial route, etc. For injections, the compounds are generally formulated as liquid suspensions, which can be injected through a syringe or by infusion, for example. It is understood that the injection rate and/or the injected dose can be adapted by those skilled in the art according to the patient, the pathology, the method of administration, etc. Typically, the compounds are administered at doses ranging from 1 µg to 2 g per administration, preferably from 0.1 mg to 1 g per administration. The administrations may be given daily or repeated several times a day, as the case may be. Moreover, the compositions according to the invention can additionally comprise other active ingredients or agents.

LEGENDS TO THE FIGURES

FIGS. 1a, 1b, 1c illustrate the antioxidant characteristics of inventive compound 2 (Cpd 2) tested at a concentration of $10^{-4}$M.

FIG. 1a shows the kinetics of conjugated diene formation over time. The lag phase was 120 minutes when LDL were incubated with copper alone as compared with 314 minutes when the medium also contained compound 2.

FIG. 1b illustrates the rate of diene formation, which was 1.8 nmol/min/mg of LDL in the presence of copper alone and only 0.1 nmol/min/mg of LDL when compound 2 was present in the medium.

FIG. 1c represents the maximum amount of conjugated dienes formed over time. Copper alone induced the formation of 372 nmol/mg of conjugated dienes, compared with 35 nmol/mg when the medium also contained compound 2, which corresponds to a 90% decrease in the amount of conjugated dienes formed.

FIGS. 2a, 2b, 2c illustrate the antioxidant characteristics of inventive compound 4 (Cpd 4), compound 6 (Cpd 6) and compound 8 (Cpd 8) tested at a concentration of $10^{-4}$M.

FIG. 2a shows the kinetics of conjugated diene formation. The lag phase was 132 minutes when LDL were incubated with copper alone as compared with 401, 205 and 169 minutes in the presence of compounds 4, 6 and 8, respectively.

FIG. 2b illustrates the rate of diene formation, which was 2.2 nmol/min/mg of LDL in the presence of copper alone. The presence of compounds 4, 6 and 8 slowed the rate of the diene oxidation reaction to 0.2 nmol/min/mg in the presence of compound 4 and 1.7 nmol/min/mg in the presence of compounds 6 or 8.

The total amount of dienes formed (FIG. 2c) was 511 nmol/mg of LDL in the presence of copper alone versus 138, 443 and 474 nmol/mg in the presence of compounds 4, 6 and 8, respectively.

FIG. 3a illustrates the antioxidant characteristics of inventive compound 11 (Cpd 11).

The antioxidant character of compound 11 was demonstrated for different concentrations comprised between $10^{-6}$ M and $3.5 \times 10^{-5}$ M.

In the absence of compound 11, the lag phase was 87.2 minutes. Starting at the $10^{-6}$ M concentration, the lag phase increased relative to the control to 101.5 minutes. The lag phase increased in a dose-related manner to reach a maximum of 210 minutes at the concentration of $3.3 \times 10^{-5}$ M.

FIGS. 4a, 4b, 4c illustrate the antioxidant characteristics of inventive compound 19 (Cpd 19) and compound 23 (Cpd 23) tested at a concentration of $10^{-4}$ M.

FIG. 4a shows the kinetics of conjugated diene formation.

Figure 2A:
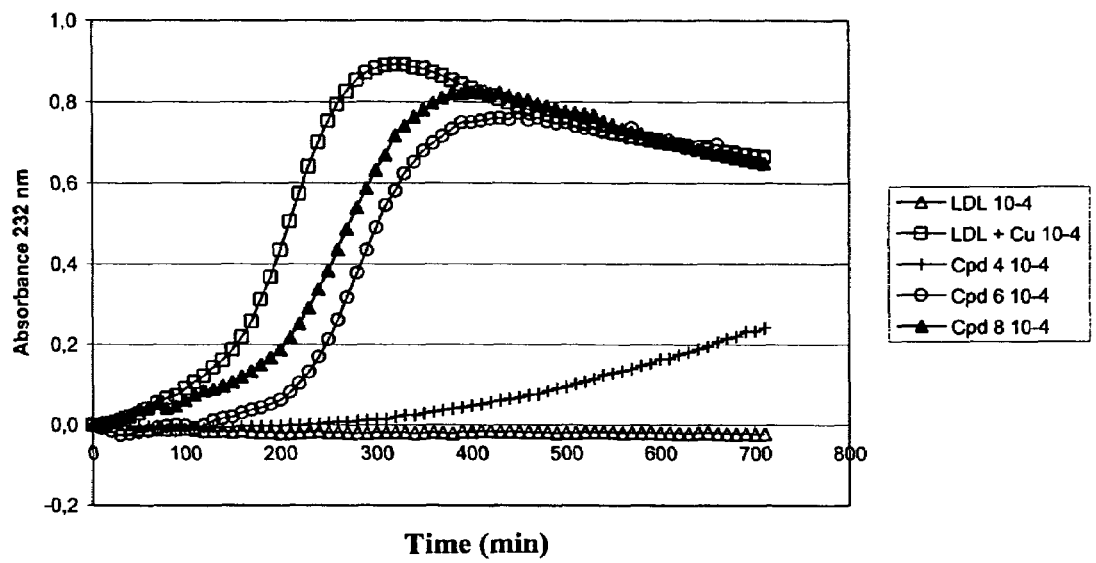
Figure 2B:
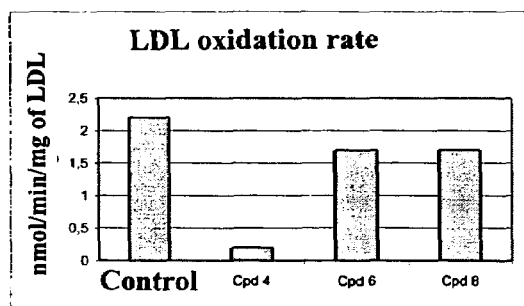
Figure 2C:
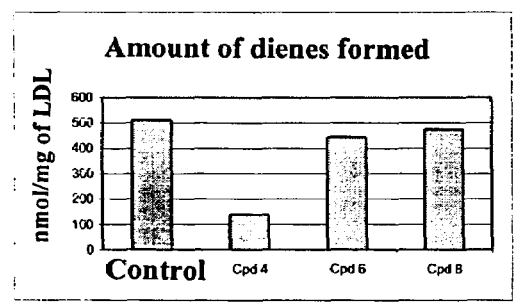
Figure 3A:
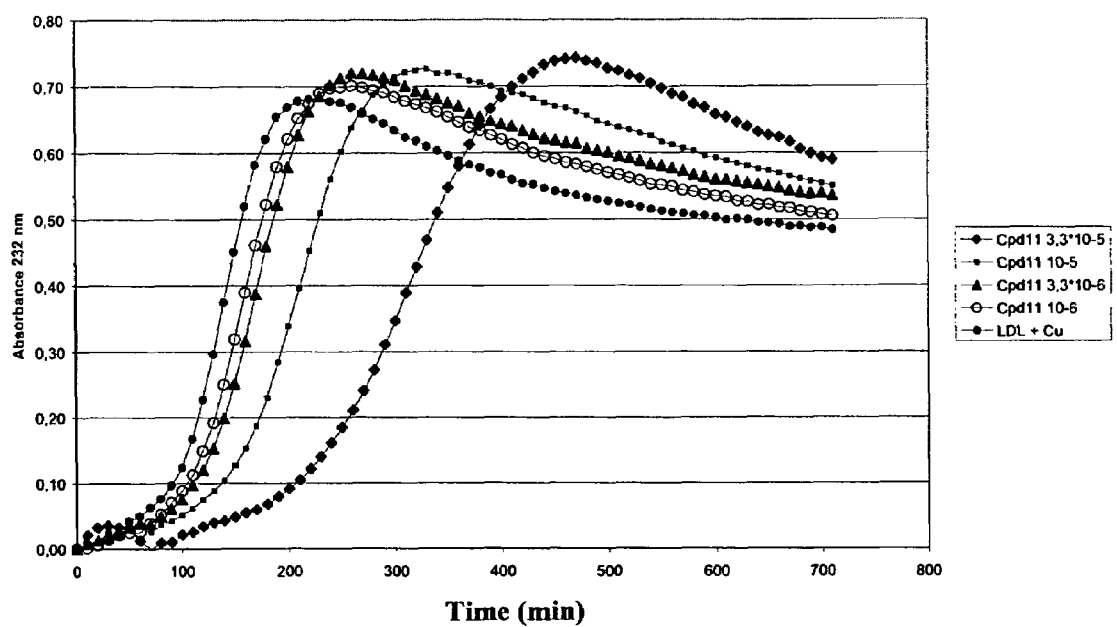

The lag phase was 61 minutes in the presence of copper alone as compared with 92.5 and 96.4 minutes in the presence of compounds 19 and 23, respectively.

The antioxidant character of compounds 19 and 23 was also manifested as a decrease in the rate of diene formation and by a decrease in the total amount of dienes formed.

In the absence of the compounds, the diene formation rate was 1.9 nmol/min/mg of LDL (FIG. 4b) as compared with 1.6 and 1.3 nmol/min/mg of LDL in the presence of compounds 19 and 23. In the absence of the compound, the total amount of dienes formed was 370.9 nmol/mg of LDL (FIG. 4c) versus 346.6 and 340.3 nmol/mg of LDL in the presence of compounds 19 and 23.

FIGS. 5a, 5b, 5c illustrate the antioxidant characteristics of inventive compound 25 (Cpd 25), compound 27 (Cpd 27), compound 29 (Cpd 29) and compound 31 (Cpd 31) tested at a concentration of $10^{-4}$ M.

FIG. 5a shows the kinetics of LDL oxidation in the presence of the different compounds, which increased in the presence of the different antioxidant compounds. It was 54.9 minutes in the presence of compound 29, increasing to 87.6 minutes with compound 25, 124.5 minutes with compound 31 and reaching 170.8 minutes in the presence of compound 27.

The antioxidant character of said compounds was also illustrated by the LDL oxidation rate (FIG. 5b) and by the total amount of dienes formed (FIG. 5c).

The LDL oxidation rate was 2 nmol/min/mg of LDL in the absence of the compounds (FIG. 5b). The compounds induced a decrease in the rate of oxidation to 1.6 nmol/min/mg in the presence of compound 25 and 1.4 nmol/min/mg with compound 31. The oxidation rate was minimal with compound 27 and reached 0.8 nmol/min/mg.

The total amount of dienes formed was 386 nmol/mg of LDL in the absence of the compounds (FIG. 5c) and 374 nmol/mg in the presence of compound 27, 365 nmol/mg with compound 25 and 352 nmol/mg with compound 31.

Figure 6A:
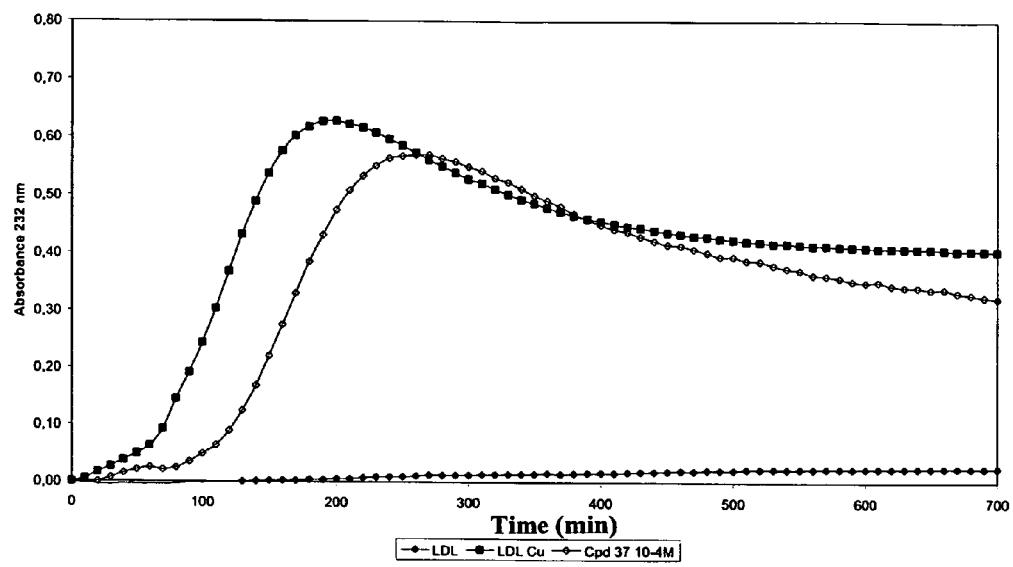
Figure 6B:
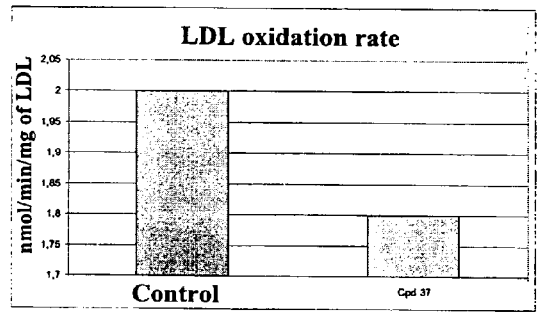
Figure 6C:
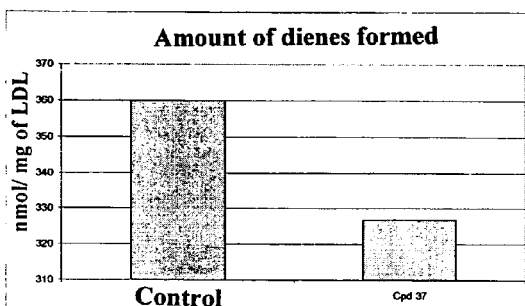

FIGS. 6a, 6b, 6c illustrate the antioxidant characteristics of inventive compound 37 (Cpd 37) tested at a concentration of $10^{-4}$ M.

FIG. 6a shows the kinetics of LDL oxidation. The presence of the compound in the medium induced an increase in the lag phase, reaching 106 minutes in the presence of compound 37 whereas in the absence of said compound it was only 56 minutes.

The decrease in the rate of LDL oxidation and the decrease in the amount of dienes formed also illustrate the antioxidant character of the test compound. In the absence of the compound, the oxidation rate was 2 nmol/min/mg of LDL compared with 1.8 nmol/min/mg of LDL when the compound was present (FIG. 6b). In the absence of the compound, the total amount of dienes formed was 360.0 nmol/mg of LDL whereas it was only 326.9 nmol/mg of LDL in the presence of compound 37 (FIG. 6c).

Figure 7A:
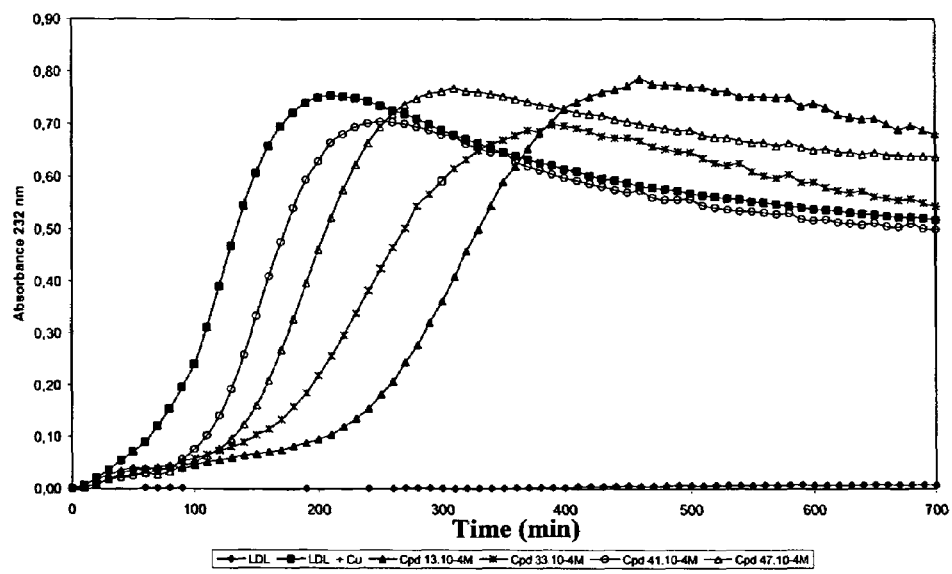
Figure 7B:
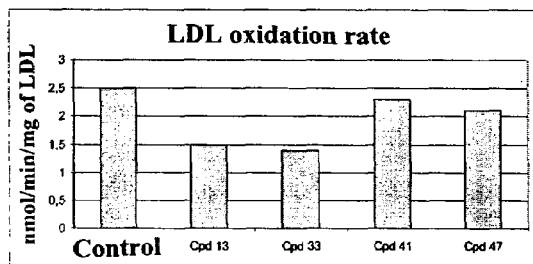
Figure 7C:
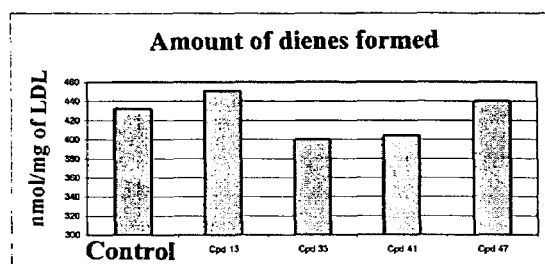

FIGS. 7a, 7b, 7c illustrate the antioxidant characteristics of inventive compound 13 (Cpd 13), compound 33 (Cpd 33), compound 41 (Cpd 41), compound 47 (Cpd 47), tested at a concentration of $10^{-4}$ M.

FIG. 7a shows the kinetics of LDL oxidation. In the absence of the antioxidant compounds, the lag phase was 67.3 minutes, increasing in the presence of the different compounds to a value of 100 minutes in the presence of compound 41, 126.5 minutes for compound 47, 148 minutes for compound 33 and 219 minutes for compound 13.

The presence of the compounds in the medium also had an effect on the LDL oxidation rate and on the total amount of dienes formed.

Compounds 13 and 33 induced a marked decrease in the diene oxidation rate (FIG. 7b), from 2.5 nmol/min/mg of LDL in the absence of the compounds to 1.5 and 1.4 nmol/min/mg of LDL in the presence of compounds 13 and 33, respectively.

Only compounds 33 and 41 induced a decrease in the total amount of dienes formed (FIG. 7c), which was 432.5 nmol/mg of LDL in the absence of the compounds as compared with 399 and 403 nmol/mg of LDL for compounds 33 and 41, respectively.

Figure 8A:
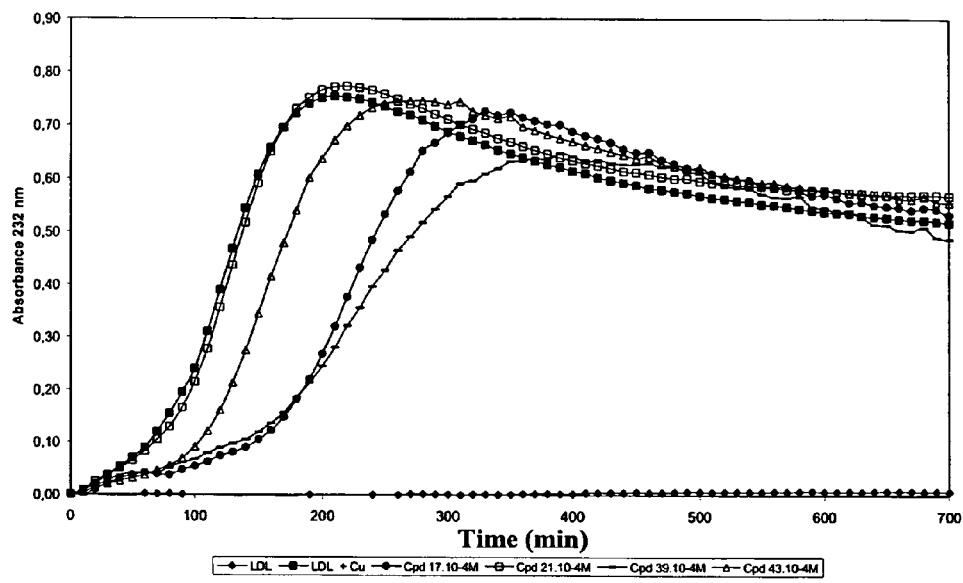
Figure 8B:
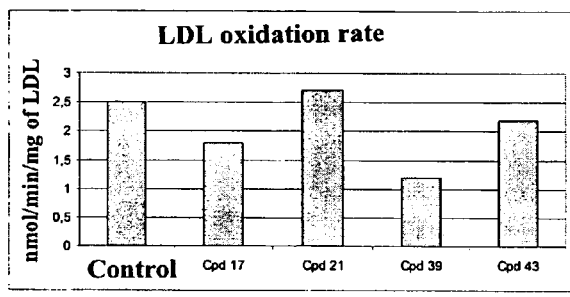
Figure 8C:
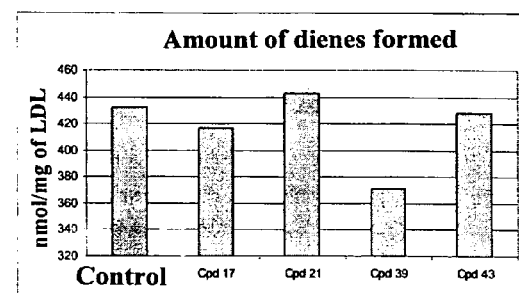

FIGS. 8a, 8b, 8c illustrate the antioxidant characteristics of inventive compound 17 (Cpd 17), compound 21 (Cpd 21), compound 39 (Cpd 39) and compound 43 (Cpd 43) tested at a concentration of $10^{-4}$ M.

The kinetics of LDL oxidation are shown in FIG. 8a.

In the absence of the compounds, the lag phase was 67.3 minutes, increasing to 97, 148 and 133 minutes for compound 43, 17 and 39, respectively.

FIG. 8b represents the rate of LDL oxidation, which was 2.5 nmol/min/mg in the absence of the compounds as compared with 1.8, 1.2 and 2.2 nmol/min/mg in the presence of compound 17, 39 and 43, respectively.

FIG. 8c shows the total amount of dienes formed during oxidation. Only compound 39 induced a significant decrease in the total amount of dienes formed, which was 432.3 nmol/mg in the absence of the compound and 371.2 nmol/mg in the presence of compound 39.

The longer lag phase of conjugated diene formation, the reduction in the rate of diene formation and the decrease in the total amount of dienes formed are three parameters which confirm the antioxidant characteristics of the inventive compounds.

FIGS. 9a and 9b show the evaluation of PPARα and PPARγ agonist properties of the inventive compounds using the PPARα/Gal4 and PPARγ/Gal4 transactivation system in RK13 cells.

RK13 cells were incubated with the compound 2 at concentrations comprised between 0.01 and 10 μM for 24 hours. The results are expressed as the induction factor (ratio of luminescent signal obtained with the compound and that observed without the compound) after the different treatments. The higher the induction factor the more potent the PPARα or PPARγ agonist activity.

FIG. 9a shows the induction factors for compound 2 with the PPARα/Gal4 transactivation system. The values of these induction factors are given in the following table.

| Compound | Treatment | Induction factor |
|---|---|---|
| Cpd 2 | 1 µM | 8.83 |
|  | 10 µM | 18.49 |

The induction factor for compound 2 was maximum at the 10 µM concentration, reaching a value of 18.49.

FIG. 9b shows the induction factors for compound 2 with the PPARγ/Gal4 transactivation system. The values of these induction factors are given in the following table:

| Compound | Treatment | Induction factor |
|---|---|---|
| Cpd 2 | 0.01 µM | 1.31 |
|  | 0.03 µM | 1.18 |
|  | 0.1 µM | 1.73 |
|  | 0.3 µM | 4.58 |
|  | 1 µM | 9.50 |
|  | 3 µM | 16.64 |
|  | 10 µM | 31.00 |

In the PPARγ/Gal4 system, the induction factors ranged from 1.31 to 31.00, increasing with the concentration of compound 2 in the medium.

FIGS. 10a 10b, 11a, 11b, 11c, 12a, 12b, 13a, 13b, 14a, 14b, 14c, 15a, 15b, 15c, 16a, 17a, 18a, 18b show the evaluation of PPARα, PPARγ and PPARδ agonist properties of the inventive compounds in the PPARα/Gal4, PPARγ/Gal4 and PPARδ/Gal4 transactivation system in COS-7 cells.

COS-7 cells were incubated with different concentrations of the inventive compounds for 24 hours. The results are expressed as the induction factor (ratio of luminescent signal obtained with the compound and that observed without the compound) after the different treatments.

FIGS. 10a and 10b show the induction factors for inventive compound 4 (Cpd4), compound 6 (Cpd6) and compound 8 (Cpd8).

FIG. 10a shows the induction factors for compound 4 (Cpd4), compound 6 (Cpd6) and compound 8 (Cpd8) with the PPARα/Gal4 transactivation system. The values of these induction factors are given in the following table:

| Compound | Treatment | Induction factor |
|---|---|---|
| Cpd 4 | 1 µM | 1.67 |
|  | 10 µM | 9.92 |
| Cpd 6 | 1 µM | 5.48 |
|  | 10 µM | 7.01 |
| Cpd 8 | 1 µM | 15.67 |
|  | 10 µM | 12.66 |

The maximum induction factor was 9.92 for compound 4 at a concentration of 10 µM, 7.01 for compound 6 (10 µM) and 15.67 for compound 8 (1 µM).

FIG. 10b shows the induction factors for compound 4, compound 6 and compound 8 with the PPARγ/Gal4 transactivation system. The values of these induction factors are given in the following table:

| Compound | Treatment | Induction factor |
|---|---|---|
| Cpd 4 | 1 µM | 2.00 |
|  | 10 µM | 5.82 |
| Cpd 6 | 1 µM | 4.12 |
|  | 10 µM | 6.83 |
| Cpd 8 | 1 µM | 2.13 |
|  | 10 µM | 2.74 |

Compound 4 had a maximum induction factor of 5.82 at the 10 µM concentration. The maximum induction factors were 6.83 for compound 6 (10 µM) and 2.74 for compound 8 (10 µM).

FIGS. 11a, 11b and 11c illustrate the induction factors for inventive compound 13 (Cpd13).

FIG. 11a shows the induction factors for compound 13 with the PPARα/Gal4 transactivation system. The values of these induction factors are given in the following table:

| Compound | Treatment | Induction factor |
|---|---|---|
| Cpd 13 | 0.001 µM | 1.10 |
|  | 0.003 µM | 1.58 |
|  | 0.01 µM | 4.99 |
|  | 0.03 µM | 10.89 |
|  | 0.1 µM | 16.87 |
|  | 0.3 µM | 15.95 |
|  | 1 µM | 17.05 |

The maximum induction factor of 17.05 was observed at a concentration of 1 µM.

FIG. 11b shows the induction factors of compound 13 with the PPARγ/Gal4 transactivation system. The values of these induction factors are given in the following table:

| Compound | Treatment | Induction factor |
|---|---|---|
| Cpd 13 | 0.001 µM | 0.99 |
|  | 0.003 µM | 1.15 |
|  | 0.01 µM | 1.67 |
|  | 0.03 µM | 2.18 |
|  | 0.1 µM | 3.01 |
|  | 0.3 µM | 3.66 |
|  | 1 µM | 4.03 |
|  | 3 µM | 3.89 |

The maximum value of 4.03 was seen at the 1 µM concentration.

FIG. 11c shows the induction factors of compound 13 with the PPARδ/Gal4 transactivation system. The values of these induction factors are given in the following table.

| Compound | Treatment | Induction factor |
|---|---|---|
| Cpd 13 | 0.01 µM | 1.50 |
|  | 0.03 µM | 2.17 |
|  | 0.1 µM | 3.37 |
|  | 0.3 µM | 14.00 |
|  | 1 µM | 28.75 |
|  | 3 µM | 27.72 |

The maximum value of 28.75 was seen at the 1 μM concentration.

FIGS. 12a and 12b illustrate the induction factors of inventive compound 23 (Cpd23).

FIG. 12a shows the induction factors of compound 23 with the PPARα/Gal4 transactivation system. The values of these induction factors are given in the following table:

| Compound | Treatment | Induction factor |
|---|---|---|
| Cpd 23 | 0.0003 μM | 0.92 |
| | 0.001 μM | 1.11 |
| | 0.003 μM | 1.33 |
| | 0.01 μM | 2.35 |
| | 0.03 μM | 4.22 |
| | 0.1 μM | 7.16 |
| | 0.3 μM | 8.08 |
| | 1 μM | 8.35 |
| | 3 μM | 7.15 |

The maximum value of 8.35 was seen at the 1 μM concentration.

FIG. 12b shows the induction factors for compound 23 with the PPARγ/Gal4 transactivation system. The values of these induction factors are given in the following table:

| Compound | Treatment | Induction factor |
|---|---|---|
| Cpd 23 | 0.0003 μM | 1.02 |
| | 0.001 μM | 1.43 |
| | 0.003 μM | 2.86 |
| | 0.01 μM | 3.48 |
| | 0.03 μM | 5.04 |
| | 0.1 μM | 6.17 |
| | 0.3 μM | 6.84 |
| | 1 μM | 7.24 |
| | 3 μM | 6.98 |

The maximum value of 7.24 was seen at the 1 μM concentration.

FIGS. 13a and 13b illustrate the induction factors of inventive compound 29 (Cpd29).

FIG. 13a shows the induction factors of compound 29 with the PPARα/Gal4 transactivation system. The values of these induction factors are given in the following table:

| Compound | Treatment | Induction factor |
|---|---|---|
| Cpd 29 | 0.001 μM | 1.09 |
| | 0.003 μM | 1.20 |
| | 0.01 μM | 1.49 |
| | 0.03 μM | 2.85 |
| | 0.1 μM | 6.93 |
| | 0.3 μM | 12.51 |
| | 1 μM | 15.56 |
| | 3 μM | 15.75 |

The maximum value of 15.75 was seen at the 3 μM concentration.

FIG. 13b shows the induction factors for compound 29 with the PPARδ/Gal4 transactivation system. The values of these induction factors are given in the following table:

| Compound | Treatment | Induction factor |
|---|---|---|
| Cpd 29 | 0.001 μM | 1.03 |
| | 0.003 μM | 1.07 |
| | 0.01 μM | 1.26 |
| | 0.03 μM | 1.63 |
| | 0.1 μM | 4.07 |
| | 0.3 μM | 11.61 |
| | 1 μM | 33.78 |
| | 3 μM | 60.81 |
| | 10 μM | 87.56 |

The maximum value of 87.56 was seen at the 10 μM concentration.

FIGS. 14a, 14b and 14c show the induction factors for inventive compound 31 (Cpd31).

FIG. 14a shows the induction factors for compound 31 with the PPARα/Gal4 transactivation system. The values of these induction factors are given in the following table:

| Compound | Treatment | Induction factor |
|---|---|---|
| Cpd 31 | 0.001 μM | 1.10 |
| | 0.003 μM | 1.09 |
| | 0.01 μM | 1.23 |
| | 0.03 μM | 1.23 |
| | 0.1 μM | 1.23 |
| | 0.3 μM | 1.73 |
| | 1 μM | 1.88 |
| | 3 μM | 3.69 |
| | 10 μM | 6.03 |

The maximum value of 6.03 was seen at the 10 μM concentration.

FIG. 14b shows the induction factors for compound 31 with the PPARγ/Gal4 transactivation system. The values of these induction factors are given in the following table:

| Compound | Treatment | Induction factor |
|---|---|---|
| Cpd 31 | 0.001 μM | 1.44 |
| | 0.003 μM | 2.19 |
| | 0.01 μM | 3.06 |
| | 0.03 μM | 4.87 |
| | 0.1 μM | 5.99 |
| | 0.3 μM | 6.96 |
| | 1 μM | 7.05 |
| | 3 μM | 7.79 |

The maximum value of 7.79 was seen at the 3 μM concentration.

FIG. 14c shows the induction factors for compound 31 with the PPARδ/Gal4 transactivation system. The values of these induction factors are given in the following table:

| Compound | Treatment | Induction factor |
|---|---|---|
| Cpd 31 | 0.001 μM | 1.00 |
| | 0.003 μM | 1.05 |
| | 0.01 μM | 1.09 |
| | 0.03 μM | 1.16 |

-continued

| Compound | Treatment | Induction factor |
|---|---|---|
| | 0.1 µM | 1.35 |
| | 0.3 µM | 2.67 |
| | 1 µM | 4.12 |
| | 3 µM | 10.82 |
| | 10 µM | 11.70 |

The maximum value of 11.70 was seen at the 10 µM concentration.

FIGS. 15a, 15b and 15c illustrate the induction factors for inventive compound 33 (Cpd33).

FIG. 15a shows the induction factors for compound 33 with the PPARα/Gal4 transactivation system. The values of these induction factors are given in the following table:

| Compound | Treatment | Induction factor |
|---|---|---|
| Cpd 33 | 0.001 µM | 5.23 |
| | 0.003 µM | 15.18 |
| | 0.01 µM | 19.53 |
| | 0.03 µM | 19.71 |
| | 0.1 µM | 19.17 |
| | 0.3 µM | 20.82 |
| | 1 µM | 19.97 |

The maximum value of 20.82 was seen at the 0.3 µM concentration.

FIG. 15b shows the induction factors for compound 33 with the PPARγ/Gal4 transactivation system. The values of these induction factors are given in the following table:

| Compound | Treatment | Induction factor |
|---|---|---|
| Cpd 33 | 0.001 µM | 1.18 |
| | 0.003 µM | 1.61 |
| | 0.01 µM | 2.65 |
| | 0.03 µM | 3.54 |
| | 0.1 µM | 4.88 |
| | 0.3 µM | 5.95 |
| | 1 µM | 6.93 |
| | 3 µM | 7.99 |
| | 10 µM | 6.30 |

The maximum value of 7.99 was seen at the 3 µM concentration.

FIG. 15c shows the induction factors for compound 33 with the PPARδ/Gal4 transactivation system. The values of these induction factors are given in the following table:

| Compound | Treatment | Induction factor |
|---|---|---|
| Cpd 33 | 0.001 µM | 1.17 |
| | 0.003 µM | 1.23 |
| | 0.01 µM | 1.87 |
| | 0.03 µM | 5.29 |
| | 0.1 µM | 15.01 |
| | 0.3 µM | 33.89 |
| | 1 µM | 74.09 |
| | 3 µM | 90.84 |

The maximum value of 90.84 was seen at the 3 µM concentration.

FIG. 16a illustrates the induction factors for inventive compound 35 (Cpd35).

FIG. 16a shows the induction factors for compound 35 with the PPARα/Gal4 transactivation system. The values of these induction factors are given in the following table:

| Compound | Treatment | Induction factor |
|---|---|---|
| Cpd 35 | 0.003 µM | 1.41 |
| | 0.01 µM | 1.54 |
| | 0.03 µM | 2.53 |
| | 0.1 µM | 7.47 |
| | 0.3 µM | 15.51 |
| | 1 µM | 24.33 |
| | 3 µM | 23.70 |
| | 10 µM | 21.03 |

The maximum value of 24.33 was seen at the 1 µM concentration.

FIG. 17a shows the induction factors for inventive compound 37 (Cpd37) with the PPARα/Gal4 transactivation system. The values of these induction factors are given in the following table:

| Compound | Treatment | Induction factor |
|---|---|---|
| Cpd 37 | 0.01 µM | 1.54 |
| | 0.03 µM | 2.54 |
| | 0.1 µM | 7.89 |
| | 0.3 µM | 17.25 |
| | 1 µM | 19.77 |
| | 3 µM | 16.89 |

The maximum value of 19.77 was seen at the 1 µM concentration.

FIGS. 18a and 18b show the induction factors for inventive compound 39 (Cpd39).

FIG. 18a shows the induction factors for compound 39 with the PPARα/Gal4 transactivation system. The values of these induction factors are given in the following table:

| Compound | Treatment | Induction factor |
|---|---|---|
| Cpd 39 | 0.001 µM | 1.08 |
| | 0.003 µM | 1.17 |
| | 0.01 µM | 3.19 |
| | 0.03 µM | 7.69 |
| | 0.1 µM | 9.68 |
| | 0.3 µM | 10.16 |
| | 1 µM | 10.42 |
| | 3 µM | 9.96 |

The maximum value of 10.42 was seen at the 1 µM concentration.

FIG. 18b shows the induction factors for compound 39 with the PPARγ/Gal4 transactivation system. The values of these induction factors are given in the following table:

| Compound | Treatment | Induction factor |
|---|---|---|
| Cpd 39 | 0.001 μM | 0.95 |
| | 0.003 μM | 0.96 |
| | 0.01 μM | 1.56 |
| | 0.03 μM | 3.06 |
| | 0.1 μM | 4.08 |
| | 0.3 μM | 4.86 |
| | 1 μM | 4.78 |
| | 3 μM | 4.72 |

The maximum value of 4.86 was seen at the 0.3 μM concentration.

These results shown in the figures demonstrate that the inventive compounds tested exhibit PPARα, PPARγ and/or PPARδ ligand activity and therefore enable the transcriptional activation of these nuclear receptors.

FIGS. 19a, 19b, 19c, 19d, 20a, 20b, 20c and 20d illustrate the effects of treatment with compound 2 (Cpd2), compound 13 (Cpd13), compound 33 (Cpd33) and compound 39 (Cpd39) on triglyceride and cholesterol metabolism in Apo E2/E2 transgenic mice treated by gavage with the compound at a dose of 50 mg/kg/day, for seven days.

FIGS. 19a and 19b illustrate the decrease in plasma triglycerides and cholesterol induced by compound 2.

FIGS. 20a and 20b illustrate the decrease in plasma triglycerides and cholesterol induced by compounds 13, 33 and 39.

FIGS. 19c and 19d illustrate the distribution of triglycerides and cholesterol in lipoparticles evaluated by exclusion chromatography, induced by treatment with compound 2.

FIGS. 20c and 20d illustrate the distribution of triglycerides and cholesterol in lipoparticles evaluated by exclusion chromatography, induced by treatment with compounds 13, 33 and 39.

A typical distribution of triglycerides and cholesterol primarily in large lipoparticles was observed. A decrease in triglycerides and cholesterol in this lipoparticle class was seen after treatment with the different test compounds.

Figure 21:
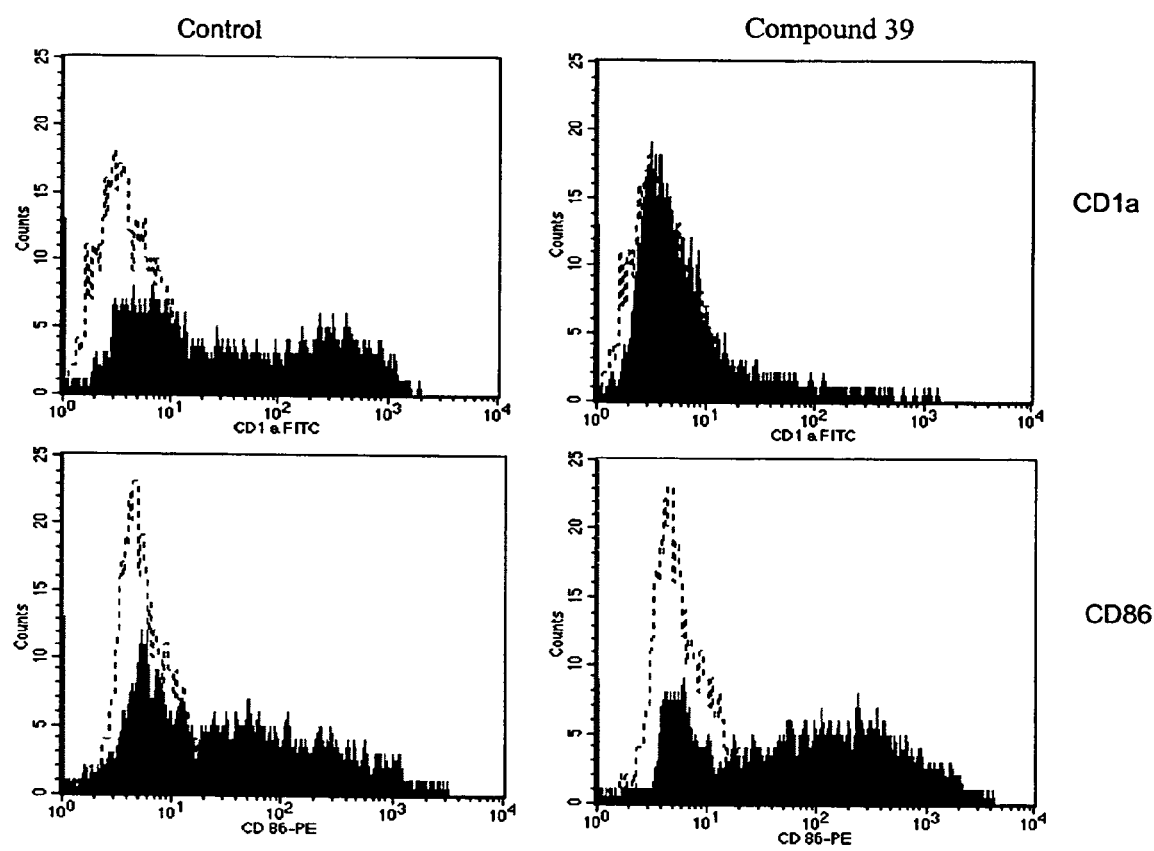

FIG. 21 illustrates the interference of the inventive compounds with dendritic cell differentiation.

Compound 39 ($10^{-6}$ M) was added at D0 of differentiation of monocytes to dendritic cells. After six days of differentiation (in the presence of cytokines GM-CSF and IL-4), the dendritic cells were analyzed by flow cytometry.

(---): Fluorochrome-coupled Ab with control isotype (in black): FITC (fluorescein isothiocyanate)-coupled anti-CD1a Ab or PE (phycoerythrin)-coupled anti-CD86 Ab.

Figure 22:
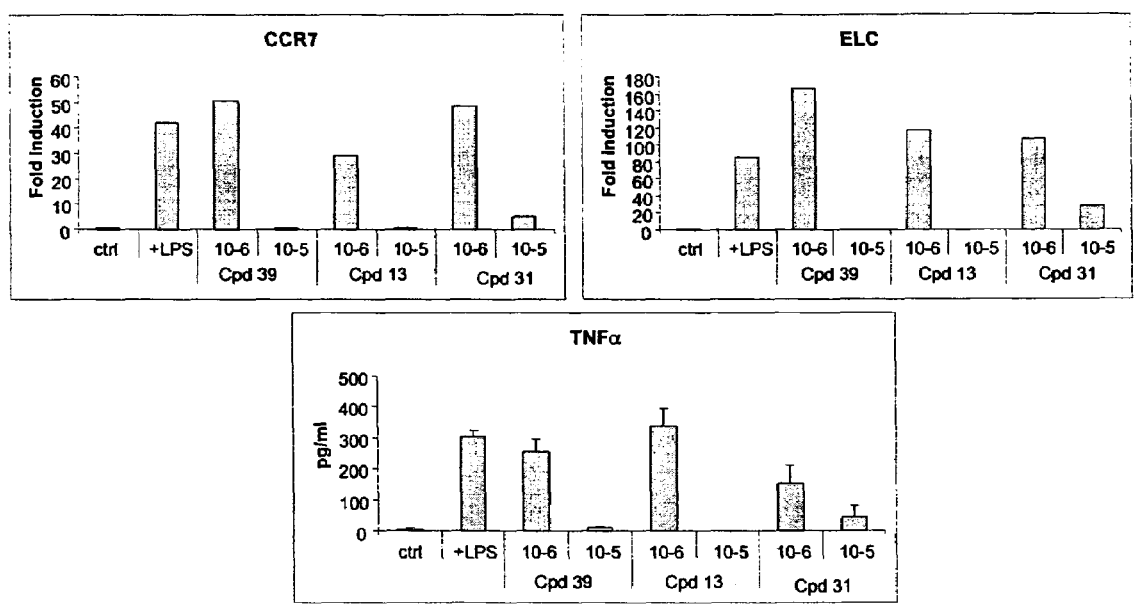

FIG. 22 illustrates the interference of the inventive compounds with LPS (lipopolysaccharide)-induced maturation of dendritic cells.

Dendritic cells were incubated for 4 hours with compounds 31, 13 or 39, then stimulated with LPS for 16 hours. CCR7 and ELC transcripts were analyzed by quantitative RT-PCR and the cytokine TNFalpha was analyzed by ELISA.

Figure 23:
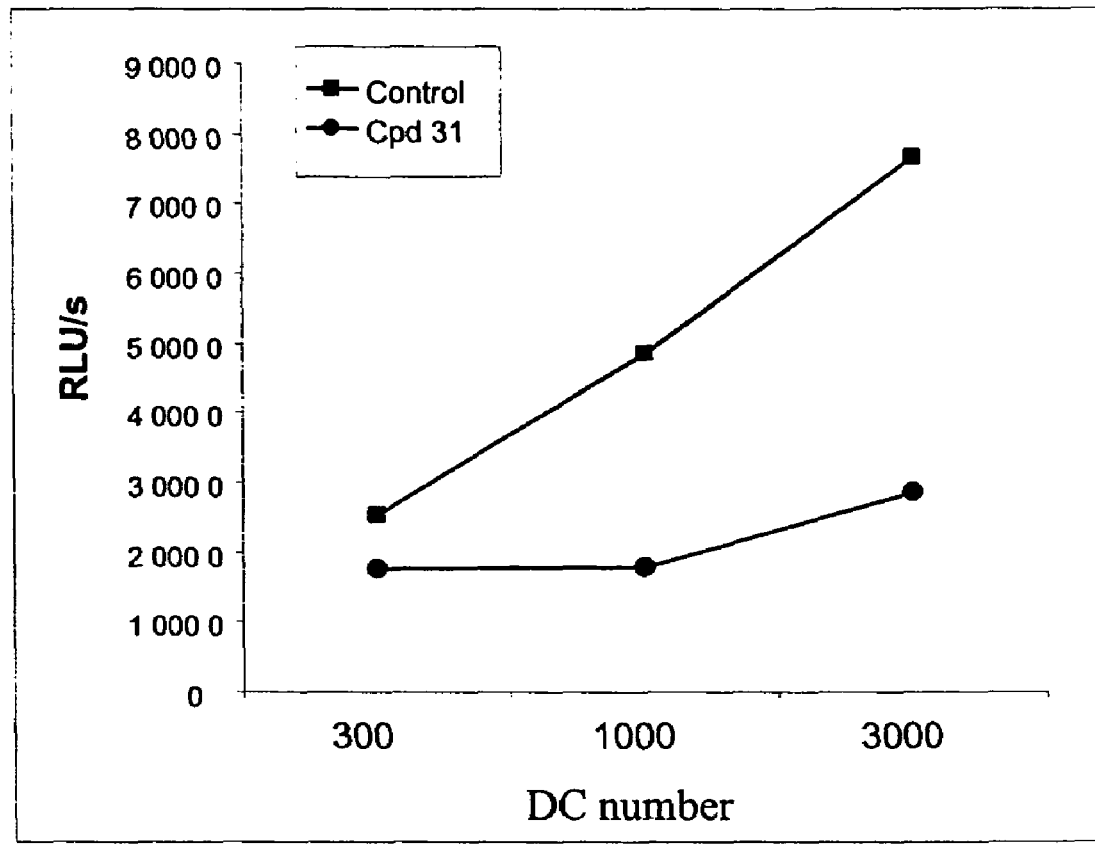

FIG. 23 illustrates a Mixed Lymphocyte Reaction (MLR) carried out in the presence of increasing amounts of dendritic cells treated or not with compound 31 and incubated with naive CD4+ T cells for seven days. T cell proliferation was determined by BrdU (bromodeoxyuridine) incorporation.

Other aspects and advantages of the invention will become apparent in the following examples, which are given for purposes of illustration and not by way of limitation.

EXAMPLES

Example 1

Synthesis of the Compounds according to the Invention

The compounds according to the invention were prepared according to the general methods outlined below.

Description of General Synthetic Methods of the Invention

Synthesis of 1,3-diphenylprop-2-en-1-ones

General Method 1

Synthesis of 1,3-diphenylprop-2-en-1-ones in acidic medium

The ketone (1 eq) and the aldehyde (1 eq) were dissolved in ethanol solution saturated with gaseous hydrochloric acid. The reaction was stirred at room temperature for 6 hours and the solvent was then eliminated by vacuum evaporation. The 1,3-diphenylprop-2-en-1-one was purified by chromatography on silica gel or by recrystallization.

General Method 2

Synthesis of 1,3-diphenylprop-2-en-1-ones in the presence of sodium hydroxide

The ketone (1 eq) and the aldehyde (1 eq) were dissolved in a hydroalcoholic solution of sodium hydroxide (20 eq). The mixture was stirred at room temperature for 18 hours. The medium was acidified to pH=2 with hydrochloric acid.

The 1,3-diphenylprop-2-en-1-one was obtained by precipitation or solid/liquid extraction after evaporation of the reaction medium. It was purified by silica gel chromatography or by recrystallization.

General Method 3

Synthesis of substituted 1,3-diphenylprop-2-en-1-ones in the presence of sodium ethylate Sodium (1 eq) was dissolved in absolute ethanol. The ketone (1 eq) and the aldehyde (1 eq) were added. The reaction mixture was stirred at room temperature for 12 hours and 2 N sodium hydroxide (5 eq) was then added. The mixture was kept at 100° C. for 12 hours. The reaction medium was acidified by adding 6 N aqueous hydrochloric acid solution. The solvent was eliminated by vacuum evaporation. The residue was purified by chromatography on silica gel or by recrystallization.

O-Alkylation of Phenols or Thiophenols

General Method 4

The phenol (1 eq) or the thiophenol (1 eq) was dissolved in acetonitrile and the halogenated derivative (1 to 10 eq) and potassium carbonate (5 eq) were added. The reaction medium was briskly stirred under reflux for approximately 10 hours. The salts were eliminated by filtration, the solvent and excess reagent were eliminated by vacuum evaporation, and the expected product was purified by silica gel chromatography.

General Method 5

The alcohol (1 eq), the phenol (1 eq) and the triphenylphosphine were dissolved in dichloromethane. Diisopropylazodicarboxylate (1 eq) was added and the mixture was stirred for 12 hours at room temperature.

The reaction medium was washed with water, dried on magnesium sulfate and vacuum evaporated. The evaporation residue was purified by silica gel chromatography.

Acid Hydrolysis of Tert-Butyl Esters

General Method 6

The tert-butyl ester (1 eq) was dissolved in dichloromethane, trifluoroacetic acid (10 eq) was added, and the mixture was stirred at room temperature for 12 hours. The resulting product was purified by chromatography on silica gel or by recrystallization.

Synthesis of Starting Materials Used to Synthesize the Inventive Compounds

Starting Material 1

4'-(Bromoethyloxy)acetophenone

This compound was synthesized from 4'-hydroxyacetophenone and dibromoethane according to general method 4 described earlier.

It was purified by chromatography on silica gel (elution: cyclohexane/ethyl acetate 9:1).

1H NMR CDCl$_3$ δppm: 2.55 (s, 3H), 3.66 (t, 2H, J=6.50 Hz), 4.35 (t, 2H, J=6.50 Hz), 6.94 (d, 2H, J=7.23 Hz), 7.94 (d, 2H, J=7.23 Hz)

Starting Material 2

4'-(Pentylthioethyloxy)acetophenone

Starting material 1 (1 eq) and penthanethiol (1 eq) were dissolved in methanol in the presence of triethylamine (2 eq). The reaction medium was refluxed for 18 hours and the solvent eliminated by vacuum evaporation. The oil was taken up in ethyl acetate, washed with aqueous 2N hydrochloric acid solution. 4'-(pentylthioethyloxy)acetophenone was obtained after purification on silica gel (elution: cyclohexane/ethyl acetate 9:1).

1H NMR CDCl$_3$ δppm: 0.85 (m, 3H), 1.24-1.39 (m, 4H), 1.52-1.62 (m, 2H), 2.50 (s, 3H), 2.64 (t, 2H, J=7.2 Hz), 2.94 (t, 2H, J=6.8 Hz), 4.14 (t, 2H, J=6.8 Hz), 6.88 (d, 2H, J=8.7 Hz), 7.89 (d, 2H, J=8.7 Hz)

Starting Material 3

3,5-Dimethyl-4-tert-butyloxycarbonyldimethylmethyloxybenzaldehyde

This compound was synthesized from 4-hydroxy-3,5-dimethylbenzaldehyde and tert-butyl bromoisobutyrate according to general method 4.

Purification was by chromatography on silica gel (elution: cyclohexane/ethyl acetate 8:2).

1H NMR CDCl$_3$ δppm: 1.43 (s, 6H), 1.49 (s, 9H), 2.28 (s, 6H), 7.53 (s, 2H), 9.88 (s, 1H)

Starting Material 4

4'-Hydroxy-3',5'-acetophenone 2,6-dimethylphenol (1 eq) was dissolved in methylene chloride and the solution was cooled to 0° C. Aluminium chloride (3 eq) and acetyl bromide (2 eq) were then added. The mixture was stirred for 3 hours at room temperature, then poured on ice. The aqueous phase was extracted with dichloromethane, the organic phase was washed with water until neutrality, dried on magnesium sulfate and the solvent was eliminated by vacuum evaporation. The intermediate ester obtained was purified by silica gel chromatography (elution: cyclohexane/ethyl acetate 9:1) then taken up in aqueous 2N sodium hydroxide (2.5 eq). The mixture was stirred for 48 hours at room temperature then acidified with dilute hydrochloric acid. The precipitate was washed with water until the wash water reached a neutral pH.

1H NMR CDCl$_3$ δppm: 2.30 (s, 6H), 2.54 (s, 3H), 7.65 (s, 2H)

Starting Material 5

4'-((R,S)-5-[1,2]dithiolan-3-ylpentyloxy)acetophenone

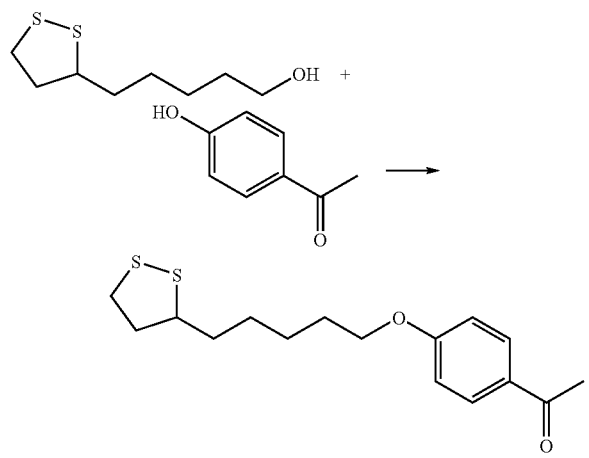

This compound was synthesized from 4'-hydroxyacetophenone and (R,S)-5-[1,2]dithiolan-3-ylpentanol according to general method 5 described earlier.

Purification was by chromatography on silica gel (elution: cyclohexane/ethyl acetate 95:5).

1H NMR CDCl$_3$ δppm: 1.42-1.62 (m, 4H), 1.62-1.75 (m, 2H), 1.75-1.89 (m, 2H), 1.89-1.98 (m, 1H), 2.42-2.51 (m, 1H), 2.56 (s, 3H), 3.08-3.21 (m, 2H), 3.55-3.61 (m, 1H), 4.06 (t, 2H, J=6.2 Hz), 6.92 (d, 2H, J=8.7 Hz), 7.93 (d, 2H, J=8.7 Hz)

Starting Material 6

(R,S)-2-phenyl-2-(4-formyl-1,6-dimethylphenyloxy) ethyl acetate

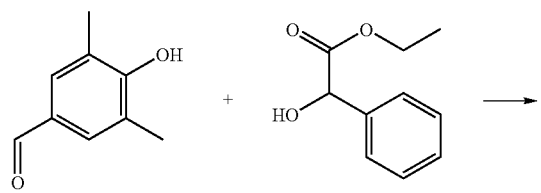

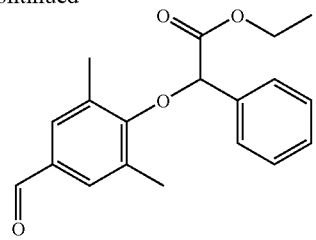

This compound was synthesized from 4-hydroxy-3,5-dimethylbenzaldehyde and 2-hydroxy-2-phenyl ethyl acetate according to general method 5 described earlier.

Purification was by chromatography on silica gel (elution: cyclohexane/ethyl acetate 9:1).

1H NMR CDCl$_3$ δppm: 1.22 (t, 3H, J=7.35 Hz), 2.20 (s, 6H), 4.16-4.28 (m, 2H), 5.3 (s, 1H), 7.38-7.51 (m, 7H), 9.87 (s, 1H)

Starting Material 7

4'-(Cyclohexylethyl)acetophenone

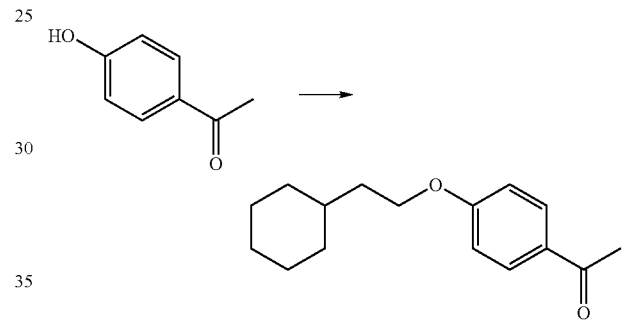

This compound was synthesized from 4'-hydroxyacetophenone and 2-cyclohexylethanol according to general method 5 described earlier.

Purification was by chromatography on silica gel (elution: cyclohexane/ethyl acetate 9:1).

1H NMR CDCl$_3$ δppm: 0.90-1.80 (m, 13H), 2.56 (s, 3H), 4.07 (t, 2H, J=6.45 Hz), 6.92 (d, 2H, J=8.80 Hz), 7.93 (d, 2H, J=8.80 Hz)

Starting Material 8

2,6-Dimethylthioanisole

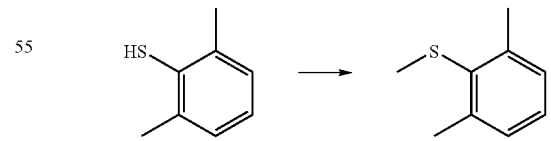

This compound was synthesized from 2,6-dimethylthiophenol and methyl iodide according to general method 4 described earlier.

Purification was by chromatography on silica gel (elution: cyclohexane/ethyl acetate 9:1).

1H NMR CDCl$_3$ δppm: 2.28 (s, 3H), 2.62 (s, 6H), 7.16 (m, 3H)

Starting Material 9

3',5'-Dimethyl-4'-methylthioacetophenone

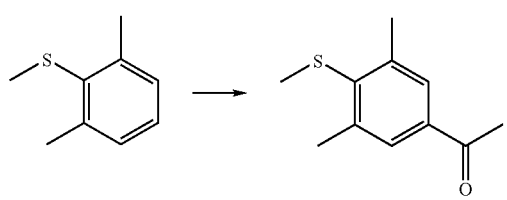

Starting material 8 (1 eq) was dissolved in methylene chloride, the solution was cooled to 0° C. and aluminium chloride (2.5 eq) and acetyl bromide (2 eq) were then added. The mixture was stirred for 72 hours at room temperature, then poured on ice. The aqueous phase was extracted with dichloromethane, the organic phase was washed with water until neutrality, dried on magnesium sulfate and the solvent was eliminated by vacuum evaporation.

Purification was by chromatography on silica gel (elution: cyclohexane/ethyl acetate 9:1).

1H NMR CDCl₃ δppm: 2.23 (s, 3H), 2.54 (s, 3H), 2.56 (s, 6H), 7.63 (s, 2H)

Starting Material 10

4'-Methoxy-3',5'-dimethylacetophenone

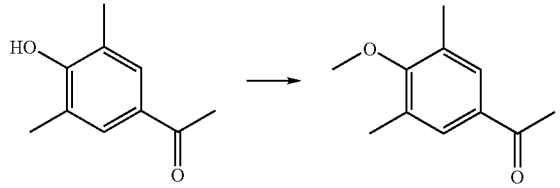

This compound was synthesized from starting material 4 and methyl iodide according to general method 4 described earlier.

The crude product obtained after elimination of the potassium carbonate by filtration and elimination of the solvents by vacuum evaporation was used for the synthesis of the corresponding intermediate compound.

1H NMR CDCl₃ δppm: 2.31 (s, 6H), 2.54 (s, 3H), 3.74 (s; 3H), 7.63 (s, 2H)

Starting Material 11

4'-Cyclohexylethyl-3',5'-dimethylacetophenone

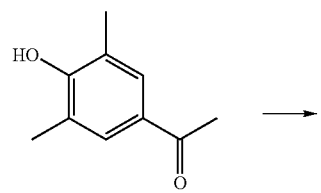

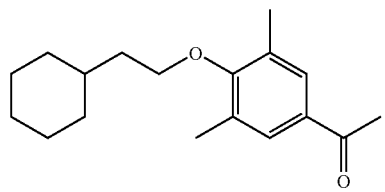

This compound was synthesized from starting material 4 and 2-cyclohexylethanol according to general method 5 described earlier.

Purification was by chromatography on silica gel (elution: cyclohexane/ethyl acetate 85:15).

1H NMR CDCl₃ δppm: 0.92-1.80 (m, 13H), 2.31 (s, 6H), 2.55 (s, 3H), 3.86 (t, 2H, J=7.05 Hz), 7.63 (s, 2H)

Starting Material 12

4'-(Bromoethyloxy)-3',5'-dimethylacetophenone

This compound was synthesized from starting material 4 and dibromoethane according to general method 4 as described above.

Purification was by chromatography on silica gel (elution: cyclohexane/ethyl acetate 85:15).

1H NMR CDCl₃ δppm: 2.36 (s, 6H), 2.56 (s, 3H), 3.68 (t, 2H, J=6.21 Hz), 4.14 (t, 2H, J=6.21 Hz), 7.65 (s, 2H)

Starting Material 13

4'-(Cyclohexylthioethyloxy)acetophenone

-continued

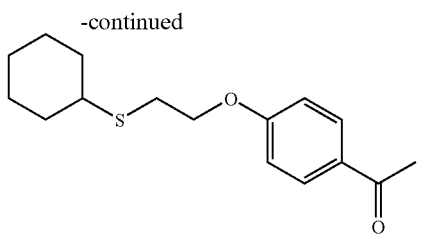

This compound was synthesized from starting material 1 and cyclohexane thiol according to general method 4 as described above.

1H NMR CDCl$_3$ δppm: 1.08 (m, 5H), 1.40 (m, 1H), 1.56 (m, 2H), 1.80 (m, 2H), 2.30 (s, 3H), 2.53 (m, 1H), 2.69 (t, 2H, J=6.96 Hz), 3.95 (t, 2H, J=6.96 Hz), 6.68 (d, 2H, J=8.88 Hz), 7.69 (d, 2H, J=8.88 Hz)

Starting Material 14

4'-(Cyclohexylthioethyloxy)-3',5'-dimethylacetophenone

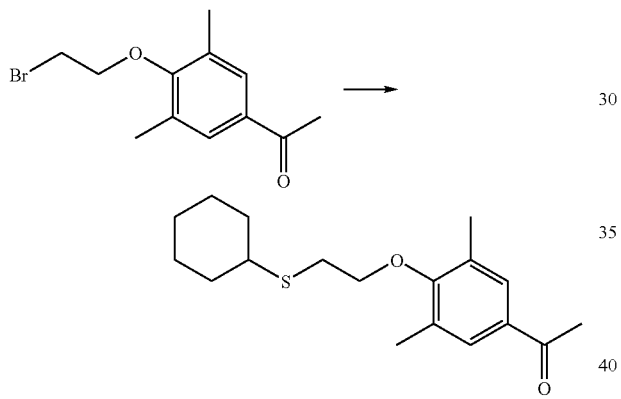

This compound was synthesized from starting material 12 and cyclohexane thiol according to general method 4 as described above.

Purification was by chromatography on silica gel (elution: cyclohexane/ethyl acetate 9:1).

1H NMR CDCl$_3$ δppm: 1.26-1.42 (m, 5H), 1.59-1.65 (m, 1H), 1.80 (m, 2H), 2.00 (m, 2H), 2.35 (s, 6H), 2.56 (s, 3H), 2.75 (m, 1H), 2.95 (t, 2H, J=6.81 Hz), 3.96 (t, 2H, J=6.81 Hz), 7.64 (s, 2H)

Starting Material 15

4'-Methoxy-3'-methylacetophenone

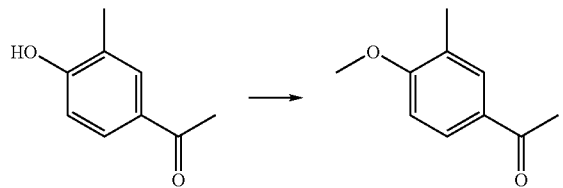

This compound was synthesized from 4'-hydroxy-3-methylacetophenone and methyl iodide according to general method 4 as described above.

The crude product obtained after elimination of the potassium carbonate by filtration and elimination of the solvents by vacuum evaporation was used for the synthesis of the corresponding intermediate compound.

1H NMR CDCl$_3$ δppm: 2.53 (s, 3H), 2.56 (s, 3H), 3.90 (s, 3H), 6.85 (d, 1H, J=8.46 Hz), 7.78 (s, 1H), 7.82 (d, 1H, J=8.46 Hz)

Starting Material 16

1,3-Dimethyl-2-hexylthiobenzene

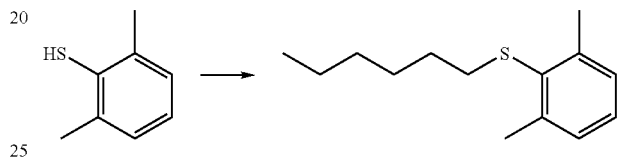

This compound was synthesized from 2,6-dimethylthiophenol and hexyl bromide according to general method 4 as described above.

Purification was by chromatography on silica gel (elution: cyclohexane).

1H NMR CDCl$_3$ δppm: 0.90 (t, 3H, J=6.57 Hz), 1.27-1.58 (m, 8H), 2.57 (s, 6H), 2.66 (t, 2H, J=7.11 Hz), 7.12 (m, 3H)

Starting Material 17

3',5'-Dimethyl-4'-hexylthioacetophenone

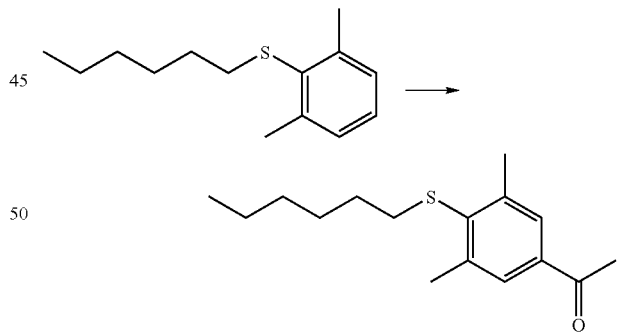

Starting material 16 (1 eq) was dissolved in methylene chloride, the solution was cooled to 0° C. and aluminium chloride (1 eq) and acetyl bromide (1 eq) were then added. The mixture was stirred for 2 hours at room temperature, then poured on ice. The aqueous phase was extracted with dichloromethane, the organic phase was washed with water until neutrality, dried on magnesium solvent and the solvent was eliminated by vacuum evaporation.

Purification was by chromatography on silica gel (elution: cyclohexane).

1H NMR CDCl$_3$ δppm: 0.87 (t, 3H, J=6.72 Hz), 1.22-1.53 (m, 8H), 2.58 (s, 3H), 2.59 (s, 6H), 2.68 (t, 2H, J=7.23 Hz), 7.66 (s, 2H)

Starting Material 18

3',5'-Dimethyl-4'-(Morpholin-4-ylethyloxy)acetophenone

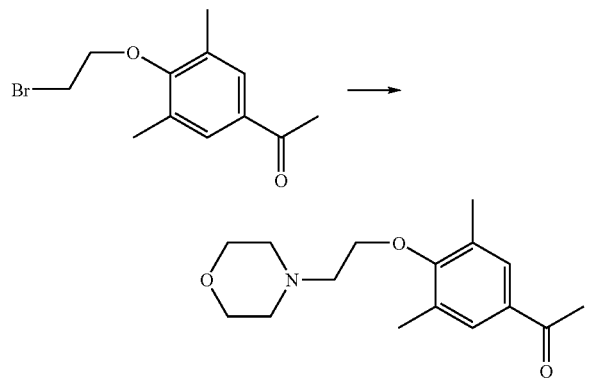

Starting material 12 (1 eq) and morpholine (0.7 eq) were dissolved in acetone and potassium carbonate (1 eq) was added. The mixture was refluxed for 72 hours. Potassium carbonate was eliminated by filtration, the solvent was eliminated by vacuum evaporation. The residual oil was taken up in aqueous 1N hydrochloric acid solution and washed with ethyl acetate. The aqueous phase was basified (pH 9) by addition of potassium carbonate, then extracted with ethyl acetate. The organic phase was dried on magnesium sulfate and the solvent was eliminated by vacuum evaporation.

1H NMR CDCl$_3$ δppm: 2.33 (s, 6H), 2.54 (s, 3H), 2.60 (t, 4H, J=4.70 Hz), 2.81 (t, 2H, J=5.76 Hz), 3.76 (t, 4H, J=4.70 Hz) 3.93 (t, 2H, J=5.76 Hz), 7.62 (s, 2H)

Starting Material 19

3,5-Difluoro-4-hydroxybenzaldehyde

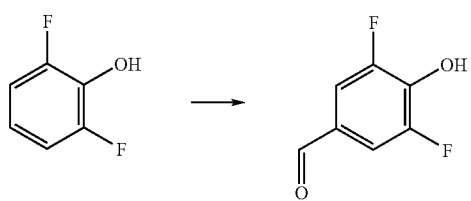

2,6-difluorophenol (1 eq) and hexamethylenetetramine (2 eq) were dissolved in a water/acetic acid mixture (10:90). The reaction mixture was refluxed for 18 hours then cooled to room temperature.

The reaction mixture was extracted with dichloromethane, the organic phases were pooled, dried on magnesium sulfate, and the solvent was eliminated by vacuum evaporation.

1H NMR CDCl$_3$ δppm: 7.35 (dd, 2H, J=6.57 Hz, J=2.82 Hz), 9.67 (s, 1H)

Starting Material 20

4'-Methoxy-3'-trifluoromethylacetophenone

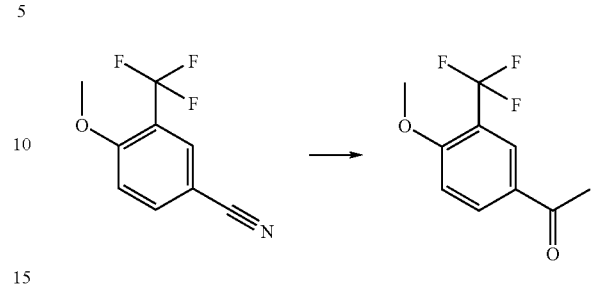

4-methoxy-3-trifluoromethylbenzonitrile (1 eq) was dissolved in anhydrous THF. Magnesium methyl chloride in solution in THF (1 eq) was added and the reaction mixture was stirred for 16 hours at room temperature then one hour under reflux after adding more magnesium methyl chloride (1 eq).

The reaction mixture was poured on an aqueous 1N hydrochloric acid solution and extracted with dichloromethane. The organic phase was neutralized with aqueous potassium bicarbonate solution then washed with water and dried on magnesium sulfate. The solvent was eliminated by vacuum evaporation.

Purification was by chromatography on silica gel (elution: cyclohexane/ethyl acetate 9:1).

1H NMR CDCl$_3$ δppm: 2.60 (s, 3H), 3.99 (s, 3H), 7.07 (d, 1H, J=8.79 Hz), 8.14 (d, 1H, J=8.79 Hz, J=1.77 Hz), 8.19 (s, 1H)

Synthesis of Intermediate Compounds Used to Synthesize the Inventive Compounds

Intermediate Compound 1

1-(4-(Pentylthioethyloxy)phenyl)-3-(4-hydroxy-3,5-dimethylphenyl)prop-2-en-1-one

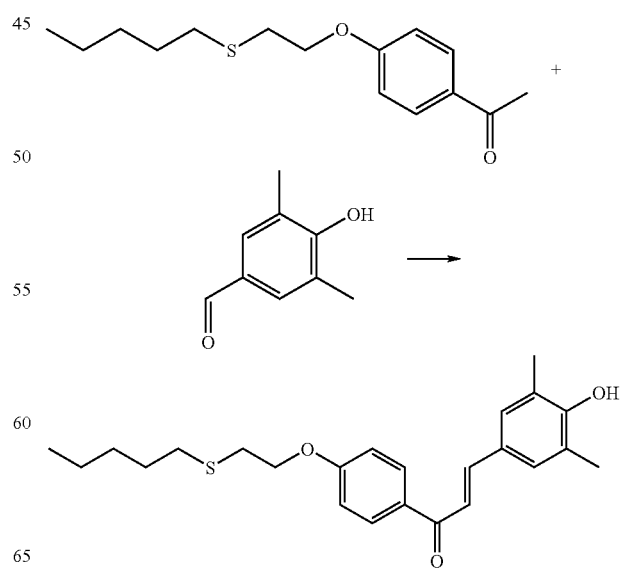

This compound was synthesized from starting material 2 and 4-hydroxy-3,5-dimethylbenzaldehyde according to general method 1 as described above.

Purification was by chromatography on silica gel (elution: cyclohexane/ethyl acetate 85:15).

1H NMR CDCl₃ δppm: 0.91 (m, 3H), 1.33-1.42 (m, 4H), 1.59-1.67 (m, 2H), 2.29 (s, 6H), 2.64 (t, 2H, J=7.60 Hz), 2.96 (t, 2H, J=6.80 Hz), 4.24 (t, 2H, J=6.80 Hz), 6.97 (d, 2H, J=8.70 Hz), 7.31 (s, 2H), 7.37 (d, 1H, J=15.54 Hz), 7.72 (d, 1H, J=15.54 Hz), 8.03 (d, 2H, J=8.70 Hz)

Intermediate Compound 2

1-(4-((R,S)-5-[1,2]dithiolan-3-ylpentyloxy)phenyl)-3-(4-hydroxy-3,5-dimethylphenyl)prop-2-en-1-one

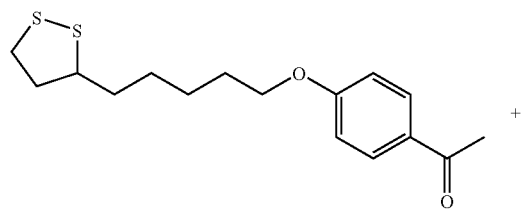

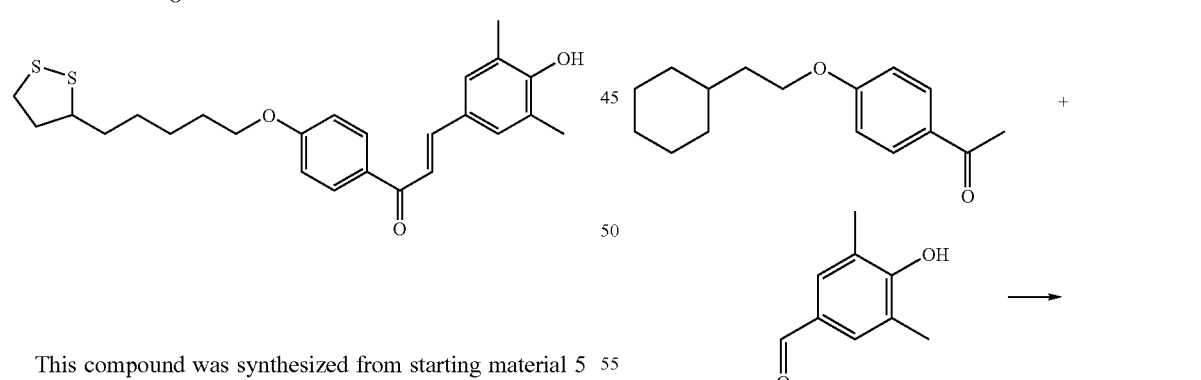

This compound was synthesized from starting material 5 and 4-hydroxy-3,5-dimethylbenzaldehyde according to general method 1 as described above.

Purification was by chromatography on silica gel (elution: cyclohexane/ethyl acetate 8:2).

1H NMR CDCl₃ δppm: 1.45-1.65 (m, 4H), 1.65-1.77 (m, 2H), 1.77-1.87 (m, 2H), 1.87-2.0 (m, 1H), 2.30 (s, 6H), 2.43-2.51 (m, 1H), 3.09-3.22 (m, 2H), 3.56-3.62 (m, 1H), 4.04 (t, 2H, J=6.40 Hz), 6.96 (d, 2H, J=8.50 Hz), 7.31 (s, 2H), 7.41 (d, 1H, J=15.40 Hz), 7.73 (d, 1H, J=15.40 Hz), 8.04 (d, 2H, J=8.50 Hz)

Intermediate Compound 3

1-(4-Methylthiophenyl)-3-(4-hydroxy-3,5-dibromophenyl)prop-2-en-1-one

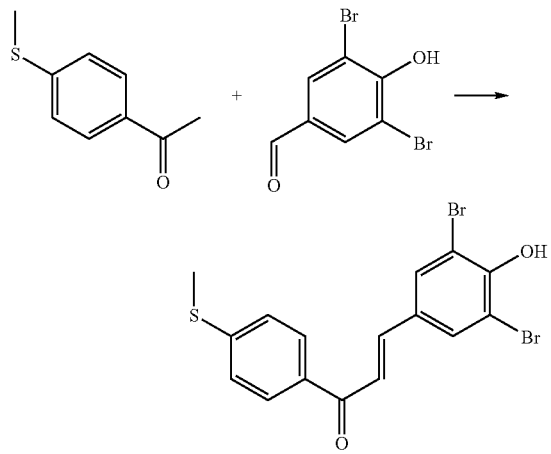

This compound was synthesized from 4'-methylthioacetophenone and 3,5-dibromo-4-hydroxybenzaldehyde according to general method 1 as described above.

Purification was by chromatography on silica gel (elution: cyclohexane/ethyl acetate 8:2).

1H NMR CDCl₃ δppm: 2.55 (s, 3H), 6.19 (s, 1H), 7.32 (d, 2H, J=8.70 Hz), 7.41 (1H, J=15.40 Hz), 7.63 (d, 1H, J=15.40 Hz), 7.75 (s, 2H), 7.96 (d, 2H, J=8.70 Hz)

Intermediate Compound 4

1-(4-(Cyclohexylethyloxy)phenyl)-3-(4-hydroxy-3,5-dimethylphenyl)prop-2-en-1-one

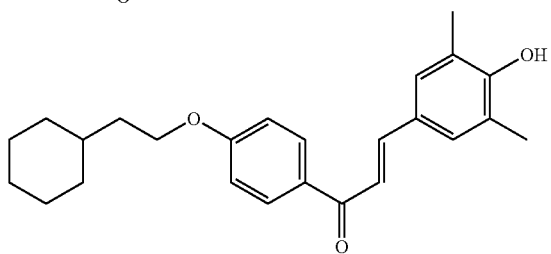

This compound was synthesized from starting material 7 and 3,5-dimethyl-4-hydroxybenzaldehyde according to general method 1 as described above.

The product crystallized in the reaction medium and was drained, washed with ethanol previously cooled to 0° C. and vacuum dried.

1H NMR CDCl₃ δppm: 0.90-1.80 (m, 13H), 2.30 (s, 6H), 4.08 (t, 2H, J=6.54 Hz), 6.97 (d, 2H, J=9.00 Hz), 7.30 (s, 2H), 7.42 (d, 1H, J=15.50 Hz), 7.73 (d, 1H, J=15.50 Hz), 8.03 (d, 2H, J=9.00 Hz)

Intermediate Compound 5

1-(4-Methylthio-3,5-dimethyl-phenyl)-3-(4-hydroxy-3,5-dimethylphenyl)prop-2-en-1-one

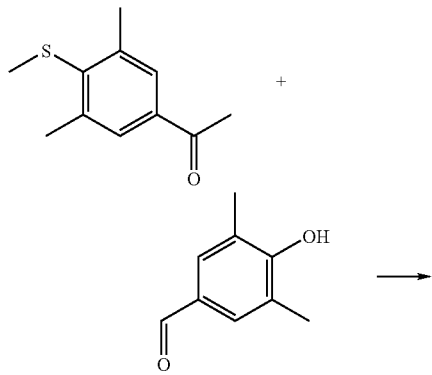

This compound was synthesized from starting material 9 and 3,5-dimethyl-4-hydroxybenzaldehyde according to general method 1 as described above.

Purification was by chromatography on silica gel (elution: cyclohexane/ethyl acetate 8:2).

1H NMR CDCl₃ δppm: 2.28 (s, 3H), 2.30 (s, 6H), 2.64 (s, 6H), 7.32 (s, 2H), 7.36 (d, 1H, J=15.76 Hz), 7.72 (s, 2H), 7.73 (d, 1H, J=15.76 Hz)

Intermediate Compound 6

1-(4-Methoxy-3,5-dimethylphenyl)-3-(4-hydroxy-3,5-dimethylphenyl)prop-2-en-1-one

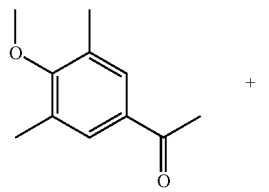

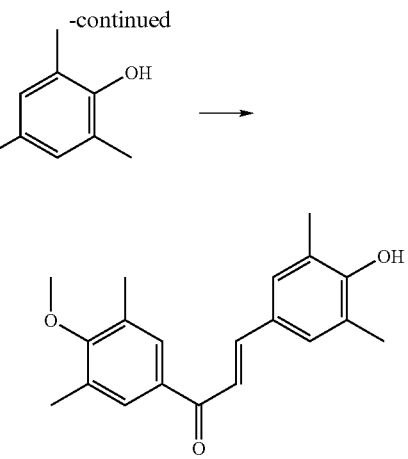

This compound was synthesized from starting material 10 and 3,5-dimethyl-4-hydroxybenzaldehyde according to general method 1 as described above.

The product crystallized in the reaction medium and was drained, washed with ethanol previously cooled to 0° C. and vacuum dried.

1H NMR CDCl₃ δppm: 2.28 (s, 6H), 2.35 (s, 6H), 3.77 (s, 3H), 7.30 (s, 2H), 7.35 d, 1H, J=15.63 Hz), 7.70 (d, 1H, J=15.63 Hz), 7.72 (s, 2H)

Intermediate Compound 7

1-(4-(Cyclohexylethyloxy)-3,5-dimethylphenyl)-3-(4-hydroxy-3,5-dimethylphenyl)prop-2-en-1-one

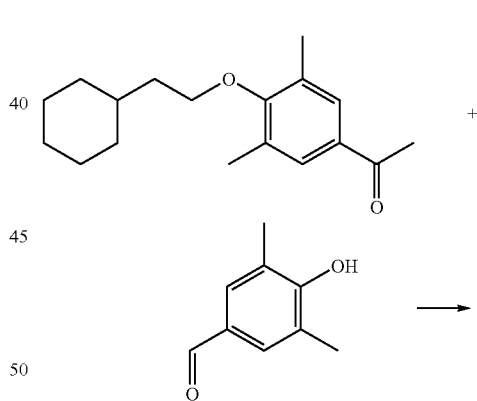

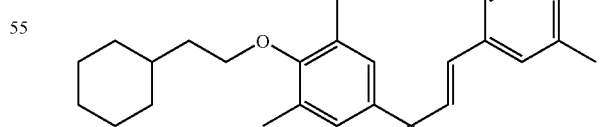

This compound was synthesized from starting material 11 and 3,5-dimethyl-4-hydroxybenzaldehyde according to general method 1 as described above.

Purification was by chromatography on silica gel (elution: cyclohexane/ethyl acetate 8:2).

1H NMR CDCl₃ δppm: 0.94-1.05 (m, 2H), 1.16-1.31 (m, 4H), 1.57-1.82 (m, 7H), 2.30 (s, 6H), 2.35 (s, 6H), 3.86 (t, 2H, J=7.08 Hz), 7.32 (s, 2H), 7.38 (d, 1H, J=15.81 Hz), 7.71 (s, 2H), 7.72 (d, 1H, J=15.81 Hz)

Intermediate Compound 8

1-(4-(Cyclohexylthioethyloxy)phenyl)-3-(4-hydroxy-3,5-dimethylphenyl)prop-2-en-1-one

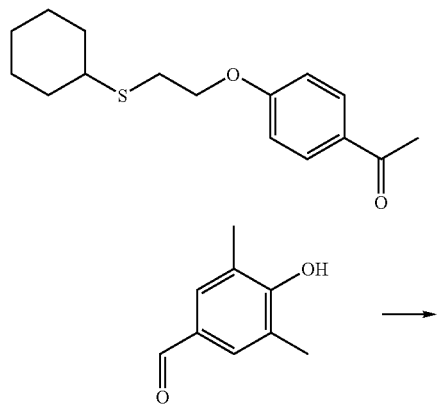

This compound was synthesized from starting material 13 and 3,5-dimethyl-4-hydroxybenzaldehyde according to general method 1 as described above.

The product crystallized in the reaction medium and was drained and washed with ethanol previously cooled to 0° C.

1H NMR CDCl₃ δppm: 1.23-1.42 (m, 5H), 1.63-1.65 (m, 1H), 1.79-1.81 (m, 2H), 2.01-2.08 (m, 2H), 2.29 (s, 6H), 2.73-2.81 (m, 1H), 2.96 (t, 2H, J=7.08 Hz), 4.20 (t, 2H, J=7.08 Hz), 6.97 (d, 2H, J=8.73 Hz), 7.30 (s, 2H), 7.41 (d, 1H, J=15.53 Hz), 7.73 (d, 1H, J=15.53 Hz), 8.04 (d, 2H, J=8.73 Hz)

Intermediate Compound 9

1-(2,4,5-Trimethylphenyl)-3-(4-hydroxy-3,5-dimethylphenyl)prop-2-en-1-one

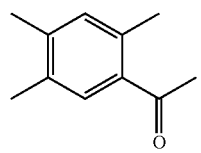

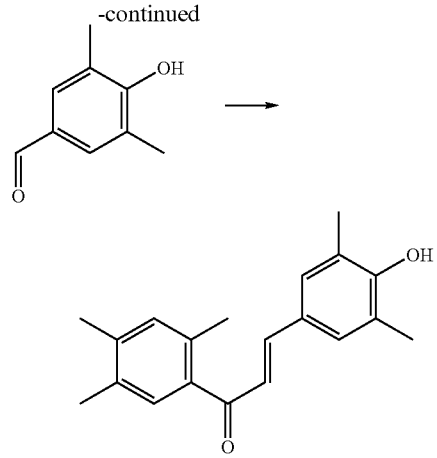

This compound was synthesized from 2',4',5'-trimethylacetophenone and 3,5-dimethyl-4-hydroxybenzaldehyde according to general method 1 described earlier.

Purification was by chromatography on silica gel (elution: cyclohexane/ethyl acetate 7:3).

1H NMR CDCl₃ δppm: 2.27 (s, 9H), 2.29 (s, 3H), 2.38 (s, 3H), 7.00 (d, 1H, J=15.90 Hz), 7.04 (s, 1H), 7.23 (s, 2H), 7.27 (s, 1H), 7.39 (d, 1H, J=15.90 Hz)

Intermediate Compound 10

1-(4-(Cyclohexylthioethyloxy)-3,5-dimethylphenyl)-3-(4-hydroxy-3,5-dimethylphenyl)prop-2-en-1-one

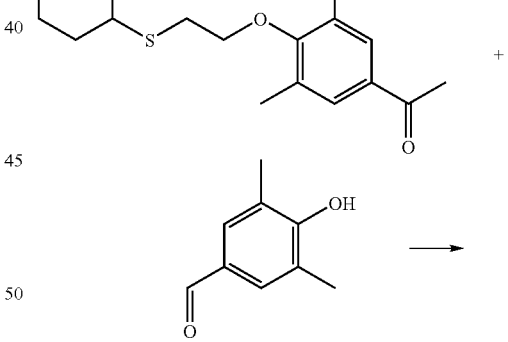

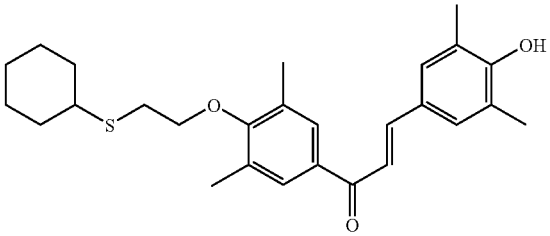

This compound was synthesized from starting material 14 and 3,5-dimethyl-4-hydroxybenzaldehyde according to general method 1 described earlier.

Purification was by chromatography on silica gel (elution: cyclohexane/ethyl acetate 7:3).

1H NMR CDCl₃ δppm: 1.32 (m, 5H), 1.63 (m, 1H), 1.79 (m, 2H), 2.03 (m, 2H), 2.29 (s, 6H), 2.37 (s, 6H), 2.75 (m, 1H), 2.97 (t, 2H, J=7.05 Hz), 3.97 (t, 2H, J=7.05 Hz), 7.30 (s, 2H) 7.37 (d, 1H, J=15.70 Hz), 7.70 (d, 1H, J=15.70 Hz), 7.71 (s, 2H)

Intermediate Compound 1

1-(4-Methylthiophenyl)-3-(4-hydroxy-3-fluorophenyl)prop-2-en-1-one

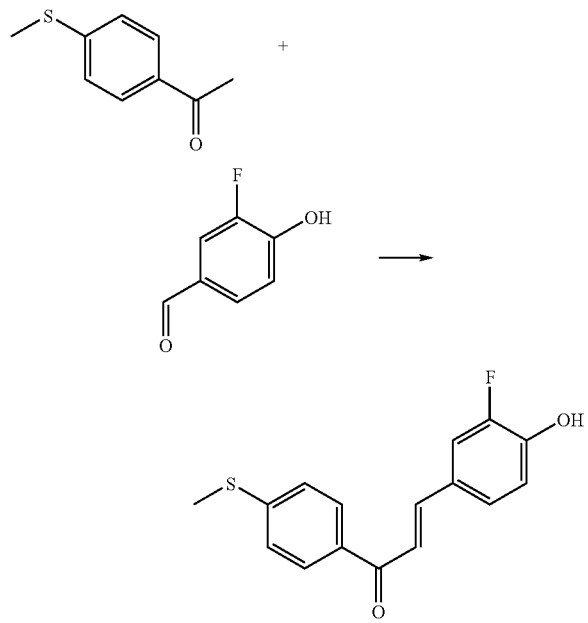

This compound was synthesized from 4'-methylthioacetophenone and 3-fluoro-4-hydroxybenzaldehyde according to general method 1 described earlier.

The product crystallized in the reaction medium and was drained and vacuum dried.

1H NMR CDCl₃ δppm: 2.55 (s, 3H), 7.04 (t, 1H, J=8.37 Hz), 7.30-7.42 (m, 5H), 7.73 (d, 1H, J=15.54 Hz), 7.95 (d, 2H, J=8.40 Hz)

Intermediate Compound 12

1-(2,3,4,5,6-Pentamethylphenyl)-3-(4-hydroxy-3,5-dimethylphenyl)prop-2-en-1-one

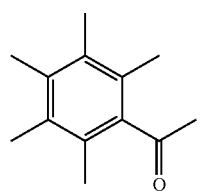

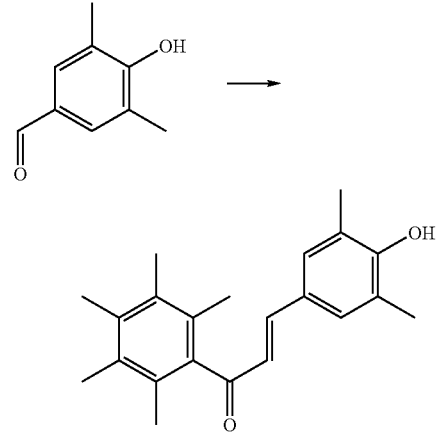

This compound was synthesized from pentamethylacetophenone and 3,5-dimethyl-4-hydroxybenzaldehyde according to general method 1 described earlier.

The product crystallized in the reaction medium and was drained and purified by recrystallization in ethanol.

1H NMR CDCl₃ δppm: 2.09 (s, 6H), 2.20 (s, 6H), 2.22 (s, 6H), 2.26 (s, 3H), 6.83 (d, 1H, J=16.11 Hz), 7.05 (d, 1H, J=16.11 Hz), 7.16 (s, 2H)

Intermediate Compound 13

1-(4-Phenoxyphenyl)-3-(4-hydroxy-3,5-dimethylphenyl)prop-2-en-1-one

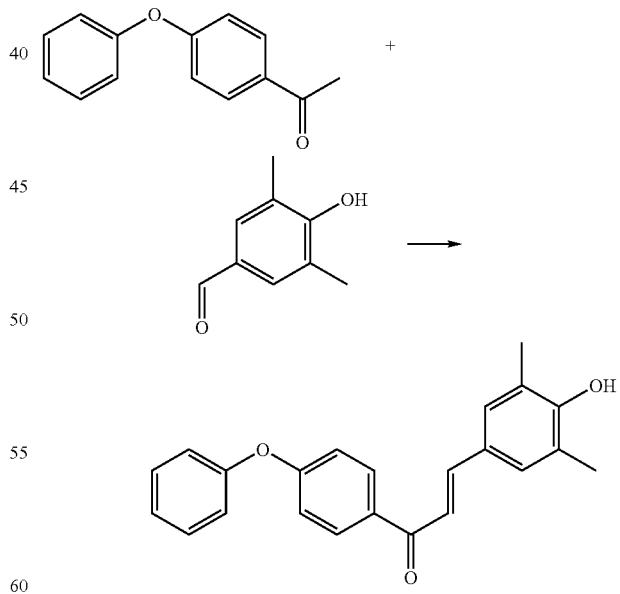

This compound was synthesized from 4'-phenoxyacetophenone and 3,5-dimethyl-4-hydroxybenzaldehyde according to general method 1 described earlier.

Purification was by chromatography on silica gel (elution: cyclohexane/ethyl acetate 7:3).

1H NMR CDCl₃ δppm: 2.30 (s, 6H), 7.05 (d, 2H, J=8.67 Hz), 7.1 (d, 2H, J=8.47 Hz), 7.21 (t, 1H, J=7.30 Hz), 7.31 (s, 2H), 7.43-7.38 (m, 3H), 7.75 (d, 1H, J=15.36 Hz), 8.05 (d, 2H, J=8.47 Hz)

Intermediate Compound 14

1-(4-Methoxy-3-fluorophenyl)-3-(4-hydroxy-3,5-dimethylphenyl)prop-2-en-1-one

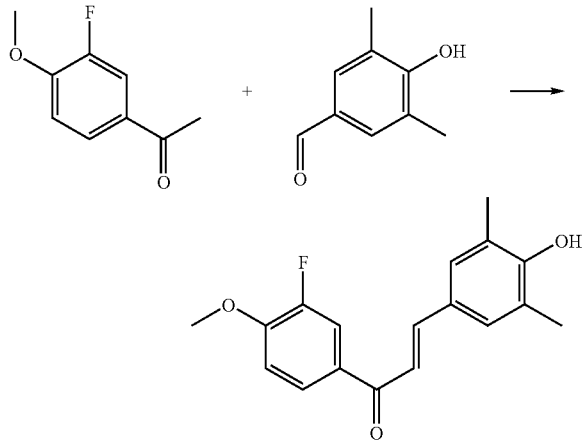

This compound was synthesized from 4'-methoxy-3'-fluoroacetophenone and 3,5-dimethyl-4-hydroxybenzaldehyde according to general method 1 described earlier.

The product crystallized in the reaction medium and was drained, then washed with heptane.

1H NMR CDCl₃ δppm: 2.30 (s, 6H), 3.98 (s, 3H), 7.04 (t, 1H, J=8.30 Hz), 7.31 (s, 2H), 7.35 (d, 1H, J=15.69 Hz), 7.74 (d, 1H, J=15.69 Hz), 7.79-7.87 (m, 2H)

Intermediate Compound 15:

1-(4-Methoxy-3-methylphenyl)-3-(4-hydroxy-3,5-dimethylphenyl)prop-2-en-1-one

This compound was synthesized from starting material 15 and 3,5-dimethyl-4-hydroxybenzaldehyde according to general method 1 described earlier.

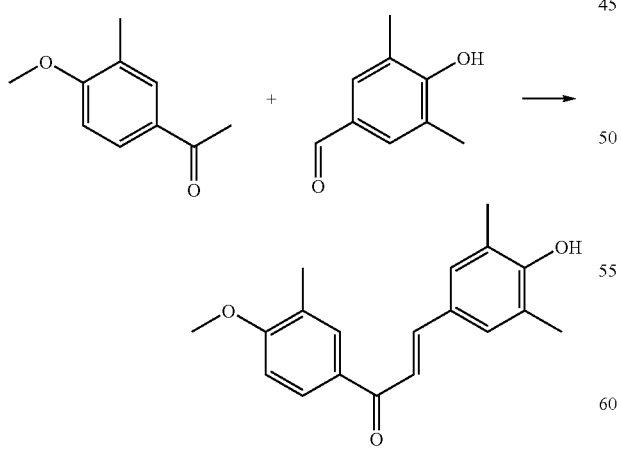

The product crystallized in the reaction medium and was drained, then washed with heptane.

1H NMR CDCl₃ δppm: 2.30 (s, 9H), 3.92 (s, 3H), 6.90 (d, 1H, J=8.45 Hz), 7.31 (s, 2H), 7.43 (d, 1H, J=15.52 Hz), 7.73 (d, 1H, J=15.52 Hz), 7.88 (s, 1H), 7.93 (d, 1H, J=8.45 Hz)

Intermediate Compound 16

1-(4-Hexylthio-3,5-dimethylphenyl)-3-(4-hydroxy-3,5-dimethylphenyl)prop-2-en-1-one

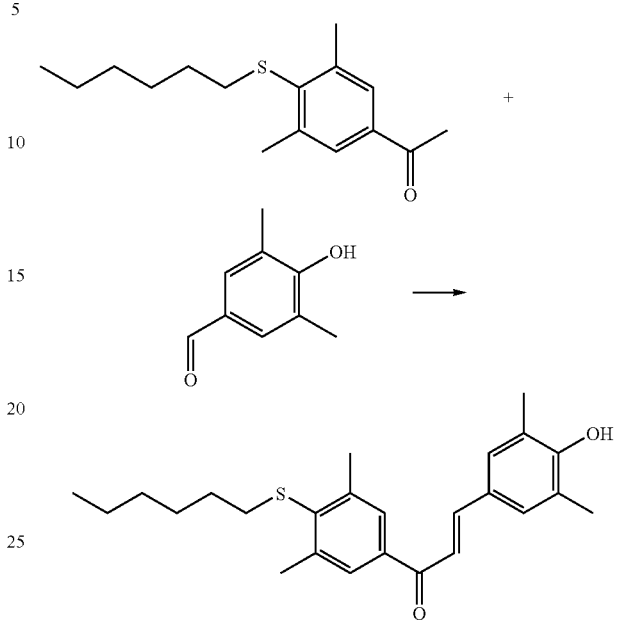

This compound was synthesized from starting material 17 and 3,5-dimethyl-4-hydroxybenzaldehyde according to general method 1 described earlier.

Purification was by chromatography on silica gel (elution: cyclohexane/ethyl acetate 8:2).

1H NMR CDCl₃ δppm: 0.88 (t, 3H, J=6.90 Hz), 1.20-1.50 (m, 8H), 2.30 (s, 6H), 2.63 (s, 6H), 2.70 (t, 2H, J=6.9 Hz), 7.32 (s, 2H), 7.36 (d, 1H, J=15.51 Hz), 7.72 (s, 2H), 7.73 (d, 1H, J=15.51 Hz)

Intermediate Compound 17

1-(2,5-Dimethoxyphenyl)-3-(4-hydroxy-3,5-dimethylphenyl)prop-2-en-1-one

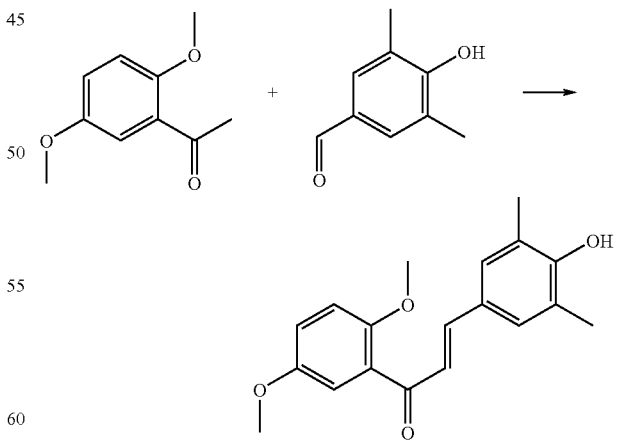

This compound was synthesized from 2',5'-dimethoxyacetophenone and 3,5-dimethyl-4-hydroxybenzaldehyde according to general method 1 described earlier.

Purification was by chromatography on silica gel (elution: cyclohexane/ethyl acetate 7:3).

1H NMR CDCl$_3$ δppm: 2.27 (s, 6H), 3.74 (s, 3H), 3.82 (s, 3H), 6.93 (d, 1H, J=8.73 Hz), 7.02 (dd, 1H, J=8.73 Hz, J=3.27 Hz), 7.14 (d, 1H, J=3.27 Hz), 7.22 (d, 1H, J=15.81 Hz), 7.25 (s, 2H), 7.53 (d, 1H, J=15.81 Hz)

Intermediate Compound 18

1-(4-Bromophenyl)-3-(4-hydroxy-3,5-difluorophenyl)prop-2-en-1-one

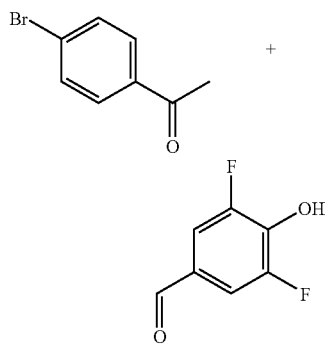

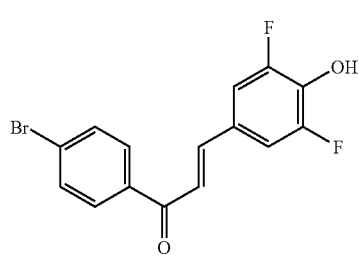

This compound was synthesized from 4'-bromoacetophenone and starting material 19 according to general method 1 described earlier.

The ethanol was eliminated by vacuum evaporation and the solid was washed with absolute ethanol.

1H NMR CDCl$_3$ δppm: 5.97 (s, 1H), 7.18 (d, 2H, J=8.30 Hz), 7.35 (d, 1H, J=15.36 Hz), 7.65 (m, 3H), 7.89 (d, 2H, J=8.30 Hz)

Intermediate Compound 19

1-(4-Methoxy-3-trifluoromethylphenyl)-3-(4-hydroxy-3,5-dimethylphenyl)prop-2-en-1-one

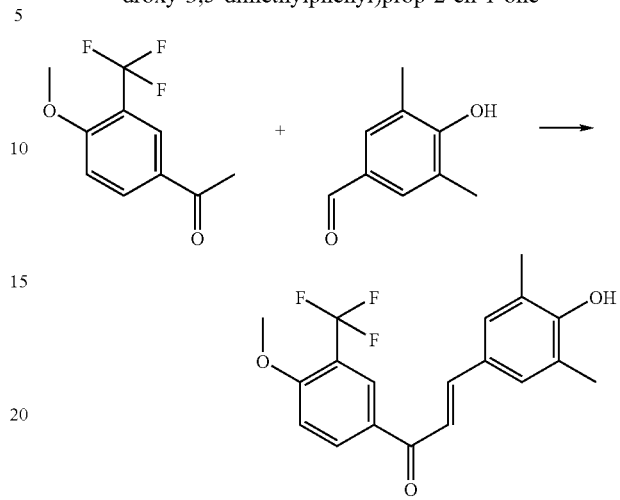

This compound was synthesized from starting material 20 and 3,5-dimethyl-4-hydroxybenzaldehyde according to general method 1 described earlier.

The ethanol was eliminated by vacuum evaporation and the solid was washed with absolute ethanol.

1H NMR DMSOd$_6$ δppm: 2.22 (s, 6H), 4.01 (s, 3H), 7.41 (d, 1H, J=9.00 Hz), 7.52 (s, 2H), 7.64 (d, 1H, J=15.40 Hz), 8.96 (s, 1H), 7.76 (d, 1H, J=15.40 Hz), 8.29 (d, 1H, J=1.60 Hz), 8.49 (dd, 1H, J=9.00 Hz, J=1.60 Hz)

Synthesis of the Inventive Compounds

Inventive Compound 1

1-(4-(Pentylthioethyloxy)phenyl)-3-(4-tert-butyloxycarbonyldimethylmethyloxy-3,5-dimethylphenyl)prop-2-en-1-one

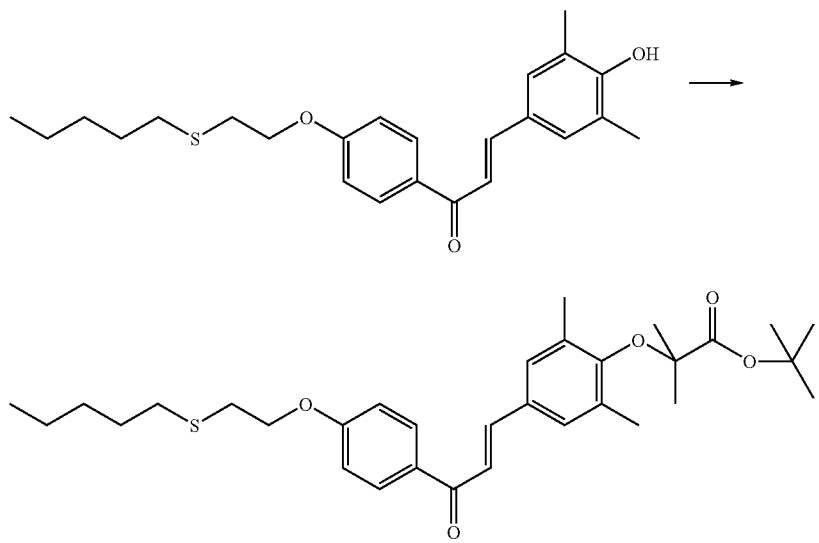

This compound was synthesized from Intermediate compound 1 and tert-butyl bromoisobutyrate according to general method 4 described earlier.

Purification was by chromatography on silica gel (elution: cyclohexane/ethyl acetate 9:1).

1H NMR CDCl₃ δppm: 0.91 (t, 3H, J=7.10 Hz), 1.37-1.69 (m, 21H) 2.27 (s, 6H), 2.63 (t, 2H, J=7.10 Hz), 2.93 (t, 2H, J=7.10 Hz), 4.21 (t, 2H, J=7.10 Hz), 6.97 (d, 2H, J=8.70 Hz), 7.28 (s, 2H), 7.44 (d, 1H, J=15.81 Hz), 7.70 (d, 1H, J=15.81 Hz), 8.03 (d, 2H, J=8.70 Hz)

Inventive Compound 2

1-(4-(Pentylthioethyloxy)phenyl)-3-(4-carboxydimethylmethyloxy-3,5-dimethylphenyl)prop-2-en-1-one

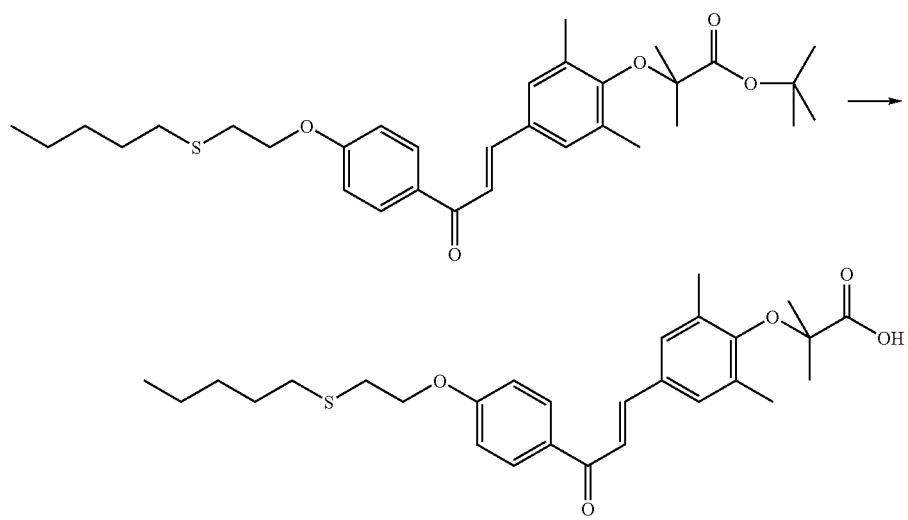

This compound was synthesized from compound 1 according to general method 6 described earlier.

Purification was by chromatography on silica gel (elution: dichloromethane-methanol: 98:2).

1H NMR CDCl₃ δppm: 0.84-0.89 (m, 3H), 1.39-1.24 (m, 4H), 1.39 (s, 6H), 1.50-1.57 (m, 2H), 2.22 (s, 6H), 2.61 (t, 2H, J=7.40 Hz), 2.90 (t, 2H, J=6.20 Hz), 4.26 (t, 2H, J=6.20 Hz), 7.09 (d, 2H, J=8.50 Hz), 7.57 (s, 2H), 7.59 (d, 1H, J=15.40 Hz), 7.83 (d, 1H, J=15.40 Hz), 8.15 (d, 2H, J=8.50 Hz), 12.90 (s, 1H)

MS (ES-MS): 483.2 (m−1)
MP° C.=85.2-89.8

Inventive Compound 3

1-(4-Hydroxy-3,5-dimethylphenyl)-3-(4-tert-butyloxycarbonyldimethylmethyloxy-3,5-dimethylphenyl)prop-2-ene-1-one

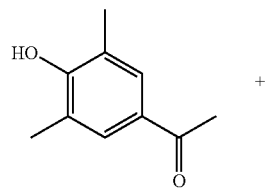 +

-continued

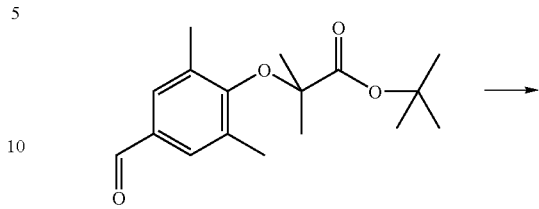

This compound was synthesized from starting material 3 and starting material 4 according to general method 1 described earlier.

Purification was by chromatography on silica gel (elution: dichloromethan/methanol: 95:5).

1H NMR CDCl₃ ppm: 1.46 (s, 6H), 1.53 (s, 9H), 2.27 (s, 6H), 2.33 (s, 6H), 7.28 (s, 2H), 7.43 (d, 1H, J=15.81 Hz), 7.69 (d, 1H, J=15.81 Hz), 7.74 (s, 2H)

Inventive Compound 4

1-(4-Hydroxy-3,5-dimethylphenyl)-3-(4-carboxy-dimethylmethyloxy-3,5-dimethylphenyl)prop-2-ene-1-one

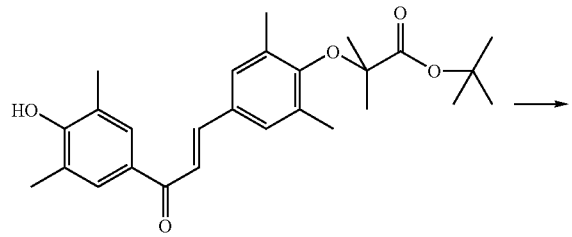

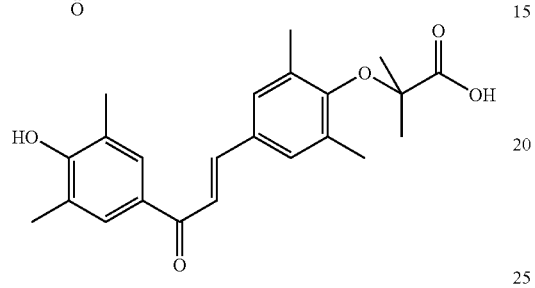

This compound was synthesized from compound 3 according to general method 6 described earlier.

Purification was by chromatography on silica gel (elution: dichloromethane/methanol: 98:2).

1H NMR CDCl₃ δppm: 1.39 (s, 6H), 2.22 (s, 6H), 2.25 (s, 6H), 7.33 (s, 2H), 7.45 (d, 1H, J=15.5 Hz), 7.69 (d, 1H, J=15.5 Hz), 7.75 (s, 2H)

MS (ES-MS): 381.3 (m−1)
MP° C.=199.3-199.8

This compound was synthesized from intermediate compound 2 and tert-butyl bromoisobutyrate according to general method 4 described earlier.

Purification was by chromatography on silica gel (elution: cyclohexane/ethyl acetate 85:15).

1H NMR CDCl₃ δppm: 1.43 (s, 6H), 1.53 (m, 13H), 1.65-1.75 (m, 2H), 1.75-1.85 (m, 2H), 1.85-1.97 (m, 1H), 2.28 (s, 6H), 1.46-1.52 (m, 1H), 3.12-3.21 (m, 2H), 3.58-3.63 (m, 1H), 4.05 (t, 2H, J=6.21 Hz), 6.97 (d, 2H, J=8.30 Hz), 7.29 (s, 2H), 7.45 (d, 1H, J=15.50 Hz), 7.70 (d, 1H, J=15.50 Hz), 8.03 (d, 2H, J=8.30 Hz)

Inventive Compound 5

1-(4-((R,S)-5-[1,2]dithiolan-3-ylpentyloxy)phenyl)-3-(4-tert-butyloxycarbonyl dimethyl methyloxy-3,5-dimethylphenyl)prop-2-en-1-one

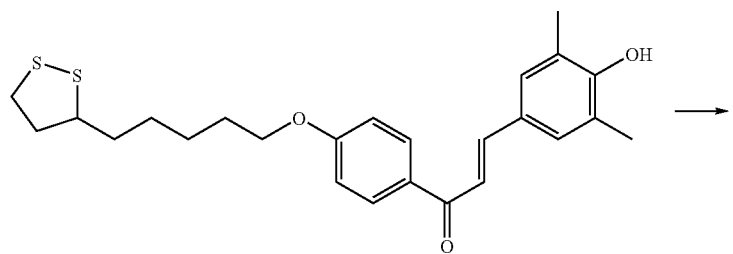

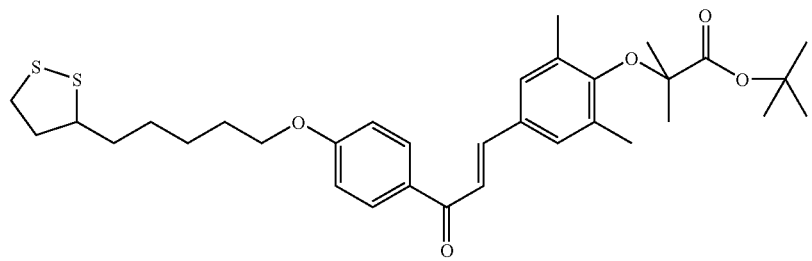

Inventive Compound 6

1-(4-((R,S)-5-[1,2]dithiolan-3-ylpentyloxy)phenyl)-3-(4-carboxydimethylmethyloxy-3,5-dimethylphenyl)prop-2-en-1-one

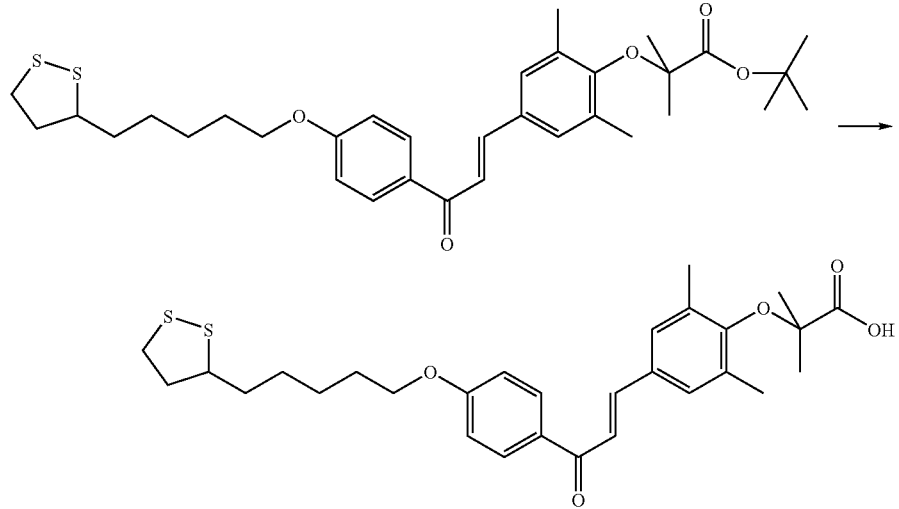

This compound was synthesized from compound 5 according to general method 6 described earlier.

Purification was by chromatography on silica gel (elution: dichloromethane/methanol: 98:2).

1H NMR CDCl$_3$ δppm: 1.56 (m, 10H), 1.67-1.77 (m, 2H), 1.77-1.90 (m, 2H), 1.90-1.97 (m, 1H), 2.30 (s, 6H), 2.43-2.52 (m, 1H), 3.11-3.22 (m, 2H), 3.58-3.63 (m, 1H), 4.05 (t, 2H, J=6.20 Hz), 6.98 (d, 2H, J=8.80 Hz), 7.31 (s,2H), 7.46 (d, 1H, J=15.80 Hz), 7.71 (d, 1H, J=15.80 Hz), 8.03 (d, 2H, J=8.80 Hz)

MS (ES-MS): 529.1 (M+1)

MP° C.: 182.7-186.6° C.

Inventive Compound 7

1-(4-Methylthiophenyl)-3-(4-tert-butyloxycarbonyidimethylmethyloxy-3,5-dibromophenyl)prop-2-ene-1-one

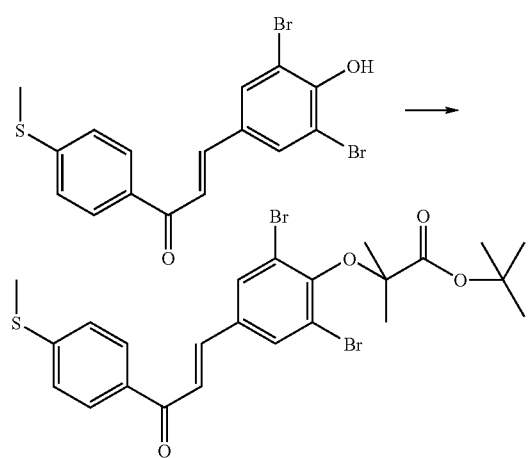

This compound was synthesized from intermediate compound 3 and tert-butyl bromoisobutyrate according to general method 4 described earlier.

Purification was by chromatography on silica gel (elution: cyclohexane/ethyl acetate 9:1).

1H NMR CDCl$_3$ δppm: 1.54 (s, 9H), 1.63 (s, 6H), 2.56 (s, 3H), 7.33 (d, 2H, J=8.50 Hz), 7.44 (d, 1H, J=15.70 Hz), 7.62 (d, 1H, J=15.70 Hz), 7.78 (s, 2H), 7.96 (d, 2H, J=8.50 Hz)

Inventive Compound 8

1-(4-Methylthiophenyl)-3-(4-carboxydimethylmethyloxy-3,5-dibromophenyl)prop-2-ene-1-one

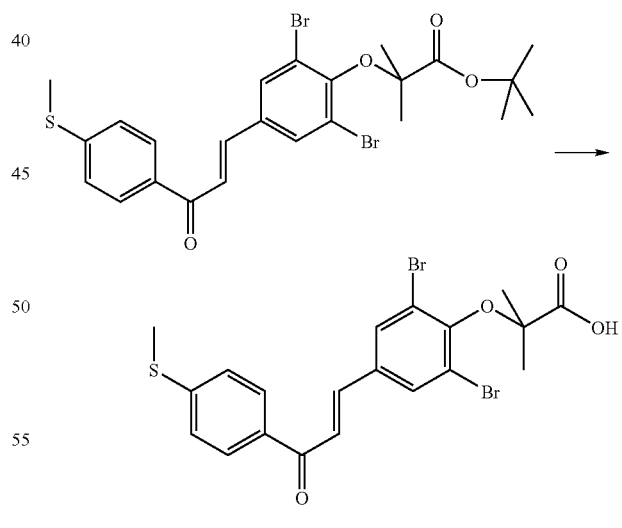

This compound was synthesized from compound 7 according to general method 6 described earlier.

Purification was by chromatography on silica gel (elution: dichloromethane/methanol: 98:2).

1H NMR CDCl$_3$ δppm: 1.54 (s, 6H), 2.51 (s, 3H), 7.41 (d, 2H, J=8.5 Hz), 7.64 (d, 1H, J=15.4 Hz), 8.04 (d, 1H, J=15.4 Hz), 8.15 (d, 2H, J=8.5 Hz), 8.29 (s, 2H), 12.93 (s, 1H)

MS (ES-MS): 513.2 (m−1)

Inventive Compound 10

1-(4-Cyclohexylethyloxyphenyl)-3-(4-tert-butyloxy-carbonyldimethylmethyloxy-3,5-dimethylphenyl)prop-2-en-1-one

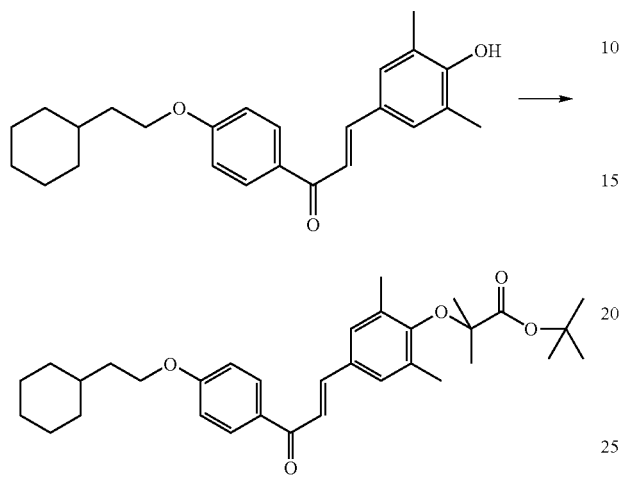

This compound was synthesized from intermediate compound 4 and tert-butyl bromoisobutyrate according to general method 4 described earlier.

Purification was by chromatography on silica gel (elution: dichloromethane/cyclohexane: 7:3).

1H NMR CDCl$_3$ δppm: 0.90-1.30 (m, 5H), 1.50 (m, 16H), 1.73 (m, 7H), 2.28 (s, 6H), 4.08 (t, 2H, J=6.54 Hz), 6.97 (d, 2H, J=8.70 Hz), 7.29 (s, 2H), 7.45 (d, 1H, J=15.75 Hz), 7.70 (d, 1H, J=15.75 Hz), 8.03 (d, 2H, J=8.70 Hz)

Inventive Compound 11

1-(4-Cyclohexylethyloxyphenyl)-3-(4-carboxydimethylmethyloxy-3,5-dimethylphenyl)prop-2-en-1-one

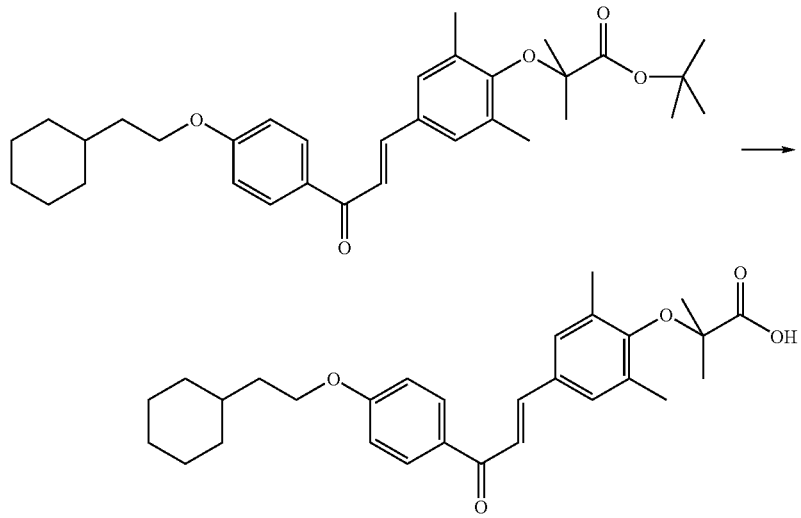

This compound was synthesized from compound 10 according to general method 6 described earlier.

Purification was by precipitation in a mixture of dichloromethane/heptane.

1H NMR CDCl$_3$ δppm: 0.90-1.30 (m, 5H), 1.56 (m, 7H), 1.70 (m, 7H), 2.30 (s, 6H), 4.09 (t, 2H, J=6.57 Hz), 6.98 (d, 2H, J=9.09 Hz), 7.32 (s, 2H), 7.4 (d, 1H, J=15.60 Hz), 7.71 (d, 1H, J=15.60 Hz), 8.04 (d, 2H, J=9.09 Hz)

MS (ES-MS): 465.3 (m+1)

MP° C.: 134.8-135.3

Inventive Compound 12

1-(4-Methylthio-3,5-dimethylphenyl)-3-(4-tert-butyloxycarbonyldimethylmethyloxy-3,5-dimethylphenyl)prop-2-en-1-one

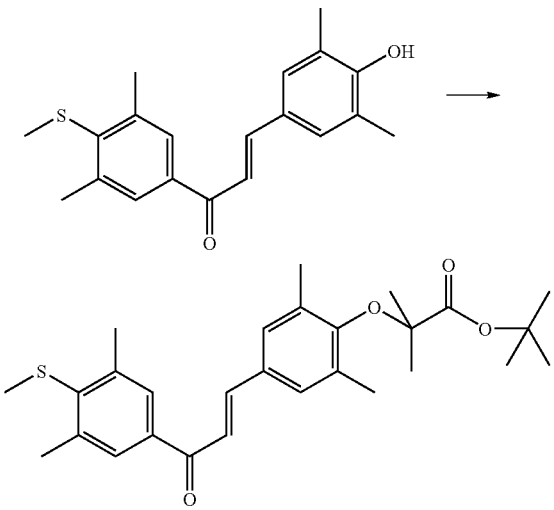

This compound was synthesized from intermediate compound 5 and tert-butyl bromoisobutyrate according to general method 4 described earlier.

Purification was by chromatography on silica gel (elution: cyclohexane/ethyl acetate 8:2).

1H NMR CDCl$_3$ δppm: 1.50 (s, 6H), 1.51 (s, 3H), 1.53 (s, 9H), 2.28 (s, 6H), 2.63 (s, 6H), 7.30 (s, 2H), 7.39 (d, 1H, J=15.69 Hz), 7.69 (d, 1H, J=15.69 Hz), 7.72 (s, 2H)

Inventive Compound 13

1-(4-Methylthio-3,5-dimethylphenyl)-3-(4-carboxydimethylmethyloxy-3,5-dimethylphenyl)prop-2-en-1-one

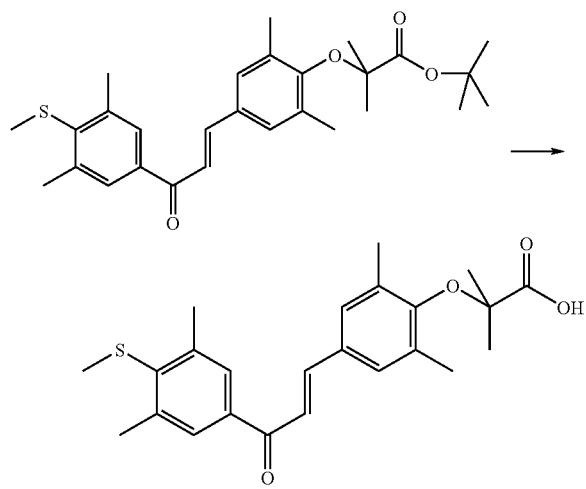

This compound was synthesized from compound 12 according to general method 6 described earlier.

Purification was by chromatography on silica gel (elution: dichloromethane/methanol 98:2).

1H NMR DMSOd$_6$ δppm: 1.39 (s, 6H), 2.22 (s, 6H), 2.28 (s, 3H), 2.59 (s, 6H), 7.56 (s, 2H), 7.62 (d, 1H, J=15.37 Hz), 7.79 (d, 1H, J=15.37 Hz), 7.89 (s, 2H), 12.95 (s, 1H)

MS (ES-MS): 412.9 (m+1)

MP° C.: 177.0-179.0

Inventive Compound 14

1-(4-Propyloxy-3,5-dimethylphenyl)-3-(4-tert-butyloxycarbonyldimethylmethyloxy-3,5-dimethylphenyl)prop-2-en-1-one

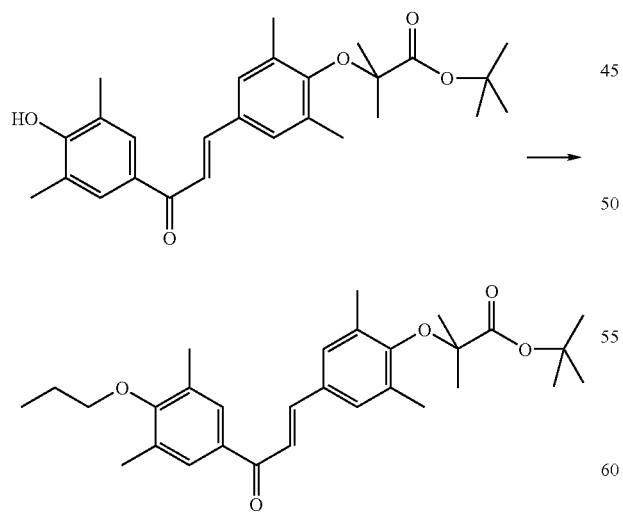

This compound was synthesized from compound 3 and propyl bromide according to general method 4 described earlier. The crude product obtained after elimination of the potassium carbonate and elimination of the solvents by vacuum evaporation was used for the synthesis of compound 15.

1H NMR CDCl$_3$ δppm: 1.09 (t, 3H, J=7.41 Hz), 1.46 (s, 6H), 1.58 (s, 9H), 1.83 (m, 2H), 2.27 (s, 6H), 2.35 (s, 6H), 3.78 (t, 2H, J=6.09 Hz), 7.29 (s, 2H), 7.41 (d, 1H, J=15.32 Hz), 7.68 (d, 1H, J=15.32 Hz), 7.70 (s, 2H)

Inventive Compound 15

1-(4-Propyloxy-3,5-dimethylphenyl)-3-(4-carboxydimethylmethyloxy-3,5-dimethylphenyl)prop-2-en-1-one

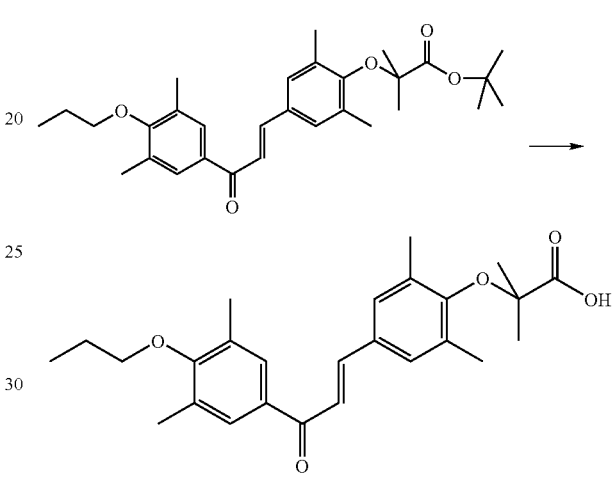

This compound was synthesized from compound 14 according to general method 6 described earlier.

Purification was by chromatography on silica gel (elution: dichloromethane/methanol 95:5).

1H NMR CDCl$_3$ δppm: 1.05 (t, 3H, J=7.29 Hz), 1.39 (s, 6H), 1.78 (m, 2H), 2.23 (s, 6H), 2.32 (s, 6H), 3.78 (m, 2H), 7.56 (s, 2H), 7.58 (d, 1H, J=16.26 Hz), 7.80 (d, 1H, J=16.26 Hz), 7.86 (s, 2H)

MS (ES-MS): 424.9 (m+1)

MP° C.: 188.5-189.7

Inventive Compound 16

1-(4-Methoxy-3,5-dimethylphenyl)-3-(4-tert-butyloxycarbonyldimethylmethyloxy-3,5-dimethylphenyl)prop-2-en-1-one

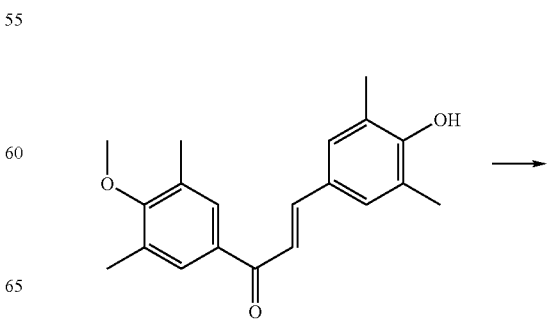

-continued

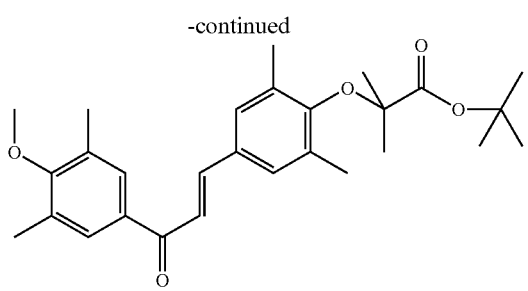

This compound was synthesized from intermediate compound 6 and tert-butyl bromoisobutyrate according to general method 4 described earlier.

Purification was by chromatography on silica gel (elution: cyclohexane/ethyl acetate 95:5).

1H NMR CDCl₃ δppm: 1.47 (s, 9H), 1.53 (s, 6H), 2.29 (s, 6H), 2.31 (s, 6H), 3.79 (s, 3H), 7.30 (s, 2H), 7.40 (d, 1H, J=15.50 Hz), 7.70 (d, 1H, J=15.50 Hz), 7.71 (s, 2H)

Inventive Compound 17

1-(4-Methoxy-3,5-dimethylphenyl)-3-(4-carboxydimethylmethyloxy-3,5-dimethylphenyl)prop-2-en-1-one

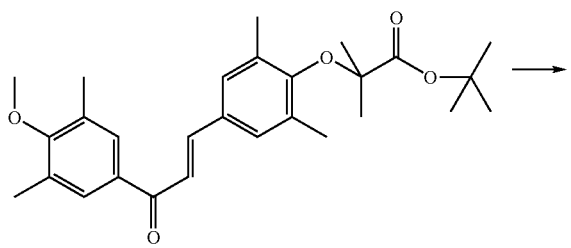

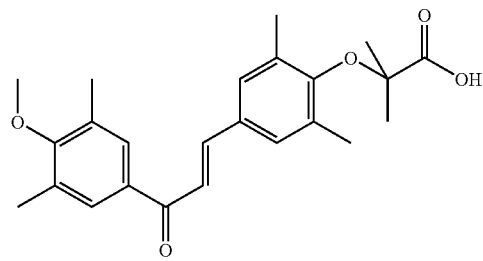

This compound was synthesized from compound 16 according to general method 6 described earlier.

Purification was by chromatography on silica gel (elution: dichloromethane/methanol 98:2).

1H NMR CDCl₃ δppm: 1.57 (s, 6H), 2.31 (s, 6H), 2.38 (s, 6H), 3.79 (s, 3H), 7.33 (s, 2H), 7.43 (d, 1H, J=15.81 Hz), 7.71 (d, 1H, J=15.81 Hz), 7.72 (s, 2H)

MS (ES-MS): 396.9 (m+1)

MP° C.: 166.6-168.8

Inventive Compound 18

1-(4-Hexyloxy-3,5-dimethylphenyl)-3-(4-tert-butyloxycarbonyldimethylmethyloxy-3,5-dimethylphenyl)prop-2-en-1-one

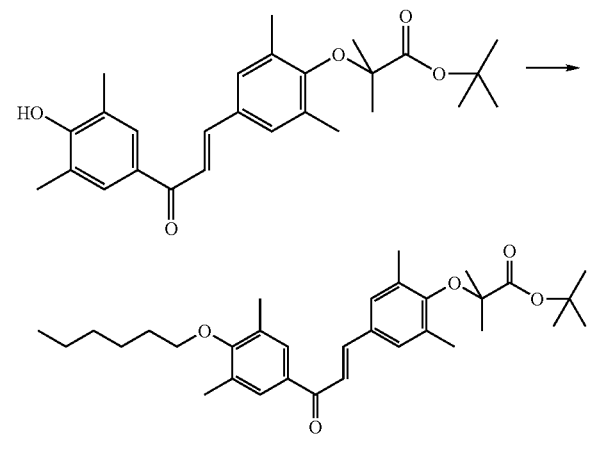

This compound was synthesized from compound 3 and hexyl bromide according to general method 4 described earlier. The crude product obtained after elimination of the potassium carbonate and elimination of the solvents by vacuum evaporation was used for the synthesis of compound 19.

1H NMR CDCl₃ δppm: 0.93 (t, 3H, J=8.58 Hz), 1.37 (m, 4H), 1.47 (s, 6H), 1.53 (m, 1H), 1.83 (m, 2H), 2.28 (s, 6H), 2.36 (s, 6H), 3.82 (t, 2H, J=6.54 Hz), 7.29 (s, 2H), 7.40 (d, 1H, J=15.57 Hz), 7.70 (d, 1H, J=15.57 Hz), 7.71 (s, 2H)

Inventive Compound 19

1-(4-Hexyloxy-3,5-dimethylphenyl)-3-(4-carboxydimethylmethyloxy-3,5-dimethyl phenyl)prop-2-en-1-one

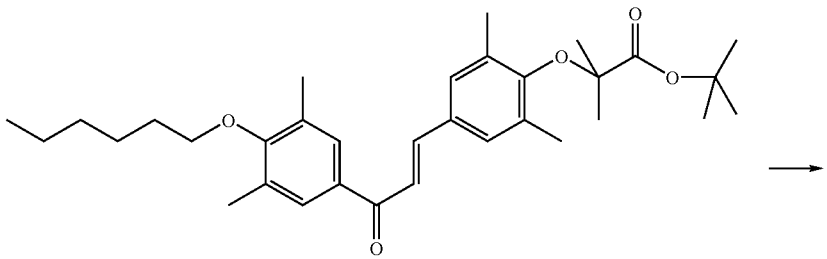

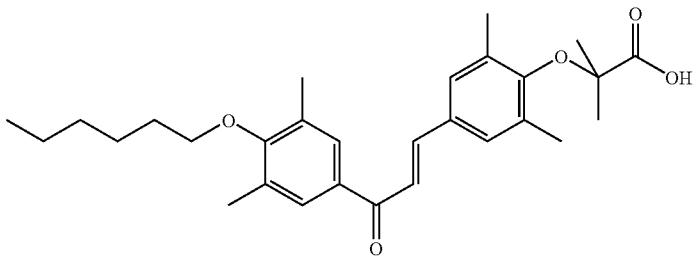

This compound was synthesized from compound 18 according to general method 6 described earlier.

Purification was by chromatography on silica gel (elution: dichloromethane/methanol 95:5).

1H NMR CDCl$_3$ δppm: 0.93 (t, 3H, J=7.02 Hz), 1.37 (m, 4H), 1.50 (m, 2H), 1.56 (s, 6H), 1.83 (m, 2H), 2.30 (s, 6H), 2.34 (s, 6H), 3.82 (t, 2H, J=6.57 Hz), 7.32 (s, 2H), 7.42 (d, 1H, J=15.48 Hz), 7.69 (d,1H, J=15.48 Hz), 7.71 (s, 2H)

MS (ES-MS): 466.9 (m+1)

MP° C.: 171.0-172.0

Inventive Compound 20

1-(4-Cyclohexylethyloxy-3,5-dimethylphenyl)-3-(4-tert-butyloxycarbonyldimethylmethyloxy-3,5-dimethylphenyl)prop-2-en-1-one

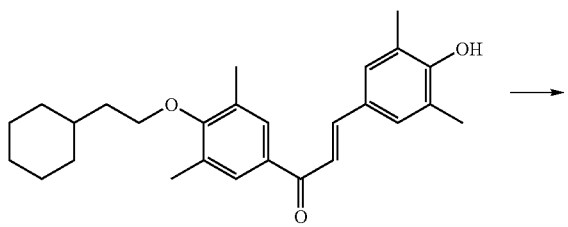 →

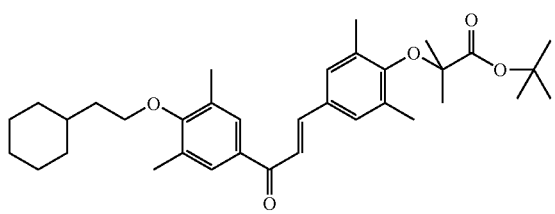

This compound was synthesized from intermediate compound 7 and tert-butyl bromoisobutyrate according to general method 4 described earlier.

Purification was by chromatography on silica gel (elution: cyclohexane/ethyl acetate 85:15).

1H NMR CDCl$_3$ δppm: 0.94-1.53 (m, 28H), 2.28 (s, 6H), 2.35 (s, 6H), 3.86 (t, 2H, J=6.75 Hz), 7.29 (s, 2H), 7.41 (d, 1H, J=15.76 Hz), 7.70 (d, 1H, J=15.76 Hz), 7.71 (s, 2H)

Inventive Compound 21

1-(4-Cyclohexylethyloxy-3,5-dimethylphenyl)-3-(4-carboxydimethylmethyloxy-3,5-dimethylphenyl)prop-2-en-1-one

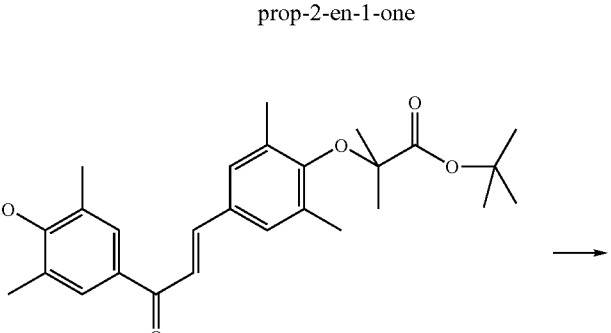 →

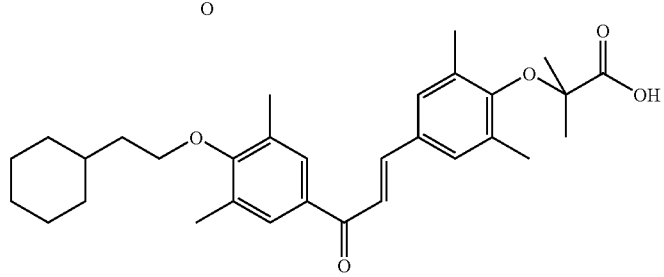

This compound was synthesized from compound 20 according to general method 6 described earlier.

Purification was by chromatography on silica gel (elution: dichloromethane/methanol 98:2).

1H NMR CDCl₃ δppm: 0.97-1.04 (m, 2H), 1.16-1.34 (m, 4H), 1.56 (s, 6H), 1.63-1.82 (m, 7H), 2.30 (s, 6H), 2.35 (s, 6H), 3.86 (t, 2H, J=6.60 Hz), 7.32 (s, 2H), 7.43 (d, 1H, J=15.81 Hz), 7.70 (d, 1H, J=15.81 Hz), 7.71 (s, 2H)

MS (ES-MS): 492.9 (m+1)

MP° C.: 166.4-167.7

Inventive Compound 22

1-(4-Cyclohexylthioethyloxyphenyl)-3-(4-tert-butyloxycarbonyldimethylmethyloxy-3,5-dimethylphenyl)prop-2-en-1-one

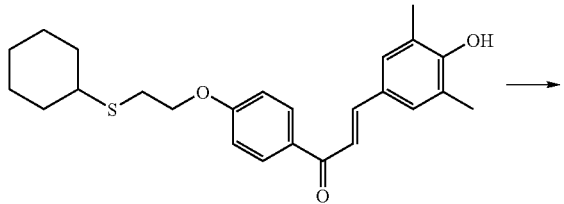

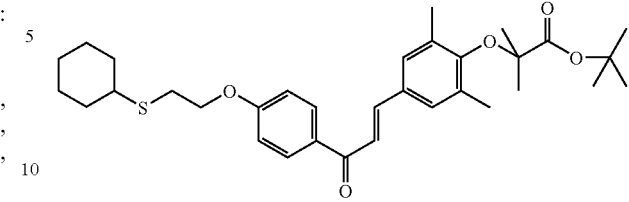

This compound was synthesized from intermediate compound 8 and tert-butyl bromoisobutyrate according to general method 4 described earlier.

Purification was by chromatography on silica gel (elution: cyclohexane/ethyl acetate 7:3).

1H NMR CDCl₃ δppm: 1.29 (m, 5H), 1.46 (s, 6H), 1.53 (s, 9H), 1.62 (m, 1H), 1.80 (m, 2H), 2.03 (m, 2H), 2.27 (s, 6H), 2.75 (m, 1H), 2.95 (t, 2H, J=6.81 Hz), 4.20 (t, 2H, J=6.81 Hz), 6.97 (d, 2H, J=9.24 Hz), 7.28 (s, 2H), 7.43 (d, 1H, J=15.78 Hz), 7.70 (d, 1H, J=15.78 Hz), 8.03 (d, 2H, J=9.24 Hz)

Inventive Compound 23

1-(4-Cyclohexylthioethyloxyphenyl)-3-(4-carboxydimethylmethyloxy-3,5-dimethylphenyl)prop-2-en-1-one

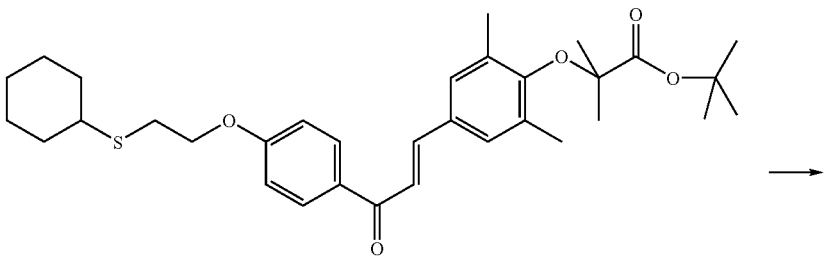

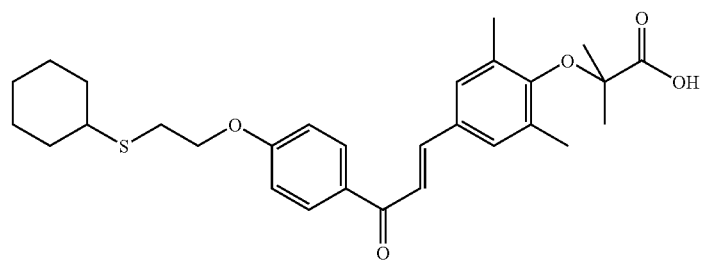

This compound was synthesized from compound 22 according to general method 6 described earlier.

Purification was by chromatography on silica gel (elution: dichloromethane/methanol 98:2).

1H NMR CDCl₃ δppm: 1.27-1.38 (m, 4H), 1.56 (s, 6H), 1.63-1.66 (m, 2H), 1.79-1.81 (m, 2H), 2.01-2.04 (m, 2H), 2.30 (s, 6H), 2.76-2.77 (m, 1H), 2.96 (t, 2H, J=7.08 Hz), 4.21 (t, 2H, J=7.08 Hz), 6.97 (d, 2H, J=8.61 Hz), 7.31 (s, 2H), 7.41 (d, 1H, J=15.60 Hz), 7.73 (d, 1H, J=15.60 Hz), 8.04 (d, 2H, J=8.61 Hz)

MS (Maldi-Tof): 496.67 (m+1)

MP° C.: 112.3-114

Inventive Compound 24

1-(2,4,5-Trimethylphenyl)-3-(4-tert-butyloxycarbonyldimethylmethyloxy-3,5-dimethylphenyl)prop-2-en-1-one

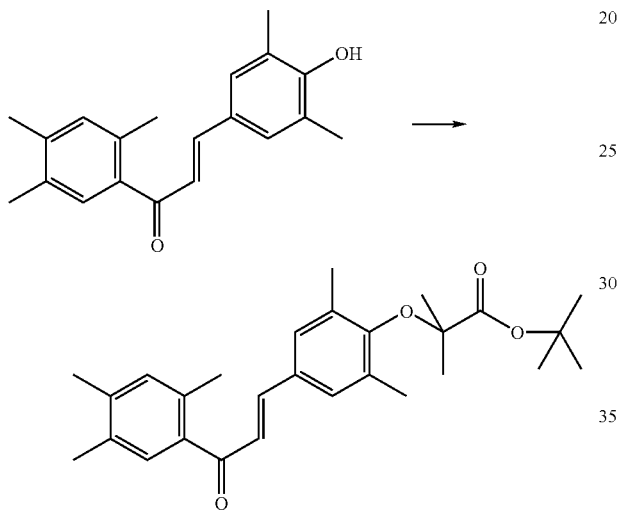

This compound was synthesized from intermediate compound 9 and tert-butyl bromoisobutyrate according to general method 4 described earlier.

Purification was by chromatography on silica gel (elution: cyclohexane/ethyl acetate 8:2).

1H NMR CDCl₃ δppm: 1.40-1.65 (m, 15H), 2.22 (s, 6H), 2.25 (s, 3H), 2.28 (s, 3H), 2.35 (s, 3H), 7.00 (s, 1H), 7.01 (d, 1H, J=15.70 Hz), 7.18 (s, 2H), 7.24 (s, 1H), 7.35 (d, 1H, 15.70 Hz)

Inventive Compound 25

1-(2,4,5-Trimethylphenyl)-3-(4-carboxydimethylmethyloxy-3,5-dimethylphenyl)prop-2-en-1-one

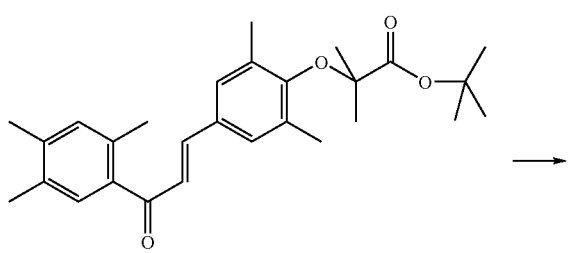

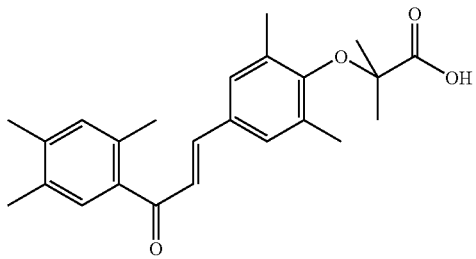

This compound was synthesized from compound 24 according to general method 6 described earlier.

Purification was by chromatography on silica gel (elution: dichloromethane/methanol 98:2).

1H NMR CDCl₃ δppm: 1.55 (s, 6H), 2.27 (s, 6H), 2.27-2.30 (m, 6H), 2.39 (s, 3H), 7.05 (s, 1H), 7.07 (d, 1H, J=15.24 Hz), 7.24 (s, 2H), 7.28 (s, 1H), 7.4 (d, 1H, J=15.78 Hz)

MS (ES-MS): 381.2 (m+1)

MP° C.: 168.7-173.3

Inventive Compound 26

1-(4-Cyclohexylthioethyloxy-3,5-dimethylphenyl)-3-(4-tert-butyloxycarbonyldimethylmethyloxy-3,5-dimethylphenyl)prop-2-en-1-one

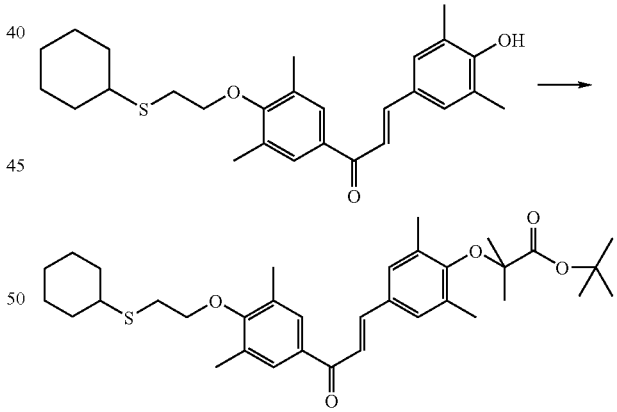

This compound was synthesized from intermediate compound 10 and tert-butyl bromoisobutyrate according to general method 4 described earlier.

Purification was by chromatography on silica gel (elution: cyclohexane/ethyl acetate 95:5).

1H NMR CDCl₃ δppm: 1.27-2.04 (m, 10H), 1.47 (s, 6H), 1.53 (s, 9H), 2.29 (s, 6H), 2.38 (s, 6H), 2.75 (m, 1H), 2.98 (t, 2H, J=6.84 Hz), 3.98 (t, 2H, J=6.84 Hz), 7.29 (s, 2H), 7.40 (d, 1H, J=15.63 Hz), 7.70 (d, 1H, J=15.63 Hz), 7.71 (s, 2H)

Inventive Compound 27

1-(4-Cyclohexylthioethyloxy-3,5-dimethylphenyl)-3-(4-carboxydimethylmethyloxy-3,5-dimethylphenyl)prop-2-en-1-one

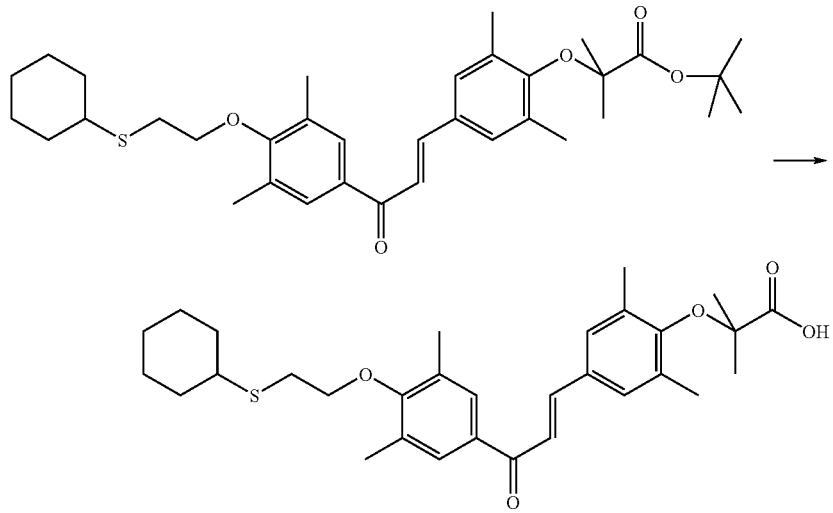

This compound was synthesized from compound 26 according to general method 6 described earlier.

Purification was by chromatography on silica gel (elution: dichloromethane/methanol 98:2).

1H NMR CDCl$_3$ δppm: 1.26-1.42 (m, 5H), 1.56 (s, 6H), 1.62-1.64 (m, 1H), 1.79-1.81 (m, 2H), 2.03-2.00 (m, 2H), 2.3 (s, 6H), 2.38 (s, 6H), 2.71-2.78 (m, 1H), 2.97 (t, 2H, J=7.00 Hz), 3.98 (t, 2H, J=7.00 Hz), 7.32 (s, 2H), 7.43 (d, 1H, J=15.78 Hz), 7.7 (d, 1H, J=15.24 Hz), 7.71 (s, 2H)

MS (MALDI-TOF): 524.78 (m+1)

MP° C.: 156.0-158.0

Inventive Compound 28

1-(4-Methylthiophenyl)-3-(4-tert-butyloxycarbonyldimethylmethyloxy-3-fluorophenyl)prop-2-en-1-one

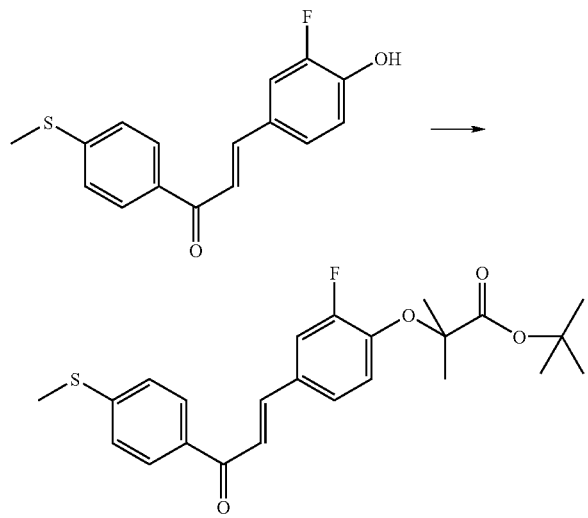

This compound was synthesized from intermediate compound 11 and tert-butyl bromoisobutyrate according to general method 4 described earlier.

Purification was by chromatography on silica gel (elution: cyclohexane/ethyl acetate 8:2).

1H NMR CDCl$_3$ δppm: 1.43 (s, 9H), 1.62 (s, 6H), 2.53 (s, 3H), 6.95 (t, 1H, J=8.07 Hz), 7.32 (d, 2H, J=8.64 Hz), 7.39 (m, 3H), 7.72 (d, 1H, J=15.50 Hz), 7.95 (d, 2H, J=8.64 Hz)

Inventive Compound 29

1-(4-Methylthiophenyl)-3-(4-carboxydimethylmethyloxy-3-fluorophenyl)prop-2-en-1-one

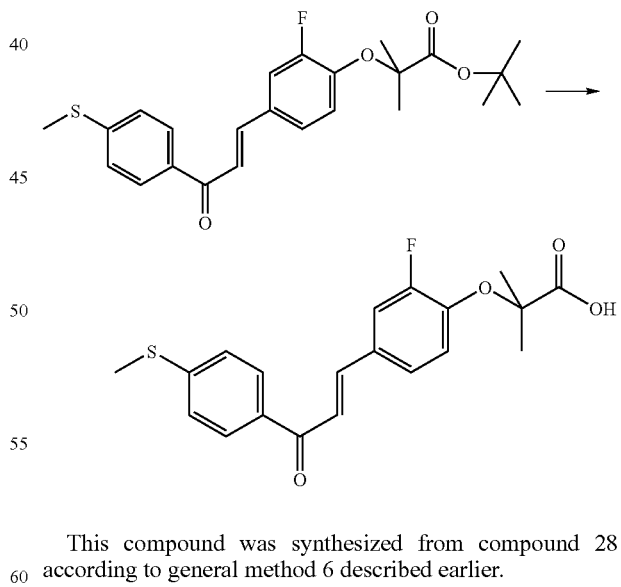

This compound was synthesized from compound 28 according to general method 6 described earlier.

It was purified by precipitation in a 70:30 mixture of dichloromethane/heptane.

1H NMR CDCl$_3$ δppm: 1.67 (s, 6H), 2.56 (s, 3H), 7.09 (t, 1H, J=8.19 Hz), 7.32 (m, 3H), 7.43 (m, 2H), 7.73 (d, 1H, J=15.24 Hz), 8.73 (d, 2H, J=8.73 Hz)

MS (ES-MS): 375.1 (m+1)

MP° C.: 142.2-144.6

Inventive Compound 30

1-(2,3,4,5,6-Pentamethylphenyl)-3-(4-tert-butyloxy-carbonyldimethylmethyloxy-3,5-dimethylphenyl)prop-2-en-1-one

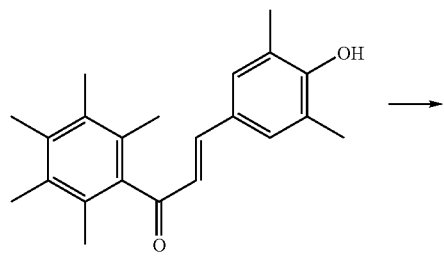

This compound was synthesized from intermediate compound 12 and tert-butyl bromoisobutyrate according to general method 4 described earlier.

Purification was by chromatography on silica gel (elution: cyclohexane/ethyl acetate 95:5).

1H NMR CDCl$_3$ δppm: 1.44 (s, 6H), 1.53 (s, 9H), 2.11 (s, 6H), 2.22 (s, 6H), 2.23 (s, 6H), 2.28 (s, 3H), 6.84 (d, 1H, J=16.26 Hz), 7.06 (d, 1H, J=16.26 Hz), 7.16 (s, 2H)

Inventive Compound 31

1-(2,3,4,5,6-Pentamethylphenyl)-3-(4-carboxydimethylmethyloxy-3,5-dimethylphenyl)prop-2-en-1-one

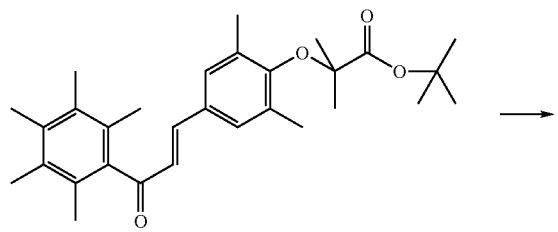

This compound was synthesized from compound 30 according to general method 6 described earlier.

Purification was by chromatography on silica gel (elution: dichloromethane/methanol 98:2).

1H NMR CDCl$_3$ ppm: 1.53 (s, 6H), 2.11 (s, 6H), 2.22 (s, 6H), 2.24 (s, 6H), 2.28 (s, 3H), 6.87 (d, 1H, J=16.20 Hz), 7.08 (d, 1H, J=16.20 Hz), 7.19 (s, 2H)

MS (ES-MS): 409.1 (m+1)

MP° C.: 192.8-194.2

Inventive Compound 32

1-(4-Phenyloxyphenyl)-3-(4-tert-butyloxycarbonyldimethylmethyloxy-3,5-dimethylphenyl)prop-2-en-1-one

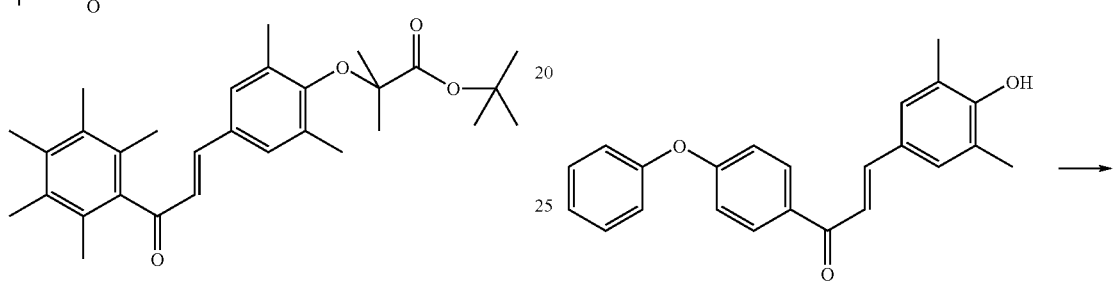

This compound was synthesized from intermediate compound 13 and tert-butyl bromoisobutyrate according to general method 4 described earlier.

Purification was by chromatography on silica gel (elution: cyclohexane/ethyl acetate 7:3).

1H NMR CDCl$_3$ δppm: 1.47 (s, 6H), 1.53 (s, 9H), 2.28 (s, 6H), 7.02 (d, 2H, J=8.70 Hz), 7.1 (d, 2H, J=7.92 Hz), 7.21 (t, 1H, J=7.35 Hz), 7.29 (s, 2H), 7.39-7.46 (m, 3H), 7.73 (d, 1H, J=16.20 Hz), 8.04 (d, 2H, J=8.70 Hz)

Inventive Compound 33

1-(4-Phenyloxyphenyl)-3-(4-carboxydimethylmethyloxy-3,5-dimethylphenyl)prop-2-en-1-one

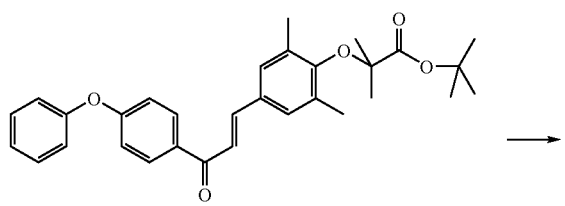

-continued

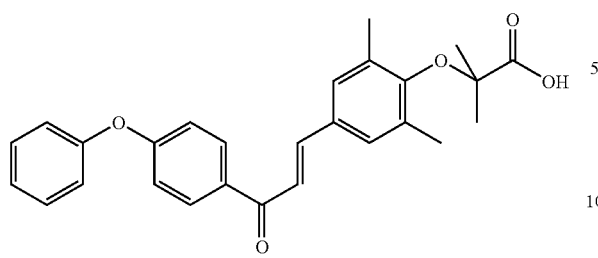

This compound was synthesized from compound 32 according to general method 6 described earlier.

Purification was by chromatography on silica gel (elution: dichloromethane/methanol 98:2).

1H NMR DMSOd$_6$ δppm: 1.39 (s, 6H), 2.22 (s, 6H), 7.08 (d, 2H, J=8.55 Hz), 7.15 (d, 2H, J=8.01 Hz), 7.25 (t, 1H, J=7.41 Hz), 7.47 (t, 2H, J=7.44 Hz), 7.55 (s, 2H), 7.62 (d, 1H, J=15.70 Hz), 7.82 (d, 1H, J=15.70 Hz), 8.19 (d, 2H, J=8.55 Hz)

MS (ES-MS): 430.9 (m+1)

MP° C.: 154.0-156.0

Inventive Compound 34

1-(4-Methoxy-3-fluorophenyl)-3-(4-tert-butyloxycarbonyldimethylmethyloxy-3,5-dimethylphenyl)prop-2-en-1-one

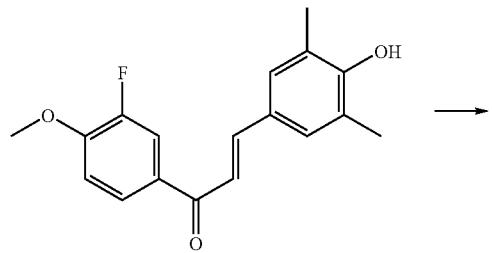

This compound was synthesized from intermediate compound 14 and tert-butyl bromoisobutyrate according to general method 4 described earlier.

Purification was by chromatography on silica gel (elution: cyclohexane/ethyl acetate 8:2).

1H NMR CDCl$_3$ δppm: 1.50 (s, 6H), 1.53 (s, 9H), 2.28 (s, 6H), 3.98 (s, 3H), 7.04 (t, 1H, J=8.07 Hz), 7.29 (s, 2H), 7.39 (d, 1H, J=15.70 Hz), 7.73 (d, 1H, J=15.70 Hz), 7.78-7.86 (m, 2H)

Inventive Compound 35

1-(4-Methoxy-3-fluorophenyl)-3-(4-carboxydimethylmethyloxy-3,5-dimethylphenyl)prop-2-en-1-one

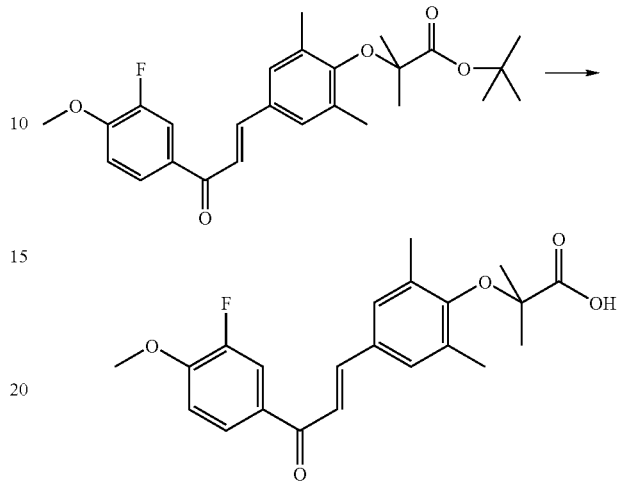

This compound was synthesized from compound 34 according to general method 6 described earlier.

Purification was by chromatography on silica gel (elution: dichloromethane/methanol 98:2).

1H NMR DMSOd$_6$ δppm: 1.39 (s, 6H), 2.22 (s, 6H), 3.95 (s, 3H), 7.31 (t, 1H, J=7.35 Hz), 7.57 (s, 2H), 7.60 (d, 1H, J=15.78 Hz), 7.83 (d, 1H, J=15.78 Hz), 7.99-8.06 (m, 2H)

MS (ES-MS): 387.1 (m+1)

MP° C.: 167.0-169.0

Inventive Compound 36

1-(4-Methoxy-3-methylphenyl)-3-(4-tert-butyloxycarbonyldimethylmethyloxy-3,5-dimethylphenyl)prop-2-en-1-one

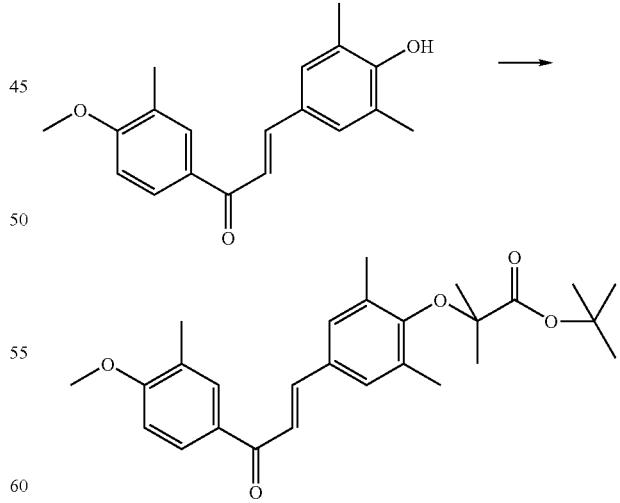

This compound was synthesized from intermediate compound 15 and tert-butyl bromoisobutyrate according to general method 4 described earlier.

1H NMR CDCl$_3$ δppm: 1.46 (s, 6H), 1.52 (s, 9H), 2.27 (s, 9H), 3.90 (s, 3H), 6.88 (d, 1H, J=8.73 Hz), 7.28 (s, 2H), 7.45

(d, 1H, J=16.11 Hz), 7.70 (d, 1H, J=16.11 Hz), 7.87 (s, 1H), 7.92 (dd, 1H, J=8.73 Hz, J=1.65 Hz)

Inventive Compound 37

1-(4-Methoxy-3-methylphenyl)-3-(4-carboxydimethylmethyloxy-3,5-dimethylphenyl)prop-2-en-1-one

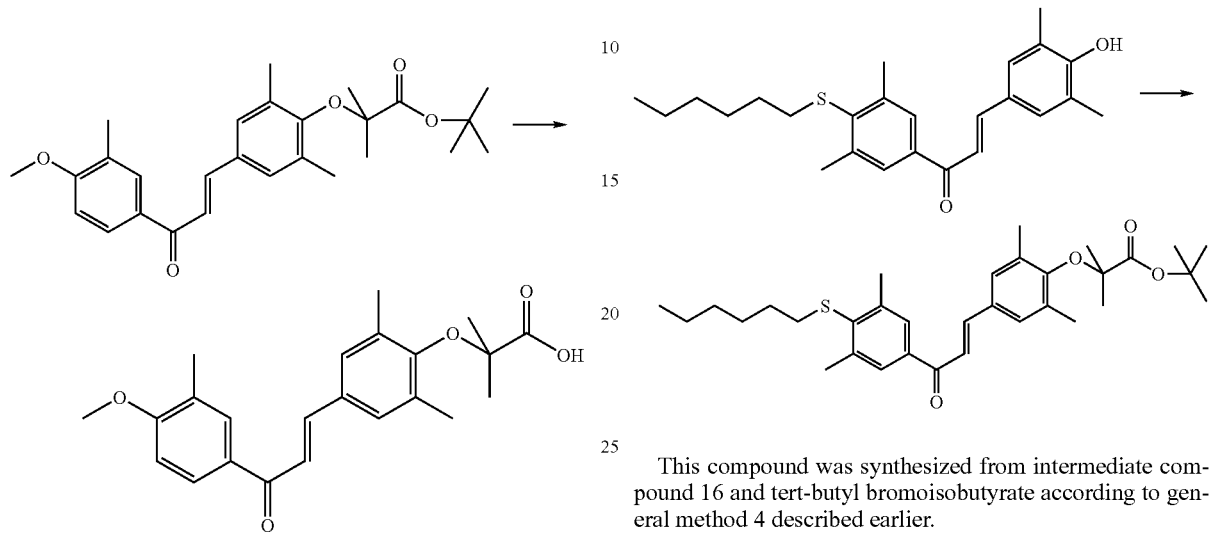

This compound was synthesized from compound 36 according to general method 6 described earlier.

Purification was by chromatography on silica gel (elution: dichloromethane/methanol 98:2) followed by recrystallization in acetonitrile.

1H NMR CDCl$_3$ δppm: 1.39 (s, 6H), 2.22 (s, 6H), 2.24 (s, 3H), 3.90 (s, 3H), 7.08 (d, 1H, J=8.55 Hz), 7.56 (s, 2H), 7.58 (d, 1H, J=16.71 Hz), 7.82 (d, 1H, J=15.51 Hz), 7.99 (s, 1H), 8.06 (d, 1H, 8.55), 12.95 (s, 1H)

MS (ES-MS): 383.2 (m+1)

MP° C.: 157.0-159.0

Inventive Compound 38

1-(4-Hexylthio-3,5-dimethylphenyl)-3-(4-tert-butyloxycarbonyldimethylmethyloxy-3,5-dimethylphenyl)prop-2-en-1-one This compound was synthesized from intermediate compound 16 and tert-butyl bromoisobutyrate according to general method 4 described earlier.

Purification was by chromatography on silica gel (elution: cyclohexane/ethyl acetate 9:1).

1H NMR CDCl$_3$ δppm: 0.88 (t, 3H, J=6.84 Hz), 1.25-1.62 (m, 8H), 1.47 (s, 6H), 1.53 (s, 9H), 2.29 (s, 6H), 2.62 (s, 6H), 2.70 (t, 2H, J=6.96 Hz), 7.30 (s, 2H), 7.39 (d, 1H, J=15.90 Hz), 7.70 (d, 1H, J=15.51 Hz), 7.71 (s, 2H)

Inventive Compound 39

1-(4-Hexylthio-3,5-dimethylphenyl)-3-(4-carboxydimethylmethyloxy-3,5-dimethylphenyl)prop-2-en-1-one

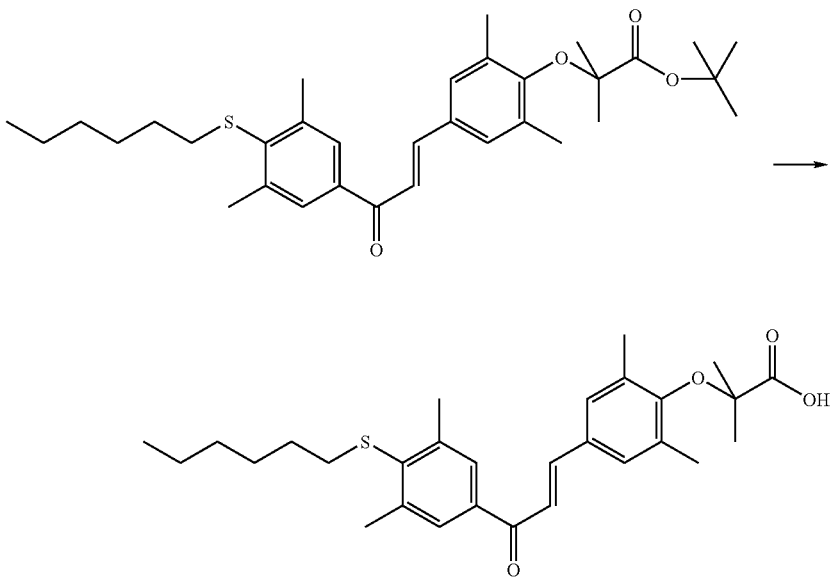

This compound was synthesized from compound 38 according to general method 6 described earlier.

Purification was by chromatography on silica gel (elution: dichloromethane/methanol 98:2).

1H NMR DMSOd$_6$ δppm: 0.84 (m, 3H), 1.22-1.40 (m, 8H), 2.08 (s, 6H), 2.22 (s, 6H), 2.58 (s, 6H), 2.73 (t, 2H, J=6.90 Hz), 7.57 (s, 2H), 7.63 (d, 1H, J=15.35 Hz), 7.8 (d, 1H, J=15.35 Hz), 7.89 (s, 2H)

MS (ES-MS): 483.2 (m+1)

MP° C.: 130.0-132.0

Inventive Compound 40

1-(2,5-Dimethoxyphenyl)-3-(4-tert-butyloxycarbonyldimethylmethyloxy-3,5-dimethylphenyl)prop-2-en-1-one

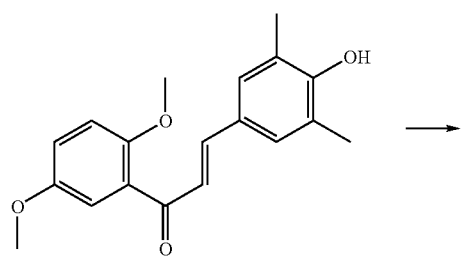

This compound was synthesized from intermediate compound 17 and tert-butyl bromoisobutyrate according to general method 4 described earlier.

Purification was by chromatography on silica gel (elution: cyclohexane/ethyl acetate 7:3).

1H NMR CDCl$_3$ ppm: 1.45 (s, 6H), 1.52 (s, 9H), 2.25 (s, 6H), 3.81 (s, 3H), 3.86 (s, 3H), 6.93 (d, 1H, J=9.24 Hz), 7.01 (dd, 1H, J=8.82 Hz, J=2.7 Hz), 7.14 (d, 1H, J=2.8 Hz), 7.22 (s, 2H), 7.26 (d, 1H, J=15.60 Hz), 7.52 (d, 1H, J=15.60 Hz)

Inventive Compound 41

1-(2,5-Dimethoxyphenyl)-3-(4-carboxydimethylmethyloxy-3,5-dimethylphenyl)prop-2-en-1-one

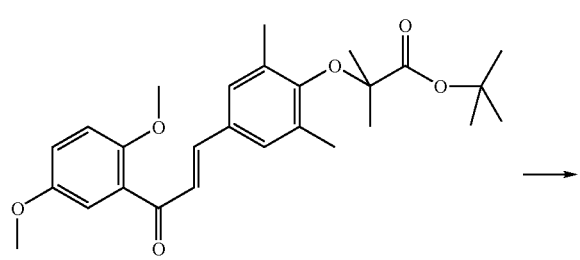

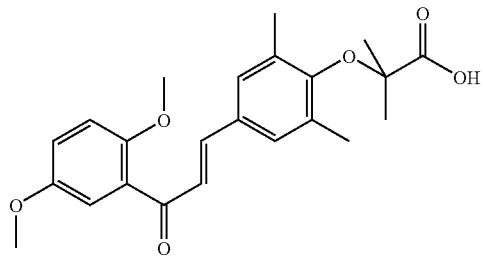

This compound was synthesized from compound 40 according to general method 6 described earlier.

Purification was by chromatography on silica gel (elution: dichloromethane/methanol 98:2).

1H NMR DMSOd$_6$ δppm: 1.38 (s, 6H), 2.19 (s, 6H), 3.75 (s, 3H), 3.8 (s, 3H), 7.00 (d, 1H, J=2.16 Hz), 7.12 (m, 2H), 7.26 (d, 1H, J=16.2 Hz), 7.37 (d, 1H, J=13.5 Hz), 7.4 (s, 2H)

MS (ES-MS): 398.3 (m−1)

MP° C.: oily product

Inventive Compound 42

1-(3,5-Dimethyl-4-(morpholin-4-ylethyloxy)phenyl)-3-(4-ethyloxycarbonyl dimethylmethyloxy-3,5-dimethylphenyl)prop-2-en-1-one hydrochloride

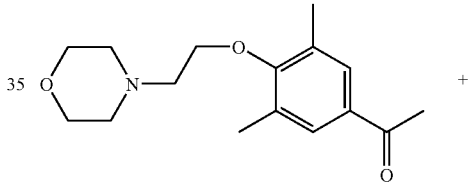

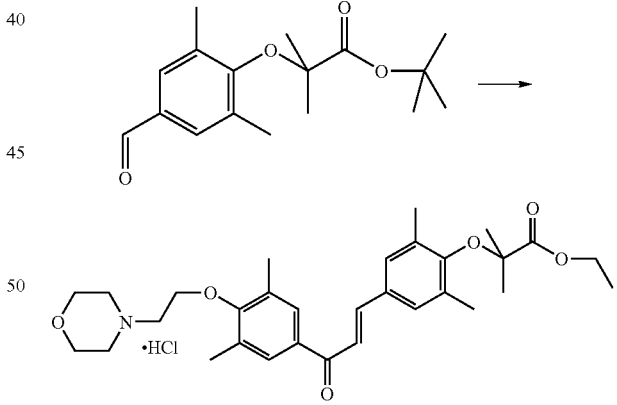

This compound was synthesized from starting materials 18 and 3 according to general method 1 described earlier. After elimination of the ethanol by vacuum evaporation compound 42 was obtained after triauration of the residual oil in diethyl ether.

1H NMR CDCl$_3$ δppm: 1.36 (t, 3H, J=6.84 Hz), 1.49 (s, 6H), 2.24 (s, 6H), 2.38 (s, 6H), 3.20 (s, 2H), 3.50 (s, 2H), 3.73 (d, 2H, J=11.04 Hz), 4.03 (d, 2H, J=11.04 Hz), 4.30-4.45 (m, 6H), 7.36 (d, 1H, J=15.75 Hz), 7.28 (s, 2H), 7.66 (m, 3H), 13.39 (s, 1H, N.HCl, exchange/D2O)

Inventive Compound 43

1-(3,5-Dimethyl-4-(morpholin-4-ylethyloxy)phenyl)-3-(4-carboxydimethylmethyloxy-3,5-dimethylphenyl)prop-2-en-1-one

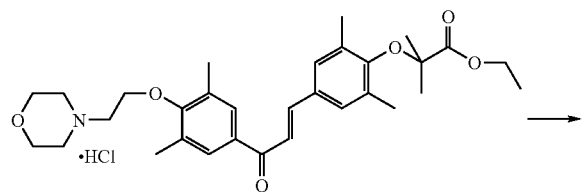

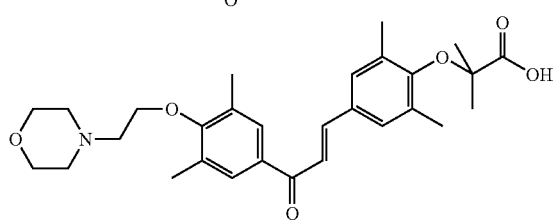

Compound 42 was dissolved in ethanol and 2M sodium hydroxide was added. The mixture was stirred for 18 hours at room temperature, then poured in water. The aqueous phase was washed with ethyl acetate, neutralized by addition of acetic acid, then extracted with diethyl ether. The precipitate which formed in the ether phase was drained and recrystallized in absolute ethanol.

1H NMR CDCl$_3$ δppm: 1.50 (s, 6H), 2.28 (s, 6H), 2.36 (s, 6H), 2.89 (m, 4H), 3.06 (t, 2H, J=5.46 Hz), 3.87 (m, 4H), 4.06 (t, 2H, J=5.46 Hz), 6.50 (s, 1H), 7.40 (d, 1H, J=15.78 Hz), 7.27 (s, 2H), 7.68 (m, 3H).

MS (MALDI-TOF): 496 (m+1)
MP° C.: 167-169

Inventive Compound 44

1-(4-Bromophenyl)-3-(4-tert-butyloxycarbonyldimethylmethyloxy-3,5-difluorophenyl)prop-2-en-1-one

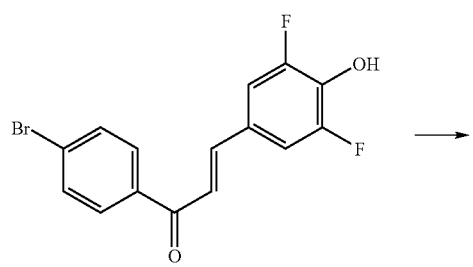

This compound was synthesized from intermediate compound 18 and tert-butyl bromoisobutyrate according to general method 4 described earlier.

Purification was by chromatography on silica gel (elution: cyclohexane/ethyl acetate 95:5).

1H NMR CDCl$_3$ δppm: 1.50 (s, 9H), 1.57 (s, 6H), 7.38 (d, 2H, J=8.50 Hz), 7.65 (d, 1H, J=15.78 Hz), 7.66 (m, 3H), 7.89 (d, 2H, J=8.50 Hz)

Inventive Compound 45

1-(4-Bromophenyl)-3-(4-carboxydimethylmethyloxy-3,5-difluorophenyl)prop-2-en-1-one

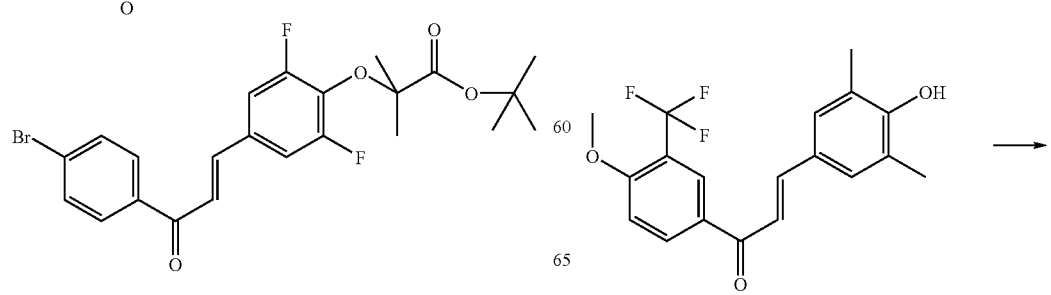

This compound was synthesized from compound 44 according to general method 6 described earlier.

Purification was by recrystallization in diisopropyl ether.

1H NMR CDCl$_3$ δppm: 1.65 (s, 6H), 7.24 (d, 2H, J=8.50 Hz), 7.41 (d, 1H, J=15.84 Hz), 7.66 (m, 3H), 7.89 (d, 2H, J=8.50 Hz)

MS (ES-MS): 425 (m+1)
MP° C.: 142

Inventive Compound 46

1-(4-Methoxy-3-trifluoromethylphenyl)-3-(4-tert-butyloxycarbonyldimethylmethyloxy-3,5-dimethylphenyl)prop-2-en-1-one -continued

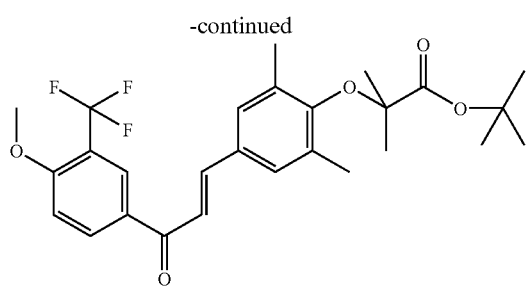

This compound was synthesized from intermediate compound 19 and tert-butyl bromoisobutyrate according to general method 4 described earlier.

Purification was by chromatography on silica gel (elution: cyclohexane/ethyl acetate 9:1).

1H NMR CDCl$_3$ δppm: 1.47 (s, 6H), 1.53 (s, 9H), 2.29 (s, 6H), 4.00 (s, 3H), 7.10 (d, 1H, J=8.65 Hz), 7.30 (s, 2H), 7.40 (d, 1H, J=15.27 Hz), 7.75 (d, 1H), 8.25 (d, 1H, J=8.65 Hz), 8.28 (s, 1H)

Inventive Compound 47

1-(4-Methoxy-3-trifluoromethylphenyl)-3-(4-carboxydimethylmethyloxy-3,5-dimethylphenyl)prop-2-en-1-one

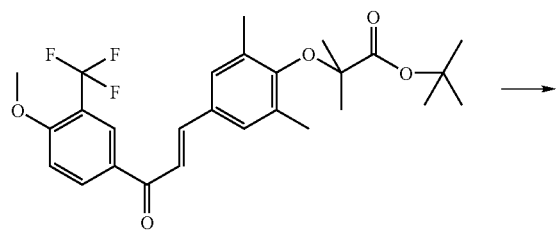

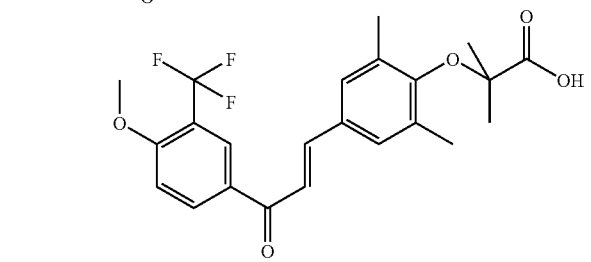

This compound was synthesized from compound 46 according to general method 6 described earlier. Compound 47 in pure state was obtained after eliminating the solvents by vacuum evaporation.

1H NMR DMSOd$_6$ δppm: 1.40 (s, 6H), 2.23 (s, 6H), 4.03 (s, 3H), 7.43 (d, 1H, J=8.7 Hz), 7.60 (s, 2H), 7.65 (d, 1H, J=15.40 Hz), 7.88 (d, 1H, J=15.40 Hz), 8.31 (s, 1H), 8.51 (d, 1H, J=8.70 Hz), 12.80 (s, 1H).

MS (ES-MS): 437.3 (m+1)

MP° C.: 182.5

Example 2

Evaluation of the Antioxidant Properties of the Inventive Compounds

Protection Against LDL Oxidation by Copper

The inventive compounds which were tested are the compounds whose preparation is described in the above examples.

LDL oxidation is an important alteration and plays a predominant role in the establishment and development of atherosclerosis (Jurgens, Hoff et al. 1987) The following protocol allows to demonstrate the antioxidant properties of compounds. Unless otherwise indicated, the reagents were from Sigma (St Quentin, France). LDL were prepared according to the method described by Lebeau et al. (Lebeau, Furman et al. 2000).

The solutions of test compounds were prepared at $10^{-2}$ M concentration in bicarbonate buffer (pH 9) and diluted in PBS to obtain final concentrations ranging from 0.1 to 100 μM Prior to oxidation, EDTA was removed from the LDL preparation by dialysis. Oxidation then took place at 30° C. by adding 100 μl of 16.6 μM CuSO$_4$ solution to 160 μL of LDL (125 μg protein/ml) and 20 μl of a test compound solution. The formation of dienes, the species under observation, was followed by measuring optical density at 232 nm in the samples treated with the compounds in the presence or absence of copper. Optical density at 232 nm was measured every 10 minutes for 8 hours in a thermostated spectrophotometer (Tecan Ultra 380). The analyses were performed in triplicate. The compounds were considered to have antioxidant activity when they induced a longer lag phase and reduced the rate of oxidation and the amount of dienes formed in comparison with the control sample. The inventors demonstrate that the inventive compounds have at least one of the aforementioned antioxidant properties indicating that the inventive compounds have intrinsic antioxidant activity.

Typical results are given in FIGS. 1a, 1b, 1c, 2a, 2b, 2c, 3a, 4a, 4b, 4c, 5a, 5b, 5c, 6a, 6b, 6c, 7a, 7b, 7c, 8a, 8b, 8c illustrating the antioxidant properties of the compounds according to the invention.

Example 3

Measurement of the Antioxidant Properties of the Inventive Compounds on Cell Cultures Culture Protocol:

Neuronal, neuroblastoma (human) and PC12 cells (rat) were the cell lines used for this type of study. PC12 cells were prepared from a rat pheochromocytoma and have been characterized by Greene and Tischler (Greene and Tischler, 1976). These cells are commonly used in studies of neuron differentiation, signal transduction and neuronal death. PC12 cells were grown as previously described (Farinelli, Park et al. 1996), in complete RPMI medium (Invitrogen) supplemented with 10% horse serum and 5% fetal calf serum.

(Primary) cultures of endothelial and smooth muscle cells were also used. Cells were obtained from Promocell (Promocell GmBH, Heidelberg) and cultured according to the supplier's instructions.

The cells were treated with different doses of the compounds ranging from 5 to 300 μM for 24 hours. The cells were then recovered and the increase in expression of the target genes was evaluated by quantitative PCR.

mRNA Measurement:

mRNA was extracted from the cultured cells treated or not with the inventive compounds. Extraction was carried out with the reagents of the Absolutely RNA RT-PCR miniprep kit (Stratagene, France) as directed by the supplier. mRNA was then assayed by spectrometry and quantified by quantitative RT-PCR with a Light Cycler Fast Start DNA Master Sybr Green I kit (Roche) on a Light Cycler System (Roche, France). Primer pairs specific for the genes encoding the antioxidant enzymes superoxide dismutase (SOD), catalase and glutathione peroxidase (GPx) were used as probes. Primer pairs specific for the βactin and cyclophilin genes were used as control probes.

An increase in mRNA expression of the antioxidant enzyme genes, measured by quantitative RT-PCR, was demonstrated in the different cell types used, when the cells were treated with the inventive compounds.

Control of Oxidative Stress:

Measurement of Oxidizing Species in the Cultured Cells:

The antioxidant properties of the compounds were also evaluated by means of a fluorescent tag the oxidation of which is followed by appearance of a fluorescence signal. The reduction in the intensity of the emitted fluorescence signal was determined in cells treated with the compounds in the following manner : PC12 cells cultured as described earlier (black 96-well plates, transparent bottom, Falcon) were incubated with increasing doses of $H_2O_2$ (0.25 mM-1 mM) in serum-free medium for 2 and 24 hours. After incubation, the medium was removed and the cells were incubated with 10 µM dichlorodihydrofluorescein diacetate solution (DCFDA, Molecular Probes, Eugene, USA) in PBS for 30 min at 37° C. in a 5% $CO_2$ atmosphere. The cells were then rinsed with PBS. The fluorescence emitted by the oxidation tag was measured on a fluorimeter (Tecan Ultra 384) at an excitation wavelength of 495 nm and an emission wavelength of 535 nm. The results are expressed as the percentage of protection relative to the oxidized control.

Fluorescence intensity was lower in the cells incubated with the inventive compounds than in untreated cells. These findings indicate that the inventive compounds promote inhibition of the production of oxidative species in cells subjected to oxidative stress. The previously described antioxidant properties are also effective at inducing antiradical protection in cultured cells.

Measurement of Lipid Peroxidation:

The protective effect of the compounds on lipid peroxidation in cultured cells (cell models noted hereinabove) was determined as follows: the different cell lines and the primary cell cultures were treated as described earlier, the cell supernatant was recovered after treatment and the cells were lysed and recovered for determination of protein concentration. Lipid peroxidation was detected as follows:

Lipid peroxidation was measured by using thiobarbituric acid (TBA) which reacts with lipid peroxidation of aldehydes such as malondialdehyde (MDA). After treatment, the cell supernatant was collected (900 µl) and 90 µl of butylated hydroxytoluene were added (Morliere, Moysan et al. 1991). One milliliter of 0.375% TBA solution in 0.25 M HCl containing 15% trichloroacetic acid was also added to the reaction medium. The mixture was heated at 80° C. for 15 min, cooled on ice and the organic phase was extracted with butanol. The organic phase was analysed by spectrofluorimetry ($\lambda exc=515$ nm and $\lambda em=550$ nm) on a Shimazu 1501 spectrofluorimeter (Shimadzu Corporation, Kyoto, Japan). TBARS are expressed as MDA equivalents using tetra-ethoxypropane as standard. The results were normalized for protein concentration.

The decrease in lipid peroxidation observed in the cells treated with the inventive compounds confirms the previous results.

The inventive compounds advantageously exhibit intrinsic antioxidant properties allowing to slow and/or inhibit the effects of an oxidative stress. The inventors also show that the inventive compounds are capable of inducing the expression of genes encoding antioxidant enzymes. These particular features of the inventive compounds allow cells to more effectively fight against oxidative stress and therefore be protected against free radical-induced damage.

Example 4

Evaluation of PPAR Activation in vitro by the Inventive Compounds

The inventive compounds which were tested are compounds having a carboxylic acid function, whose preparation is described in the above examples.

Nuclear receptors of the PPAR subfamily which are activated by two major pharmaceutical classes—fibrates and glitazones, widely used in the clinic for the treatment of dyslipidemias and diabetes—play an important role in lipid and glucose homeostasis. The following experimental data show that the inventive compounds activate PPARα, PPARγ et PPARδ in vitro.

PPAR activation was tested in vitro in RK13 epitheloid or COS-7 cell lines by measuring the transcriptional activity of chimeras composed of the DNA binding domain of the yeast gal4 transcription factor and the ligand binding domain of the different PPARs. These latter results were then confirmed in cell lines according to the following protocols:

The example is given for RK13 cells and for COS-7 cells.

Culture Protocols

RK13 cells were from ECACC (Porton Down, UK), COS-7 cells were from the ATCC (American Type Culture Collection) and were grown in DMEM medium supplemented with 10% (VN) fetal calf serum, 100 U/ml penicillin (Gibco, Paisley, UK) and 2 mM L-glutamine (Gibco, Paisley, UK). The culture medium was changed every two days. Cells were kept at 37° C. in a humidified 95% air/5% $CO_2$ atmosphere.

Description of Plasmids Used for Transfection

The plasmids pG5TkpGL3, pRL-CMV, pGal4-hPPARα, pGal4-hPPARγ, pGal4-hPPARδ and pGal4-φ have been described by Raspe, Madsen et al. (1999). The pGal4-mPPARα, pGal4-hPPARγ and pGal4-hPPARδ constructs were obtained by cloning into the pGal4-φ vector of PCR-amplified DNA fragments corresponding to the DEF domains of the human PPARα, PPARγ and PPARδ nuclear receptors.

Transfection

RK13 cells were seeded in 24-well culture dishes at $5 \times 10^4$ cells/well, COS-7 cells in 96-well culture dishes at $5 \times 10^4$ cells/well and transfected for 2 hours with the reporter plasmid pG5TkpGL3 (50 ng/well), the expression vectors pGal4-φ, pGal4-mPPARα, pGal4-hPPARα, pGal4-hPPARγ, pGal4-hPPARδ (100 ng/well) and the transfection efficiency control vector pRL-CMV (1 ng/well) according to the previously described protocol (Raspe, Madsen et al. 1999), then incubated for 36 hours with the test compounds. At the end of the experiment, the cells were lysed (Gibco, Paisley, UK) and luciferase activity was determined with a Dual-Luciferase™ Reporter Assay System kit (Promega, Madison, Wis., USA) for RK13 cells and Steady Glow Luciferase (Promega) for COS-7 cells according to the supplier's instructions as previously described. The protein content of the cell extracts was then measured with the Bio-Rad Protein Assay (Bio-Rad, Munich, Germany) as directed by the supplier.

The inventors demonstrate an increase in luciferase activity in cells treated with the inventive compounds and transfected with the pGal4-hPPARα plasmid. Said induction of luciferase activity indicates that the inventive compounds are activators of PPARα. The results are given in FIGS. 9a, 10a, 11a, 12a, 13a, 14a, 15a, 16a, 17a and 18a which illustrate the PPARα activator properties of inventive compounds.

The inventors demonstrate an increase in luciferase activity in cells treated with the inventive compounds and transfected with the pGal4-hPPARγ plasmid. Said induction of luciferase activity indicates that the inventive compounds are activators of PPARγ. The results are given in FIGS. 9b, 10b, 11b, 12b, 14b, 15b and 18b which illustrate the PPARγ activator properties of the inventive compounds.

The inventors demonstrate an increase in luciferase activity in cells treated with the inventive compounds and transfected with the pGal4-hPPARδ plasmid. Said induction of luciferase activity indicates that the inventive compounds are activators of PPARδ.

The results are given in FIGS. 11c, 13b, 14c and 15c which illustrate the PPARδ activator properties of the inventive compounds.

Example 5

Evaluation of the Anti-inflammatory Properties of the Inventive Compounds

An inflammatory response is observed in many neurological disorders, including multiple sclerosis, Alzheimer's disease and Parkinson's disease, cerebral ischemia and head trauma, and inflammation is also an important factor in neurodegeneration. In stroke, one of the first reactions of glial cells is to release cytokines and free radicals. This release of cytokines and free radicals results in an inflammatory response in the brain which can lead to neuron death (Rothwell, 1997).

Cell lines and primary cells were cultured as described hereinabove.

LPS (lipopolysaccharide) bacterial endotoxin (*Escherichia coli* 0111: B4) (Sigma, France) was reconstituted in distilled water and stored at 4° C. Cells were treated with LPS 1 μg/ml for 24 hours. To avoid interference from other factors the culture medium was completely changed.

TNF-α is an important factor in the inflammatory response to stress (oxidative stress for example). To evaluate TNF-α secretion in response to stimulation by increasing doses of LPS, the culture medium of stimulated cells was removed and TNF-α was assayed with an ELISA-TNF-α kit (Immunotech, France). Samples were diluted 50-fold so as to be in the range of the standard curve (Chang, Hudson et al. 2000).

The anti-inflammatory property of the compounds was characterized as follows: the cell culture medium was completely changed and the cells were incubated with the test compounds for 2 hours, after which LPS was added to the culture medium at 1 μg/ml final concentration. After a 24-hour incubation, the cell supernatant was recovered and stored at −80° C. when not treated directly. Cells were lysed and protein was quantified with the Bio-Rad Protein Assay kit (Bio-Rad, Munich, Germany) according to the supplier's instructions.

The measurement of the decrease in TNF-α secretion induced by treatment with the test compounds is expressed as pg/ml/μg protein and as the percentage relative to the control. These results show that the inventive compounds have anti-inflammatory properties.

Example 6

Evaluation of the Effects on Lipid Metabolism in vivo

The inventive compounds which were tested are the compounds whose preparation is described in the above examples.

Fibrates, widely used in human medicine for the treatment of dyslipidemiae involved the development of atherosclerosis, one of the leading causes of morbidity and mortality in industrialized countries, are potent activators of the PPARα nuclear receptor. The latter regulates the expression of genes involved in the transport (apolipoproteins such as Apo AI, ApoAII and ApoC-III, membrane transporters such as FAT) or catabolism of lipids (ACO, CPT-I or CPT-II). In rodents and humans, treatment with PPARα activators therefore leads to a decrease in plasma cholesterol and triglyceride levels.

The following protocols were designed to demonstrate a decrease in circulating triglyceride and cholesterol levels, and also highlight the interest of the inventive compounds for preventing and/or treating cardiovascular diseases.

Treatment of Animals

Apo E2/E2 transgenic mice were housed in a 12-hour light/dark cycle at a constant temperature of 20±3° C. After a 1-week acclimatization period, the mice were weighed and divided into groups of 6 animals selected such that the distribution of body weight was uniform. The test compounds were suspended in carboxymethylcellulose and administered by gastric lavage at the indicated doses, once a day for 7 days. Animals had access to food and water ad libitum. At the end of the experiments, animals were weighed and sacrificed under anesthesia. Blood was collected on EDTA. Plasma was isolated by centrifugation at 3000 rpm for 20 minutes. Liver samples were removed and stored frozen in liquid nitrogen for later analysis.

Determination of Serum Lipids and Apolipoproteins

Lipid concentrations in plasma (total cholesterol and free cholesterol, triglycerides and phospholipids) were determined by a colorimetric assay (Boehringer, Mannheim, Germany) according to the supplier's instructions. Plasma concentrations of apolipoproteins AI, AII and CIII were determined as previously described (Raspe et al. 1999, Asset G et al., Lipids, 1999).

FIGS. 19a, 19b, 19c and 19d give an example of the results where the activity of compound 2 on triglyceride and cholesterol metabolism is illustrated.

FIGS. 20a, 20b, 20c and 20d illustrate the activity of compounds 13, 33 and 39 on triglyceride and cholesterol metabolism.

RNA Analysis

Total RNA was isolated from the liver fragments by extraction with a mixture of guanidine thiocyanate/phenol acid/chloroform as previously described (Raspe et al. 1999). Messenger RNA was quantified by semi-quantitative or quantitative RT-PCR with the Light Cycler Fast Start DNA Master Sybr Green I kit (Hoffman-La Roche, Basel, Switzerland) on a Light Cycler System (Hoffman-La Roche, Basel, Switzerland). Primer pairs specific for the ACO, Apo CIII and Apo II genes were used as probes. Primer pairs specific for the 36B4, β-actin and cyclophilin genes were used as control probes. Alternatively, total RNA was analyzed by Northern Blot or Dot Blot according to the previously described protocol (Raspe et al., 1999).

Example 7

Evaluation of the Neuroprotective Effects of the Inventive Compounds in a Cerebral Ischemia-Reperfusion Model Prophylactic Model 1. Treatments of Animals 1.1 Animals and Administration of the Compounds C57 black/6 mice (wild-type) were used for this experiment.

Animals were maintained on a 12 hour light-dark cycle at a temperature of 20° C.±3° C. Water and food were available ad libitum. Food intake and weight gain were recorded.

The inventive compounds or the vehicle (0.5% carboxycellulose) were administered to the animals by gavage, for 14 days before ischemia induction in the middle cerebral artery.

1.2 Ischemia Induction-Reperfusion by Intraluminal Occlusion of the Middle Cerebral Artery:

Animals were anesthetized by intraperitoneal injection of 300 mg/kg chloral hydrate. A rectal probe was inserted and body temperature was maintained at 37° C.±0.5° C. Blood pressure was monitored throughout the experiment.

Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Measurement of Brain Infarct Volume

Twenty-four hours after reperfusion, animals previously treated or not with the compounds were euthanized by pentobarbital overdose.

Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema.

Analysis of the brain sections from treated animals revealed a marked decrease in infarct volume as compared with untreated animals. When the inventive compounds were administered to the animals before the ischemia (prophylactic effect), they were capable of inducing neuroprotection.

3/ Measurement of Antioxidant Activity

The mouse brains were frozen, crushed and reduced to powder, then resuspended in saline solution. The different enzyme activities were then measured as described by the following authors: superoxide dismutase (Flohe and Otting 1984); glutathione peroxidase (Paglia and Valentine 1967); glutathione reductase (Spooner, Delides et al. 1981); glutathione-S-transferase (Habig and Jakoby 1981); catalase (Aebi 1984).

Said different enzyme activities were increased in brain preparations from animals treated with the inventive compounds.

Curative or Acute Phase Treatment Model

1/ Ischemia Induction/Reperfusion by Intraluminal Occlusion of the Middle Cerebral Artery.

Animals such as those described previously were used for this experiment.

Animals were anesthetized by intraperitoneal injection of 300 mg/kg chloral hydrate. A rectal probe was inserted and body temperature was maintained at 37° C.±0.5° C. Blood pressure was monitored throughout the experiment. Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Treatment of Animals

Animals first subjected to ischemia-reperfusion were treated with the inventive compounds by the oral route (gavage) for 24 or 72 hours, twice a day.

3. Measurement of Brain Infarct Volume 24 or 72 hours after reperfusion, animals previously treated or not with the compounds were euthanized by pentobarbital overdose.

Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema.

In the case of curative treatment (treatment of the acute phase), animals treated with the inventive compounds had fewer brain lesions than untreated animals. In fact, the infarct volume was smaller when the inventive compounds were administered one or more times after ischemia-reperfusion.

Example 8

Evaluation of the Protective Effects of the Inventive Compounds in an Animal Model of Atherosclerosis By virtue of their PPAR activator and antioxidant properties, the inventive compounds have a beneficial effect on the progression of atheromatous plaque.

1. Treatment of Animals

Female Apo E2/E2 transgenic mice aged approximately 2 months were maintained on a 12 hour light-dark cycle at a constant temperature of 20° C.±3° C. throughout the acclimatization period and throughout the experiment.

After a 1-week acclimatization period, the mice were weighed and divided into groups of 8 animals selected such that the distribution of body weight was uniform. Animals had access to food and water ad libitum. They were fed a western-style diet containing 21% fat and 0.15% cholesterol for 2 weeks prior to treatment.

After this period, the test compounds were added to the feed at the indicated doses. The duration of treatment was 6 weeks.

The animals were weighed and sacrificed under anesthesia by cervical dislocation.

The heart was perfused in situ then prepared for histologic study, a needle was introduced into the right ventricle and the abdominal aorta was dissected.

Blood samples were taken before the start of the experiment, then once a week and at the end of the experiment.

Blood was collected on EDTA. Plasma was prepared by centrifugation at 3000 rpm for 20 minutes (determination of plasma cholesterol and triglycerides).

2/ Preparation of Slices for Histologic Study

Krebs Ringer solution was added for 10 minutes. The tissues were fixed overnight with 4% PAF in 10 mM PBS at −4° C. The samples were then washed with 100 mM PBS. The hearts were placed in 30% sucrose-Tris for one day then immersed in OCT (Tissue Teck) under vacuum for 30 minutes, then in a mould containing OCT, immersed in isopentane and cooled in liquid nitrogen. The samples were stored at −80° C.

10 μm-thick cryosections were cut from the aortic arch until disappearance of the valves and collected on gelatin-coated slides.

3. Histologic Analysis

The slides were stained with red oil and hematoxylin so as to differentiate the media from the intima. The different morphogenic parameters were determined with the help of an Olympus microscope and a color camera hooked up to an image analysis system. Damaged areas were quantified manually with a graphic panel hooked up to the same computer system.

The overall area of the atheromatous lesions was expressed in $\mu M^2$, and compared with the controls. The inventive compounds which were tested induced a significant decrease in lesion area, reflecting a reduction in lesion progression.

Example 9

Effects of the Inventive Compounds in vitro on Dendritic Cell Differentiation and Maturation Compound 39 was tested for its effects on the differentiation of monocyte-derived dendritic cells (by monitoring the acquisition of the dendritic cell phenotype).

For these experiments, blood samples from volunteer donors (Etablissement Francais du Sang) and monocytes were isolated by a standard protocol using anti-CD14-conjugated magnetic beads (Miltenyi Biotec). Monocytes isolated in this manner were then induced to differentiate by incubation for 6 days in culture medium containing a mixture of cytokines GM-CSF and IL-4 (20 ng/ml for each cytokine).

Compound 39 was added at t=0 and acquisition of the dendritic cell phenotype was followed by expression of the cell surface marker CD1a. The inventors thereby show that compound 39 markedly interfered with differentiation to dendritic cells by almost totally inhibiting the expression of CD1a at the cell surface (FIG. 21). Expression of the costimulation molecule CD80 was also reduced, to a lesser extent, whereas CD86 expression was slightly increased (data not shown). Similar results were obtained with inventive compounds 13 and 31. These findings suggest that the inventive compounds interfere with the differentiation of dendritic cells and stimulate dendritic cells towards the acquisition of an atypical phenotype.

The effects of said compounds were then studied on dendritic cell maturation induced by LPS (lipopolysaccharide). For these experiments, monocyte-derived dendritic cells obtained at D6 of differentiation were pretreated with the inventive compounds for 4 hours, then stimulated with LPS for 16 hours. In this manner it was shown that the compounds significantly interfered with LPS-induced transcription of the CCR7 receptor and the ELC ligand thereof (FIG. 22). FIG. 22 also shows that LPS-induced secretion of the inflammatory cytokine TNF-alpha was significantly reduced.

The decrease in the expression of ELC and CCR7—key genes in dendritic cell motility—suggests that the inventive compounds inhibit the migration of dendritic cells to secondary lymphoid organs and thereby interfere with the initiation of the immune response triggered by said cells.

The inventors thus demonstrate that monocyte-derived dendritic cells treated with compound 31 had a lower capacity to induce the proliferation of naive CD4+ T cells, by a Mixed Lymphocyte Reaction (MLR) (FIG. 23). For this experiment, increasing amounts of mature dendritic cells (treated or not with the compound) were incubated with a fixed amount of naive CD4+ T cells from another donor. After a 5-day incubation, BrdU (bromodeoxyuridine) was added for 24 hours and the incorporation thereof in T cells was determined by ELISA with anti-BrdU antibodies coupled to chemiluminescent tags.

Example 10

Effects of the Inventive Compounds in vivo in a Mouse Model of Ovalbumin (OVA)-Induced Allergic Asthma The effects of the inventive compounds were then analyzed in vivo in a mouse model of ovalbumin (OVA)-induced allergic asthma.

For these experiments, the mice were sensitized by intraperitoneal injections of ovalbumin in the presence of aluminium hydroxides, at D0 and D10 of the experiment. From D18 to D22, the mice received the inventive compounds (50 mg/kg to 200 mg/kg) daily by gavage. Three consecutive administrations of ovalbumin in aerosol form were given on D20, D21 and D22. The compound was administered approximately 1 hour before each administration. The mice were sacrificed on D24 and the bronchoalveolar lavage fluid (BAL) was collected to determine cellularity (macrophages, eosinophils, lymphocytes, neutrophils) and to measure cytokines IL-5, IL-13, IL-4.

The results show that the inventive compounds interfered with the differentiation and maturation of dendritic cells and inhibited the migration of said cells to secondary lymphoid organs. Moreover, the inventive compounds had a lower capacity to induce the proliferation of naive CD4+ T cells. The inventive compounds therefore interfere with the initiation of the immune response and hence represent an advantageous therapeutic tool for the treatment of asthma.

BIBLIOGRAPHY

Aebi, H. (1984). "Catalase in vitro." *Methods Enzymol* 105: 121-6.

Angeli V, Hammad H, Staels B, Capron M, Lambrecht B N, Trottein F. (2003) "Peroxisome proliferator-activated receptor gamma inhibits the migration of dendritic cells: consequences for the immune response" J Immunol. 170 (10): 5295-301.

Asset G, Staels B, Wolff R L, Bauge E, Madj Z, Fruchart J C, Dallongeville J. (1999). "Effects of Pinus pinaster and Pinus koraiensis seed oil supplementation on lipoprotein metabolism in the rat." *Lipids* 34(1): 39-44

Chang, R C, P. Hudson, et al. (2000). "Influence of neurons on lipopolysaccharide-stimulated production of nitric oxide and tumor necrosis factor-alpha by cultured glia." *Brain Res* 853(2): 236-44.

Desvergne, B. and W. Wahli (1999). "Peroxisome proliferator-activated receptors: nuclear control of metabolism." *Endocr Rev* 20(5): 649-88.

Dirnagl, U., C. Iadecola, et al. (1999). "Pathobiology of ischaemic stroke: an integrated view." *Trends Neurosci* 22(9): 391-7.

Farinelli, S E, D S Park, et al. (1996). "Nitric oxide delays the death of trophic factor-deprived PC12 cells and sympathetic neurons by a cGMP-mediated mechanism." *J Neurosci* 16(7): 2325-34.

Flohe, L. and F. Otting (1984). "Superoxide dismutase assays." *Methods Enzymol* 105: 93-104.

Gilgun-Sherki, Y, E. Melamed, et al. (2001). "Oxidative stress induced-neurodegenerative diseases: the need for antioxidants that penetrate the blood brain barrier." *Neuropharmacology* 40(8): 959-75.

Gosset, P, Charbonnier A S, Delerive P, Fontaine J, Staels B, Pestel J, Tonnel A B, Trottein F. (2001). "Peroxisome proliferator-activated receptor gamma activators affect the maturation of human monocyte-derived dendritic cells" *Eur J Immunol* 10: 2857-65.

Greene, L A and A S Tischler (1976). "Establishment of a noradrenergic clonal line of rat adrenal pheochromocytoma cells which respond to nerve growth factor." *Proc Natl Acad Sci USA* 73(7): 2424-8.

Guerre-Millo, M, P. Gervois, et al. (2000). "Peroxisome proliferator-activated receptor alpha activators improve insulin sensitivity and reduce adiposity." *J Biol Chem* 275(22): 16638-42.

Habig, W H and W B Jakoby (1981). "Assays for differentiation of glutathione S-transferases." *Methods Enzymol* 77: 398-405.

Hourton, D, P. Delerive, et al. (2001). "Oxidized low-density lipoprotein and peroxisome-proliferator-activated receptor alpha down-regulate platelet-activating-factor receptor expression in human macrophages." *Biochem J* 354(Pt 1): 225-32.

International Atherosclerosis Society "Harmonized Clinical Guidelines on Prevention of Atherosclerotic Vascular Disease" 2003.

Jurgens, G, H F. Hoff, et al. (1987). "Modification of human serum low density lipoprotein by oxidation—characterization and pathophysiological implications." *Chem Phys Lipids* 45(2-4): 315-36.

Komuves, L G, K. Hanley, et al. (2000). "Stimulation of PPARalpha promotes epidermal keratinocyte differentiation in vivo." *J Invest Dermatol* 115(3): 353-60.

Lebeau, J, C. Furman, et al. (2000). "Antioxidant properties of di-tert-butylhydroxylated flavonoids." *Free Radic Biol Med* 29(9): 900-12.

Mates, J M, C. Perez-Gomez, et al. (1999). "Antioxidant enzymes and human diseases." *Clin Biochem* 32(8): 595-603.

Morliere, P, A. Moysan, et al. (1991). "UVA-induced lipid peroxidation in cultured human fibroblasts." *Biochim Biophys Acta* 1084(3): 261-8.

Nencioni A, Grunebach F, Zobywlaski A, Denzlinger C, Brugger W, Brossart P., (2002) "Dendritic cell immunogenicity is regulated by peroxisome proliferator-activated receptor gamma" *J Immunol* 169(3):1228-35.

Paglia, D E and W N Valentine (1967). "Studies on the quantitative and qualitative characterization of erythrocyte glutathione peroxidase." *J Lab Clin Med* 70(1): 158-69.

Ram V J. (2003). "Therapeutic role of peroxisome proliferator-activated receptors in obesity, diabetes and inflammation. Prog Drug Res 60: 93-132.

Raspe, E, L. Madsen, et al. (1999). "Modulation of rat liver apolipoprotein gene expression and serum lipid levels by tetradecylthioacetic acid (TTA) via PPARalpha activation." *J Lipid Res* 40(11): 2099-110.

Rothwell, N J. (1997). "Cytokines and acute neurodegeneration." *Mol Psychiatry* 2(2): 120-1.

Spiegelman B M. (1998) "PPARgamma in monocytes: less pain, any gain?" *Cell,* 93(2):153-5

Spiegelmam B M. (1998) "PPAR-gamma: adipogenic regulator and thiazolidinedione receptor. *Diabetes* 47(4):507-14. Review.

Spooner, R J, A. Delides, et al. (1981). "Heat stability and kinetic properties of human serum glutathione reductase activity in various disease states." *Biochem Med* 26(2): 239-48.

Staels, B. and J. Auwerx (1998). "Regulation of apo A-I gene expression by fibrates." *Atherosclerosis* 137 Suppl: S19-23.

What is claimed is:

1. A compound derived from substituted 1,3-diphenyl-prop-2-en-1-one represented by general formula (I) below:

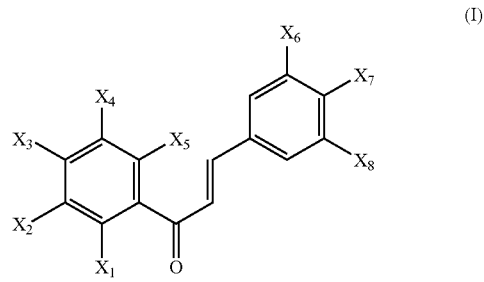

in which $X_7$ represents a group corresponding to the following formula: $G_7$-$R_7$ in which $G_7$ is an oxygen or sulfur atom and $R_7$ is an alkyl chain substitued by a substituent from group 1 or a substituent from group 2, optionally $R_7$ can also be substituted by an aryl group, the substituents from group 1 are selected in the group consisting of carboxy groups having the formula: —COOR$_a$, carbamoyl groups having the formula: —CONR$_b$R$_c$ or the tetrazolyl group, the substituents from group 2 are selected in the group consisting of sulfonic acid (—SO$_3$H) and sulfonamide groups having the formula: —SO$_2$NR$_b$R$_c$, with R$_a$, R$_b$ and R$_c$, which are the same or different, representing a hydrogen atom or an alkyl group substituted or not, $X_2$, $X_4$, $X_6$ and $X_8$, which are the same or different, represents alkyl groups, $X_1$ and $X_5$ are hydrogen atoms;

$X_3$ represents a halogen atom or a thionitroso group or correspond to the formula $(G_3$-$R_3)_n G'_3$-$R'_3$ in which:

n can have the values 0 or 1

$G_3$ and $G'_3$, which are the same or different, represent a single bond, an oxygen atom or a sulfur atom, $R_3$ and $R'_3$, which are the same or different, represent an alkyl, alkenyl, aryl or heterocycle group, $R'_3$ can also represent a hydrogen atom, $X_3$ not representing a heterocycle bound directly to the aromatic ring of the 1,3-diphenyl prop-2-en-1-one.

2. The compound according to claim 1, wherein at least one of the $G_3$, $G'_3$ or $G_7$ represents a sulfur atom.

3. The compound according to claim 1, wherein it is selected in the group consisting of:

1-(4-Mercapto-3,5-dimethylphenyl)-3-(4-carboxydimethylmethyloxy-3,5-dimethylphenyl)prop-2-en-1-one;

1-(4-Cyclohexylethylthio-3,5-dimethylphenyl)-3-(4-carboxydimethylmethyloxy-3,5-dimethylphenyl)prop-2-en-1-one;

1-(4-Hydroxy-3,5-dimethylphenyl)-3-(4-tert-butyloxycarbonyldimethylmethyloxy-3,5-dimethylphenyl)prop-2-ene-1-one;

1-(4-Hydroxy-3,5-dimethylphenyl)-3-(4-carboxydimethylmethyloxy-3,5-dimethylphenyl)prop-2-ene-1-one;

1-(4-Methylthio-3,5-dimethylphenyl)-3-(4-tert-butyloxycarbonyldimethylmethyloxy-3,5-dimethylphenyl)prop-2-en-1-one;

1-(4-Methylthio-3,5-dimethylphenyl)-3-(4-carboxydimethylmethyloxy-3,5-dimethylphenyl)prop-2-en-1-one;

1-(4-Propyloxy-3,5-dimethylphenyl)-3-(4-tert-butyloxycarbonyldimethylmethyloxy-3,5-dimethylphenyl)prop-2-en-1-one;

1-(4-Propyloxy-3,5-dimethylphenyl)-3-(4-carboxydimethylmethyloxy-3,5-dimethylphenyl)prop-2-en-1-one;

1-(4-Methoxy-3,5-dimethylphenyl)-3-(4-tert-butyloxycarbonyldimethylmethyloxy-3,5-dimethylphenyl)prop-2-en-1-one;

1-(4-Methoxy-3,5-dimethylphenyl)-3-(4-carboxydimethylmethyloxy-3,5-dimethylphenyl)prop-2-en-1-one;

1-(4-Hexyloxy-3,5-dimethylphenyl)-3-(4-tert-butyloxycarbonyldimethylmethyloxy-3,5-dimethylphenyl)prop-2-en-1-one;

1-(4-Hexyloxy-3,5-dimethylphenyl)-3-(4-carboxydimethylmethyloxy-3,5-dimethylphenyl)prop-2-en-1-one;

1-(4-Cyclohexylethyloxy-3,5-dimethylphenyl)-3-(4-tert-butyloxycarbonyldimethylmethyloxy-3,5-dimethylphenyl)prop-2-en-1-one;

1-(4-Cyclohexylethyloxy-3,5-dimethylphenyl)-3-(4-carboxydimethylmethyloxy-3,5-dimethylphenyl)prop-2-en-1-one;

1-(4-Cyclohexylthioethyloxy-3,5-dimethylphenyl)-3-(4-tert-butyloxycarbonyldimethylmethyloxy-3,5-dimethylphenyl)prop-2-en-1-one;

1-(4-Cyclohexylthioethyloxy-3,5-dimethylphenyl)-3-(4-carboxydimethylmethyloxy-3,5-dimethylphenyl)prop-2-en-1-one;

1-(4-Hexylthio-3,5-dimethylphenyl)-3-(4-tert-butyloxycarbonyldimethylmethyloxy-3,5-dimethylphenyl)prop-2-en-1-one; and 1-(4-Hexylthio-3,5-dimethylphenyl)-3-(4-carboxydimethylmethyloxy-3,5-dimethylphenyl)prop-2-en-1-one.

4. A method for preparing compounds of claim 1, wherein it comprises contacting in basic medium or in acidic medium at least one compound corresponding to formula (A) with at least one compound corresponding to formula (B), formulas (A) and (B) being:

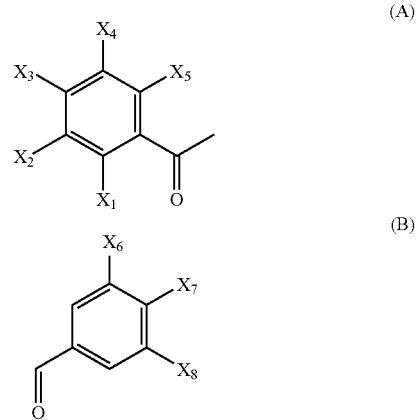

formulas in which $X_1$, $X_2$, $X_3$, $X_4$, $X_5$, $X_6$, $X_7$ and $X_8$ are defined in claim 1, $X_7$ can also represent a hydroxyl or thiol group.

5. A compound according to claim 1, as a medicament.

6. A pharmaceutical or cosmetic composition comprising, in a pharmaceutically acceptable support, at least one compound of claim 1, optionally in association with another therapeutic and/or cosmetic active agent.

* * * * *